(12) United States Patent
Zhang et al.

(10) Patent No.: US 11,180,495 B2
(45) Date of Patent: Nov. 23, 2021

(54) NITROGEN HETEROARYL DERIVATIVE HAVING CSF1R INHIBITORY ACTIVITY, AND PREPARATION METHOD THEREFOR AND APPLICATION THEREOF

(71) Applicant: Abbisko Therapeutics Co., Ltd., Shanghai (CN)

(72) Inventors: Mingming Zhang, Shanghai (CN); Baowei Zhao, Shanghai (CN); Hongping Yu, Shanghai (CN); Zhui Chen, Shanghai (CN); Yaochang Xu, Shanghai (CN)

(73) Assignee: ABBISKO THERAPEUTICS CO., LTD., Shanghai (CN)

( * ) Notice: Subject to any disclaimer, the term of this patent is extended or adjusted under 35 U.S.C. 154(b) by 60 days.

(21) Appl. No.: 16/619,364

(22) PCT Filed: Jun. 13, 2018

(86) PCT No.: PCT/CN2018/091045
§ 371 (c)(1),
(2) Date: Dec. 4, 2019

(87) PCT Pub. No.: WO2018/233527
PCT Pub. Date: Dec. 27, 2018

(65) Prior Publication Data
US 2020/0140431 A1  May 7, 2020

(30) Foreign Application Priority Data
Jun. 19, 2017 (CN) .......................... 201710464777.7

(51) Int. Cl.
| C07D 471/04 | (2006.01) |
| C07D 519/00 | (2006.01) |
| A61K 35/02 | (2015.01) |
| A61P 35/02 | (2006.01) |

(52) U.S. Cl.
CPC ............ *C07D 471/04* (2013.01); *A61P 35/02* (2018.01); *C07D 519/00* (2013.01)

(58) Field of Classification Search
CPC ..... C07D 471/04; C07D 519/00; A61K 35/02
USPC ................................................... 514/259.41
See application file for complete search history.

(56) References Cited

FOREIGN PATENT DOCUMENTS

| CN | 101223169 A | 7/2008 |
| CN | 105120864 A | 12/2015 |
| CN | 110467615 * | 4/2019 |
| WO | 2008064265 A2 | 5/2008 |
| WO | 2014145023 A1 | 9/2014 |

OTHER PUBLICATIONS

Int'l Search Report dated Aug. 20, 2018 in Int'l Application No. PCT/CN2018/091045.
Font et al., "A simple approach for the regioselective synthesis of imidazo[1,2-a]pyrimidiones and pyrimido[1,2-a]pyrimidinones," Tetrahedron, vol. 62, pp. 1433-1443 (2006).
Office Action dated Mar. 25, 2020 in CN Application No. 201880021734.4.
Chitu et al., "Emerging Roles for CSF-1 Receptor and its Ligands in the Nervous System," Trends in Neuroscience, vol. 39, No. 6, pp. 378-393 (2016).
Conway et al., "Inhibition of colony-stimulating-factor-1 signaling in vivo with the orally bioavailable cFMS kinase inhibitor GW2580," PNAS, vol. 102, No. 44, p. 16078-16083 (2005).
Crespo et al., "Tyrosine Kinase Inhibitors Ameliorate Autoimmune Encephalomyelitis in a Mouse Model of Multiple Sclerosis," J. Clin. Immunol., vol. 31, pp. 1010-1020 (2011).
He et al., "c-Fms Signaling Mediates Neurofibromatosis Type-1 Osteoclast Gain-In-Functions," PLOS ONE, vol. 7, No. 11, e46900, pp. 1-9 (2012).
Liu et al., "Macrophage colony-stimulating factor and its receptor signaling augment glycated albumin-induced retinal microglial inflammation in vitro," BMC Cell Biology, vol. 12, No. 5, pp. 1-11 (2011).
Martinez-Muriana et al., "CSF1R blockade slows the progression of amyotrophic lateral sclerosis by reducing microgliosis and invasion of macrophages into peripheral nerves," Scientific Reports, vol. 6:25663, pp. 1-13 (2016).

(Continued)

*Primary Examiner* — Niloofar Rahmani
(74) *Attorney, Agent, or Firm* — Panitch Schwarze Belisario & Nadel LLP

(57) ABSTRACT

This application describes a nitrogen heteroaryl derivative having CSF1R inhibitory activity, and a preparation method therefor and an application thereof. Compounds in the present invention has a structure represented by formula (I) as below, and the definition on substituents is as stated in the description and the claims. The compounds in the this application can be widely applied to preparation of drugs for treating cancer, tumor, autoimmune disease, metabolic disease, or metastatic disease, in particular ovarian cancer, pancreatic cancer, prostate cancer, breast cancer, cervical cancer, glioblastoma, multiple myeloma, metabolic disease, neurodegenerative disease, metastasis of primary tumor sites, or osseous metastatic cancer, and a new generation of CSF1R inhibitor drugs is expected to be developed.

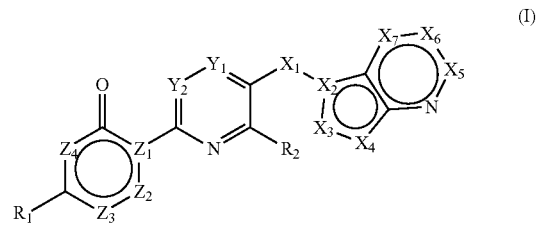

(I)

9 Claims, No Drawings

(56) References Cited

OTHER PUBLICATIONS

Olmos-Alonso et al., "Pharmacological targeting of CSF1R inhibits microglial proliferation and prevents the progression of Alzheimer's-like pathology," Brain, vol. 139, pp. 891-907 (2016).

Trias et al., "Post-paralysis tyrosine kinase inhibition with masitinib abrogates neuroinflammation and slows disease progression in inherited amyotrophic lateral sclerosis," Journal of Neuroinflammation, vol. 13, No. 177, pp. 1-12 (2016).

* cited by examiner

NITROGEN HETEROARYL DERIVATIVE HAVING CSF1R INHIBITORY ACTIVITY, AND PREPARATION METHOD THEREFOR AND APPLICATION THEREOF

CROSS-REFERENCE TO RELATED APPLICATION

This application is a Section 371 of International Application No. PCT/CN2018/091045, filed Jun. 13, 2018, which was published in the Chinese language on Dec. 27, 2018, under International Publication No. WO 2018/233527 A1, which claims priority under 35 U.S.C. § 119(b) to Chinese Patent Application No. 201710464777.7, filed on Jun. 19, 2017, the disclosures of which are incorporated herein by reference in their entireties.

TECHNICAL FIELD

The present invention belongs to the field of pharmaceutical synthesis, and particularly relates to an azaaryl derivative with CSF-1R inhibitory activity, a preparation method therefor and a use thereof.

BACKGROUND

CSF-1R (cFMS) stands for colony-stimulating factor 1 receptor. CSF-1R, as well as cKIT, FLT3 and PDGFRA&B, belong to the type III growth hormone receptor family. This receptor is a membrane protein, and is expressed on the surface of macrophages and monocytes. The extracellular domain of this receptor is capable of binding to the macrophage colony-stimulating factor, and the intracellular domain tyrosine kinase can activate downstream cell growth and proliferation signal pathways for macrophages and monocytes, such as MAPK, PI3K, etc. Therefore, CSF-1R signal pathway is critical for the development and differentiation of macrophages and monocytes and the physiological function of tumor-associated macrophages (TAMs).

In recent years, immune checkpoint inhibitors have become popular in the field of cancer treatment. This type of drugs significantly inhibited the growth of tumors clinically, and some patients have complete regression after treatment. However, clinical data have shown that only about 30% of patients responded to immune checkpoint inhibitors, such as anti-PD-1/PD-L1 antibody. Due to the lack of related biomarkers, how to select patients who may respond remains an unsolved problem. Additionally, immune checkpoint inhibitors will cause immune-related side effects in clinical practice, and therefore, experienced clinicians and medical institutions are needed to conduct such treatment. Therefore, how to combine immune checkpoint inhibitors with small-molecule inhibitors to reduce toxic and side effects and increase the response rate of cancer patients is an urgent problem to be solved in the research and development of antineoplastic drugs.

With the advancement in cancer immunotherapy in recent years, tumor-associated macrophages (TAMs) and myeloid-derived suppressor cells (MDSCs) are considered to contribute directly to the formation of an immunosuppressive tumor microenvironment and the angiogenesis process supporting tumor growth. Meanwhile, clinical studies have shown that the number of TAMs is negatively correlated with the prognosis of cancer patients. The result of an efficacy study in mice proved that inhibiting the CSF-1R signal pathway can remarkably decrease the number of immunosupppresive macrophages in tumors, and increase the content of CD8-positive T cells. These study results demonstrated that CSF-1R small-molecule inhibitors may reverse the immunosuppressive microenvironment in the tumor, promote the activation of the immune system, and prolong the lifespan of cancer patients.

The selectivity is a common problem for small-molecule kinase inhibitors, especially for the related members in the same kinase family. Because small-molecule drugs in the present patent may be used in combination with other immune checkpoint inhibitors in future clinical studies, the inventors attempted to improve the inhibitory effect on CSF-1R targets and the selectivity of related kinase receptors, prolong the therapeutic window and reduce the probability of clinical toxic and side effects by optimizing the molecular structure in the process of long-term research. Therefore, how to find CSF-1R small-molecule inhibitors with higher selectivity and meet the domestic demand on target and immune therapies for cancers, such as lung cancer, breast cancer, prostate cancer, ovarian cancer, cervical cancer, melanoma, pancreatic cancer, head and neck cancer, glioma, and giant cell tumor of tendon sheath, has become an important part of the current researches of scientists.

SUMMARY

The objective of the present invention is to provide a CSF-1R small-molecule inhibitor.

The first aspect of the present invention provides a compound of formula (I), a stereoisomer or pharmaceutically acceptable salt thereof:

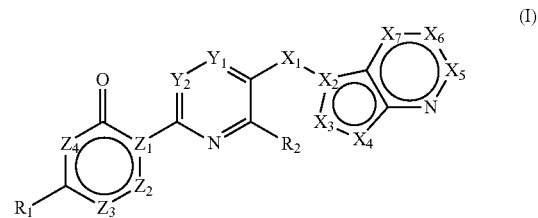

wherein $X_1$ is selected from bond, —$CH_2$—O—, —CH=CH—, —$(CR_3R_4)_m$—, —$N(R_5)$— or —C(O)—$N(R_6)$—;

$X_2$ is selected from C or N;

$X_3$, $X_4$, $X_5$ and $X_7$ are each independently selected from $C(R_7)$, NH or N;

$X_6$ is selected from $C(R_8)$, NH or N provided that at least one N or NH is included in $X_2$, $X_3$, $X_4$, $X_6$, $X_5$ and $X_7$;

$Y_1$ and $Y_2$ are each independently selected from $C(R_9)$ or N;

$Z_1$ is selected from C or N;

$Z_2$ and $Z_3$ are each independently selected from bond, $C(R_{10})$, NH or N, but they cannot both be bonds;

$Z_4$ is selected from $C(R_{11})$ or $N(R_{12})$;

$R_1$ is selected from the group consisting of hydrogen, deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)(=$NR_{13}$)$R_{14}$, —$C_{0-8}$—B(O$R_{15}$)$_2$, —$C_{0-8}$—P(O)(R$_{16}$)$_2$, —$C_{0-8}$—S(O)$_r$R$_{14}$, —$C_{0-8}$—O—R$_{15}$, —$C_{0-8}$—C(O)OR$_{15}$, —$C_{0-8}$—C(O)R$_{16}$, —$C_{0-8}$—O—C(O)R$_{16}$, —$C_{0-8}$—NR$_{17}$R$_{18}$, —$C_{0-8}$—O—C(O)NR$_{17}$R$_{18}$ and —$C_{0-8}$—N(R$_{17}$)—C(O)R$_{16}$, or, $R_1$ and $R_{11}$ or $R_1$ and $R_{12}$, together with the group directly attached thereto, form $C_{3-10}$ cycloalkyl, 3-10 membered heterocyclyl, $C_{5-10}$ aryl or 5-10 membered heteroaryl, and above groups are optionally further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl. $-C_{0-8}-S(O)_rR_{14}$, $-C_{0-8}-O-R_{15}$, $-C_{0-8}-C(O)OR_{15}$, $-C_{0-8}-C(O)R_{16}$, $-C_{0-8}-O-C(O)R_{16}$, $-C_{0-8}-NR_{17}R_{18}$, $-C_{0-8}-C(O)NR_{17}R_{18}$ and $-C_{0-8}-N(R_{17})-C(O)R_{16}$;

$R_2$ is selected from the group consisting of hydrogen, deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, $-C_{0-8}-S(O)(=NR_{13})R_{14}$, $-C_{0-8}-B(OR_{15})_2$, $-C_{0-8}-P(O)(R_{16})_2$, $-C_{0-8}-S(O)_rR_{14}$, $-C_{0-8}-O-R_{15}$, $-C_{0-8}-C(O)OR_{15}$, $-C_{0-8}-C(O)R_{16}$, $-C_{0-8}-O-C(O)R_{16}$, $-C_{0-8}-NR_{17}R_{18}$, $-C_{0-8}-C(O)NR_{17}R_{18}$ and $-C_{0-8}-N(R_{17})-C(O)R_{16}$, and above groups are optionally further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, $-C_{0-8}-S(O)_rR_{14}$, $-C_{0-8}-O-R_{15}$, $-C_{0-8}-C(O)OR_{15}$, $-C_{0-8}-C(O)R_{16}$, $-C_{0-8}-O-C(O)R_{16}$, $-C_{0-8}-NR_{17}R_{18}$, $-C_{0-8}-C(O)NR_{17}R_{18}$ and $-C_{0-8}-N(R_{17})-C(O)R_{16}$;

$R_3$ and $R_4$ are each independently selected from the group consisting of hydrogen, deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, $-C_{0-8}-S(O)(=NR_{13})R_{14}$, $-C_{0-8}-B(OR_{15})_2$, $-C_{0-8}-P(O)(R_{16})_2$, $-C_{0-8}-S(O)_rR_{14}$, $-C_{0-8}-O-R_{15}$, $-C_{0-8}-C(O)OR_{15}$, $-C_{0-8}-C(O)R_{16}$, $-C_{0-8}-O-C(O)R_{16}$, $-C_{0-8}-NR_{17}R_{18}$, $-C_{0-8}-C(O)NR_{17}R_{18}$ and $-C_{0-8}-N(R_{17})-C(O)R_{16}$, or, $R_3$ and $R_4$, together with the carbon atom directly attached thereto, form carbonyl, $C_{3-10}$ cycloalkyl or 3-10 membered heterocyclyl, and above groups are optionally further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, $-C_{0-8}-S(O)_rR_{14}$, $-C_{0-8}-O-R_{15}$, $-C_{0-8}-C(O)OR_{15}$, $-C_{0-8}-C(O)R_{16}$, $-C_{0-8}-O-C(O)R_{16}$, $-C_{0-8}-NR_{17}R_{18}$, $-C_{0-8}-C(O)NR_{17}R_{18}$ and $-C_{0-8}-N(R_{17})-C(O)R_{16}$;

$R_5$, $R_6$ and $R_{12}$ are each independently selected from the group consisting of hydrogen, deuterium, hydroxy, $C_{1-8}$ alkyl, $C_{1-8}$ alkoxy, $C_{2-8}$ alkenyl, $C_{2-8}$ alkynyl, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and $-NR_{21}R_{22}$, and above groups are optionally further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, $-C_{0-8}-S(O)_rR_{14}$, $-C_{0-8}-O-R_{15}$, $-C_{0-8}-C(O)OR_{15}$, $-C_{0-8}-C(O)R_{16}$, $-C_{0-8}-O-C(O)R_{16}$, $-C_{0-8}-NR_{17}R_{18}$, $-C_{0-8}-C(O)NR_{17}R_{18}$ and $-C_{0-8}-N(R_{17})-C(O)R_{16}$;

$R_7$, $R_9$, $R_{10}$ and $R_{11}$ are each independently selected from the group consisting of hydrogen, deuterium, halogen, cyano, nitro, azido. $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, $-C_{0-8}-S(O)(=NR_{13})R_{14}$, $-C_{0-8}-B(OR_{15})_2$, $-C_{0-8}-P(O)(R_{16})_2$, $-C_{0-8}-S(O)_rR_{14}$, $-C_{0-8}-O-R_{15}$, $-C_{0-8}-C(O)OR_{15}$, $-C_{0-8}-C(O)R_{16}$, $-C_{0-8}-O-C(O)R_{16}$, $-C_{0-8}-NR_{17}R_{18}$, $-C_{0-8}-C(O)NR_{17}R_{18}$ and $-C_{0-8}-N(R_{17})-C(O)R_{16}$, above groups are optionally further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, $-C_{0-8}-S(O)_rR_{14}$, $-C_{0-8}-O-R_{15}$, $-C_{0-8}-C(O)OR_{15}$, $-C_{0-8}-C(O)R_{16}$, $-C_{0-8}-O-C(O)R_{16}$, $-C_{0-8}-NR_{17}R_{18}$, $-C_{0-8}-C(O)NR_{17}R_{18}$ and $-C_{0-8}-N(R_{17})-C(O)R_{16}$, and above groups are optionally further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, $-C_{0-8}-S(O)_rR_{14}$, $-C_{0-8}-O-R_{15}$, $-C_{0-8}-C(O)OR_{15}$, $-C_{0-8}-C(O)R_{16}$, $-C_{0-8}-O-C(O)R_{16}$, $-C_{0-8}-NR_{17}R_{18}$, $-C_{0-8}-C(O)NR_{17}R_{18}$ and $-C_{0-8}-N(R_{17})-C(O)R_{16}$;

$R_8$ is selected from the group consisting of hydrogen, deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, $-C_{0-8}-S(O)(=NR_{13})R_{14}$, $-C_{0-8}-B(OR_{15})_2$, $-C_{0-8}-P(O)(R_{16})_2$, $-C_{0-8}-S(O)_rR_{14}$, $-C_{0-8}-O-R_{15}$, $-C_{0-8}-C(O)OR_{15}$, $-C_{0-8}-C(O)R_{16}$, $-C_{0-8}-O-C(O)R_{16}$, $-C_{0-8}-NR_{17}R_{18}$, $-C_{0-8}-C(O)NR_{17}R_{18}$ and $-C_{0-8}-N(R_{17})-C(O)R_{16}$, and above groups are optionally more further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, $-C_{0-8}-S(O)_rR_{14}$, $-C_{0-8}-O-R_{15}$, $-C_{0-8}-C(O)OR_{15}$, $-C_{0-8}-C(O)R_{16}$, $-C_{0-8}-O-C(O)R_{16}$, $-C_{0-8}-NR_{17}R_{18}$, $-C_{0-8}-C(O)NR_{17}R_{18}$ and $-C_{0-8}-N(R_{17})-C(O)R_{16}$, wherein the cycloalkyl, heterocyclyl, aryl and heteroaryl are optionally more further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, $-C_{0-8}-S(O)_rR_{14}$, $-C_{0-8}-O-R_{15}$, $-C_{0-8}-C(O)OR_{15}$, $-C_{0-8}-C(O)R_{16}$, $-C_{0-8}-O-C(O)R_{16}$, $-C_{0-8}-NR_{17}R_{18}$, $-C_{0-8}-C(O)NR_{17}R_{18}$ and $-C_{0-8}-N(R_1)-C(O)R_{16}$;

each $R_{13}$ is independently selected from the group consisting of hydrogen, deuterium, $C_{1-8}$ alkyl, $C_{3-10}$ cycloalkyl$C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, $-C_{0-8}-S(O)_rR_{14}$, $-C_{0-8}-O-R_{15}$, $-C_{0-8}-C(O)OR_{15}$, $-C_{0-8}-C(O)R_{16}$, $-C_{0-8}-O-C(O)R_{16}$, $-C_{0-8}-NR_{17}R_{18}$, $-C_{0-8}-C(O)NR_{17}R_{18}$ and $-C_{0-8}-N(R_{17})-C(O)R_{16}$;

each $R_{14}$ is independently selected from the group consisting of hydrogen, deuterium, hydroxy, $C_{1-8}$ alkyl, $C_{1-8}$ alkoxy, $C_{2-8}$ alkenyl, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and $-NR_{17}R_{18}$, and above groups are optionally further substituted by one or more substituents selected from the group consisting of deuterium, halogen, hydroxy, carbonyl, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —$NR_{17}R_{18}$;

each $R_{15}$ is independently selected from the group consisting of hydrogen, deuterium, $C_{1-8}$ alkyl, $C_{2-8}$ alkenyl, $C_{3-10}$ cycloalkyl, 3-10 membered heterocyclyl, $C_{5-10}$ aryl and 5-10 membered heteroaryl, and above groups are optionally further substituted by one or more substituents selected from the group consisting of deuterium, halogen, hydroxy, carbonyl, cyano, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —$NR_{17}R_{18}$;

each $R_{16}$ is independently selected from the group consisting of hydrogen, deuterium, hydroxy, $C_{1-8}$ alkyl, $C_{1-8}$ alkoxy, $C_{2-8}$ alkenyl, $C_{2-8}$ alkynyl, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —$NR_{17}R_{18}$, and above groups are optionally further substituted by one or more substituents selected from the group consisting of deuterium, halogen, hydroxy, cyano, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —$NR_{17}R_{18}$:

$R_{17}$ and $R_{18}$ are each independently selected from the group consisting of hydrogen, deuterium, hydroxy, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, sulfonyl, methanesulfonyl, isopropylsulfonyl, cyclopropylsulfonyl, p-toluenesulfonyl, amino, monoalkylamino, dialkylamino and $C_{1-8}$ alkanoyl, and above groups are optionally further substituted by one or more substituents selected from the group consisting of deuterium, halogen, hydroxy, $C_{1-8}$ alkyl, $C_{1-8}$ alkoxy. $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, amino, monoalkylamino, dialkylamino and $C_{1-8}$ alkanoyl;

or, $R_{17}$ and $R_{18}$, together with the nitrogen atom directly attached thereto, form 4-10 membered heterocyclyl, and above groups are optionally further substituted by one or more substituents selected from the group consisting of deuterium, halogen, hydroxy, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, amino, monoalkylamino, dialkylamino and $C_{1-8}$ alkanoyl;

each m is independently selected from 0, 1, 2, 3, 4 or 5; and each r is independently 0, 1 or 2.

As a preferred embodiment, in the compound of formula (I), the stereoisomer or pharmaceutically acceptable salt thereof, $R_2$ is selected from the group consisting of hydrogen, deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, —$C_{0-4}$—S(O)(=$NR_{13}$)$R_{14}$, —$C_{0-4}$—B(O$R_{15}$)$_2$, —$C_{0-4}$—P(O)($R_{16}$)$_2$, —$C_{0-4}$—S(O)$_r R_{14}$, —$C_{0-4}$—O—$R_{15}$, —$C_{0-4}$—C(O)O$R_{15}$, —$C_{0-4}$—C(O)$R_{16}$, —$C_{0-4}$—O—C(O)$R_{16}$, —$C_{0-4}$—$NR_{17}R_{18}$, —$C_{0-4}$—C(O)$NR_{17}R_{18}$ and —$C_{0-4}$—N($R_{17}$)—C(O)$R_{16}$, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r R_{14}$, —$C_{0-4}$—O—$R_{15}$, —$C_{0-4}$—C(O)O$R_{15}$, —$C_{0-4}$—C(O)$R_{16}$, —$C_{0-4}$—O—C(O)$R_{16}$, —$C_{0-4}$—$NR_{17}R_{18}$, —$C_{0-4}$—C(O)$NR_{17}R_{18}$ and —$C_{0-4}$—N($R_{17}$)—C(O)$R_{16}$, and $R_{13}$, $R_{14}$, $R_{15}$, $R_{16}$, $R_{17}$, $R_{18}$ and r are defined as above.

As a further preferred embodiment, in the compound of formula (I), the stereoisomer or pharmaceutically acceptable salt thereof. $R_2$ is selected from the group consisting of hydrogen, deuterium, fluorine, chlorine, cyano, nitro, azido, methyl, ethyl, isopropyl, allyl, ethynyl, cyclopropyl, cyclopropylmethyl, oxa-cyclobutyl, aza-cyclopentyl, aza-cyclohexyl, phenyl, diazole, triazole, methanesulfonyl, isopropylsulfonyl, aminosulfonyl, methoxy, ethoxy, isopropoxy, methoxyethyl, ethoxyethyl, hydroxymethyl, hydroxyethyl, cyanomethyl, trifluoromethyl, trideuteriomethyl, difluoromethyl, dideuteriomethyl, methoxycarbonyl, ethoxycarbonyl, acetyl, acetoxy, acetoxymethyl, amino, dimethylamino, aminomethyl, aminocarbonyl, dimethylaminocarbonyl and acetylamino.

As a more further preferred embodiment, in the compound of formula (I), the stereoisomer or pharmaceutically acceptable salt thereof, $R_2$ is selected from the group consisting of hydrogen, deuterium, fluorine, chlorine, cyano, methyl, ethyl, isopropyl, cyclopropyl, cyclopropylmethyl, oxa-cyclobutyl, methoxy, ethoxy, isopropoxy, methoxyethyl, ethoxyethyl, hydroxymethyl, hydroxyethyl, cyanomethyl, trifluoromethyl, trideuteriomethyl, difluoromethyl, dideuteriomethyl, amino and dimethylamino.

As a more further preferred embodiment, in the compound of formula (I), the stereoisomer or pharmaceutically acceptable salt thereof, $R_2$ is selected from the group consisting of hydrogen, deuterium, fluorine, chlorine, cyano, methyl, ethyl, cyclopropyl, cyclopropylmethyl, methoxy, ethoxy, trifluoromethyl, trideuteriomethyl, difluoromethyl, dideuteriomethyl, amino and dimethylamino.

As a further preferred embodiment, in the compound of formula (I), the stereoisomer or pharmaceutically acceptable salt thereof, $X_1$ is —(CR$_3$R$_4$)$_m$—; $R_3$ and $R_4$ are each independently selected from the group consisting of hydrogen, deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, —$C_{0-4}$—S(O)(=$NR_{13}$)$R_{14}$, —$C_{0-4}$—B(O$R_{15}$)$_2$, —$C_{0-4}$—P(O)($R_{16}$)$_2$, —$C_{0-4}$—S(O)$_r R_{14}$, —$C_{0-4}$—O—$R_{15}$, —$C_{0-4}$—C(O)O$R_{15}$, —$C_{0-4}$—C(O)$R_{16}$, —$C_{0-4}$—O—C(O)$R_{16}$, —$C_{0-4}$—$NR_{17}R_{18}$, —$C_{0-8}$—C(O)$NR_{17}R_{18}$ and —$C_{0-4}$—N($R_{17}$)—C(O)$R_{16}$, or, $R_3$ and $R_4$, together with the carbon atom directly attached thereto, form carbonyl, $C_{3-8}$ cycloalkyl or 3-8 membered heterocyclyl, above groups are optionally further substituted by one or more substituents selected from the group consisting of deuterium, halogen, cyano, nitro, azido, $C_{1-8}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r R_{14}$, —$C_{0-4}$—O—$R_{15}$, —$C_{0-4}$—C(O)O$R_{15}$, —$C_{0-4}$—C(O)$R_{16}$, —$C_{0-4}$—O—C(O)$R_{16}$, —$C_{0-4}$—$NR_{17}R_{18}$, —$C_{0-4}$—C(O)$NR_{17}R_{18}$ and —$C_{0-4}$—N($R_{17}$)—C(O)$R_{16}$, and $R_{13}$, $R_{14}$, $R_{15}$, $R_{16}$, $R_{17}$, $R_{18}$, r and m are defined as above.

As a more further preferred embodiment, in the compound of formula (I), the stereoisomer or pharmaceutically acceptable salt thereof, $X_1$ is —C(R$_3$R$_4$)—; $R_3$ and $R_4$ are each independently selected from the group consisting of hydrogen, deuterium, fluorine, chlorine, hydroxy, methyl, trifluoromethyl, trideuteriomethyl, ethyl, isopropyl, cyclopropyl, cyclopropylmethyl, methoxy and methoxyethyl, or, $R_3$ and $R_4$, together with the carbon atom directly attached thereto, form carbonyl, cyclopropyl, cyclobutyl or oxa-cyclobutyl.

As a further preferred embodiment, the compound of formula (I) is a compound with the structure shown as formula (IIa):

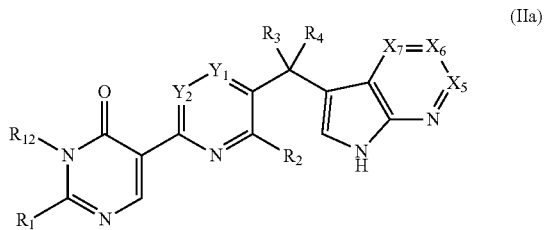

(IIa)

wherein, $R_1$ is selected from the group consisting of hydrogen, deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, —$C_{0-4}$—S(O)(=$NR_{13}$)$R_{14}$, —$C_{0-4}$—B(O$R_{15}$)$_2$, —$C_{0-4}$—P(O)($R_{16}$)$_2$, —$C_{0-4}$—S(O)$_r$$R_{14}$, —$C_{0-4}$—O—$R_{15}$, —$C_{0-4}$—C(O)O$R_{15}$, —$C_{0-4}$—C(O)$R_{16}$, —$C_{0-4}$—O—C(O)$R_{16}$, —$C_{0-4}$—N$R_{17}$$R_{18}$, —$C_{0-4}$—C(O)N$R_{17}$$R_{18}$ and —$C_{0-4}$—N($R_{17}$)—C(O)$R_{16}$, or, $R_1$ and $R_{12}$, together with the group directly attached thereto, form 3-10 membered heterocyclyl or 5-10 membered heteroaryl, and above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$$R_{14}$, —$C_{0-4}$—O—$R_{15}$, —$C_{0-4}$—C(O)O$R_{15}$, —$C_{0-4}$—C(O)$R_{16}$, —$C_{0-4}$—O—C(O)$R_{16}$, —$C_{0-4}$—N$R_{17}$$R_{18}$, —$C_{0-4}$—C(O)N$R_{17}$$R_{18}$ and —$C_{0-4}$—N($R_{17}$)—C(O)$R_{16}$;

$R_2$ is selected from the group consisting of hydrogen, deuterium, fluorine, chlorine, cyano, methyl, ethyl, cyclopropyl, cyclopropylmethyl, methoxy, ethoxy, trifluoromethyl, trideuteriomethyl, difluoromethyl, dideuteriomethyl, amino and dimethylamino;

$R_3$ and $R_4$ are each independently selected from the group consisting of hydrogen, deuterium, fluorine, chlorine, hydroxy, methyl, trifluoromethyl, trideuteriomethyl, ethyl, isopropyl, cyclopropyl, cyclopropylmethyl, methoxy or methoxyethyl, or, $R_3$ and $R_4$, together with the carbon atom directly attached thereto, form carbonyl, cyclopropyl, cyclobutyl or oxa-cyclobutyl;

$R_{12}$ is selected from the group consisting of hydrogen, deuterium, hydroxy, $C_{1-4}$ alkyl, $C_{1-4}$ alkoxy, $C_{2-4}$ alkenyl, $C_{2-4}$ alkynyl, $C_{3-8}$ cycloalkyl, $C_{3-8}$ cycloalkyloxy, 3-8 membered heterocyclyl, 3-8 membered heterocyclyloxy, $C_{5-8}$ aryl, $C_{5-8}$ aryloxy, 5-8 membered heteroaryl, 5-8 membered heteroaryloxy and —N$R_{21}$$R_{22}$, and above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$$R_{14}$, —$C_{0-4}$—O—$R_{15}$, —$C_{0-4}$—C(O)O$R_{15}$, —$C_{0-4}$—C(O)$R_{16}$, —$C_{0-4}$—O—C(O)$R_{16}$, —$C_{0-4}$—N$R_{17}$$R_{18}$, —$C_{0-4}$—C(O)N$R_{17}$$R_{18}$ and —$C_{0-4}$—N($R_{17}$)—C(O)$R_{16}$;

and $X_5$, $X_6$, $X_7$, $Y_1$, $Y_2$, $R_7$, $R_8$, $R_9$, $R_{13}$, $R_{14}$, $R_{15}$, $R_{16}$, $R_{17}$, $R_{18}$ and r are defined as in the compound of formula (I).

As a more further preferred embodiment, in the compound of formula (I), the stereoisomer or pharmaceutically acceptable salt thereof, $X_5$ and $X_7$ are each independently selected from CH or N; $X_6$ is selected from C($R_8$) or N; $Y_1$ and $Y_2$ are each independently selected from CH or N;

$R_1$ is selected from the group consisting of $C_{1-4}$ alkyl, $C_{3-8}$ cycloalkyl, 3-8 membered heterocyclyl, $C_{5-8}$ aryl, 5-8 membered heteroaryl and —$C_{0-4}$—N$R_{17}$$R_{18}$, or, $R_1$ and $R_{12}$, together with the group directly attached thereto, form 3-10 membered heterocyclyl or 5-10 membered heteroaryl, and above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$$R_{14}$, —$C_{0-4}$—O—$R_{15}$, —$C_{0-4}$—C(O)O$R_{15}$, —$C_{0-4}$—C(O)$R_{16}$, —$C_{0-4}$—O—C(O)$R_{16}$, —$C_{0-4}$—N$R_{17}$$R_{18}$, —$C_{0-4}$—C(O)N$R_{17}$$R_{18}$ and —$C_{0-4}$—N($R_{17}$)—C(O)$R_{16}$;

$R_2$ is selected from the group consisting of hydrogen, deuterium, fluorine, chlorine, cyano, methyl, ethyl, cyclopropyl, cyclopropylmethyl, methoxy, ethoxy, trifluoromethyl, trideuteriomethyl, difluoromethyl, dideuteriomethyl, amino and dimethylamino;

$R_3$ and $R_4$ are each independently selected from the group consisting of hydrogen, deuterium, fluorine, chlorine, methyl, trifluoromethyl, trideuteriomethyl, ethyl, isopropyl, cyclopropyl, cyclopropylmethyl, methoxy and methoxyethyl, or, $R_3$ and $R_4$, together with the carbon atom directly attached thereto, form carbonyl, cyclopropyl, cyclobutyl or oxa-cyclobutyl;

and $R_{12}$ is selected from the group consisting of hydrogen, deuterium, methyl, ethyl, cyclopropyl, cyclopropylmethyl, trifluoromethyl, trideuteriomethyl, difluoromethyl, dideuteriomethyl, allyl, cyclobutyl, oxa-cyclobutyl and aza-cyclobutyl.

As a more further preferred embodiment, the compound of formula (I) is a compound with the structure shown as formula (IIIa):

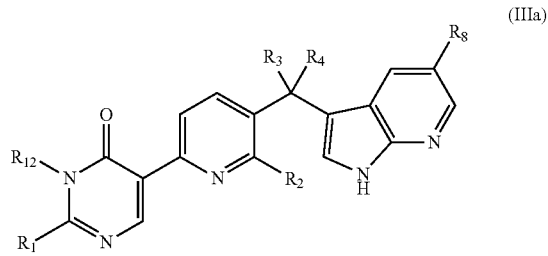

(IIIa)

wherein, $R_1$ is selected from 3-8 membered heterocyclyl, 5-8 membered heteroaryl or —N$R_{17}$$R_{18}$, or, $R_1$ and $R_{12}$, together with the group directly attached thereto, form 3-10 membered heterocyclyl or 5-10 membered heteroaryl, and above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$$R_{14}$, —$C_{0-4}$—O—$R_{15}$, —$C_{0-4}$—C(O)O$R_{15}$, —$C_{0-4}$—C(O)$R_{16}$, —$C_{0-4}$—O—C(O)$R_{16}$, —$C_{0-4}$—N$R_{17}$$R_{18}$, —$C_{0-4}$—C(O)N$R_{17}$$R_{18}$ and —$C_{0-4}$—N($R_{17}$)—C(O)$R_{16}$;

R₂ is selected from the group consisting of hydrogen, deuterium, fluorine, chlorine, cyano, methyl, ethyl, cyclopropyl, cyclopropylmethyl, methoxy, ethoxy, trifluoromethyl, trideuteriomethyl, difluoromethyl, dideuteriomethyl, amino and dimethylamino;

R₃ and R₄ are each independently selected from the group consisting of hydrogen, deuterium, fluorine, chlorine, methyl, trifluoromethyl, trideuteriomethyl, ethyl, isopropyl, cyclopropyl, cyclopropylmethyl, methoxy and methoxyethyl, or, R₃ and R₄, together with the carbon atom directly attached thereto, form carbonyl, cyclopropyl, cyclobutyl or oxa-cyclobutyl;

R₈ is selected from the group consisting of hydrogen, deuterium, halogen, cyano, nitro, azido, C₁₋₄ alkyl, C₂₋₄ alkenyl, C₂₋₄ alkynyl, C₃₋₈ cycloalkyl, 3-8 membered heterocyclyl, C₅₋₈ aryl, 5-8 membered heteroaryl, —C₀₋₄—S(O)(=NR₁₃)R₁₄, —C₀₋₄—B(OR₁₅)₂, —C₀₋₄—P(O)(R₁₆)₂, —C₀₋₄—S(O)ᵣR₁₄, —C₀₋₄—O—R₁₅, —C₀₋₄—C(O)OR₁₅, —C₀₋₄—C(O)R₁₆, —C₀₋₄—O—C(O)R₁₆, —C₀₋₄—NR₁₇R₁₈, —C₀₋₄—C(O)NR₁₇R₁₈ and —C₀₋₄—N(R₁₇)—C(O)R₁₆, and above groups are optionally more further substituted by one or more substituents selected from the group consisting of deuterium, halogen, cyano, nitro, azido, C₁₋₄ alkyl, C₂₋₄ alkenyl, C₂₋₄ alkynyl, C₁₋₄ haloalkyl, C₁₋₄ deuterioalkyl, C₃₋₈ cycloalkyl, 3-8 membered heterocyclyl, C₅₋₈ aryl, 5-8 membered heteroaryl, —C₀₋₄—S(O)ᵣR₁₄, —C₀₋₄—O—R₁₅, —C₀₋₄—C(O)OR₁₅, —C₀₋₄—C(O)R₁₆, —C₀₋₄—O—C(O)R₁₆, —C₀₋₄—NR₁₇R₁₈, —C₀₋₄—C(O)NR₁₇R₁₈ and —C₀₋₄—N(R₁₇)—C(O)R₁₆;

R₁₂ is selected from the group consisting of hydrogen, deuterium, methyl, ethyl, cyclopropyl, cyclopropylmethyl, trifluoromethyl, trideuteriomethyl, difluoromethyl, dideuteriomethyl, allyl, cyclobutyl, oxa-cyclobutyl and aza-cyclobutyl;

and R₁₃, R₁₄, R₁₅, R₁₆, R₁₇, R₁₈ and r are defined as in the compound of formula (I).

As a more further preferred embodiment, in the compound of formula (I), the stereoisomer or pharmaceutically acceptable salt thereof, R₁ is selected from the group consisting of isopropylamino, N,N-isopropylmethylamino, cyclopropylamino, cyclobutylamino, oxa-cyclobutylamino, 1-methoxypropyl-2-amino, 1,1,1-trifluoropropyl-2-amino, aza-cyclobutyl and aza-cyclopentyl, or, R₁ and R₁₂, together with the group attached thereto, form 5-8 membered heterocyclyl, and the 5-8 membered heterocyclyl is optionally further substituted by one or more substituents selected from the group consisting of deuterium, fluorine, chlorine, C₁₋₄ alkyl, C₂₋₄ alkenyl, C₂₋₄ alkynyl, C₁₋₄-haloalkyl, C₃₋₆ cycloalkyl, 3-6 membered heterocyclyl, C₅₋₆ aryl, 5-6 membered heteroaryl and —C₀₋₄—O—R₁₅;

R₁₂ is selected from the group consisting of hydrogen, deuterium, methyl, ethyl, cyclopropyl, cyclopropylmethyl, trifluoromethyl, trideuteriomethyl, difluoromethyl, dideuteriomethyl, allyl, cyclobutyl, oxa-cyclobutyl and aza-cyclobutyl;

and R₈ is selected from the group consisting of hydrogen, deuterium, fluorine, chlorine, hydroxy, cyano, nitro, azido, C₁₋₄ alkyl, allyl, ethynyl, C₃₋₆ cycloalkyl, 3-6 membered heterocyclyl, 5-6 membered heteroaryl, phenyl, methanesulfonyl, isopropylsulfonyl, aminosulfonyl, methoxy, ethoxy, isopropoxy, methoxycarbonyl, ethoxycarbonyl, acetyl, acetoxy, acetoxymethyl, amino, dimethylamino, aminomethyl, aminocarbonyl, dimethylaminocarbonyl and acetylamino, and above groups are optionally more further substituted by one or more substituents selected from the group consisting of deuterium, fluorine, chlorine, hydroxy, cyano, C₁₋₄ alkyl, allyl, ethynyl, cyclopropyl, methoxy and ethoxy.

As a more further preferred embodiment, the compound of formula (I) is a compound with the structure shown as formula (IIb):

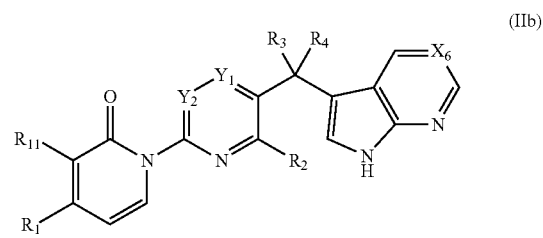

(IIb)

wherein, R₁ is selected from the group consisting of hydrogen, deuterium, halogen, cyano, nitro, azido, C₁₋₄ alkyl, C₂₋₄ alkenyl, C₂₋₄ alkynyl, C₃₋₈ cycloalkyl, 3-8 membered heterocyclyl, C₅₋₈ aryl, 5-8 membered heteroaryl, —C₀₋₄—S(O)(=NR₁₃)R₁₄, —C₀₋₄—B(OR₁₅)₂, —C₀₋₄—P(O)(R₁₆)₂, —C₀₋₄—S(O)ᵣR₁₄, —C₀₋₄—O—R₁₅, —C₀₋₄—C(O)OR₁₅, —C₀₋₄—C(O)R₁₆, —C₀₋₄—O—C(O)R₁₆, —C₀₋₄—NR₁₇R₁₈, —C₀₋₄—C(O)NR₁₇R₁₈ and —C₀₋₄—N(R₁₇)—C(O)R₁₆, or, R₁ and R₁₁, together with the group directly attached thereto, form C₃₋₈ cycloalkyl, 3-8 membered heterocyclyl, C₅₋₈ aryl or 5-8 membered heteroaryl, and above groups are optionally further substituted by one or more substituents selected from the group consisting of deuterium, halogen, cyano, nitro, azido, C₁₋₄ alkyl, C₂₋₄ alkenyl, C₂₋₄ alkynyl, C₁₋₄ haloalkyl, C₃₋₈ cycloalkyl, 3-8 membered heterocyclyl, C₅₋₈ aryl, 5-8 membered heteroaryl, —C₀₋₄—S(O)ᵣR₁₄, —C₀₋₄—O—R₁₅, —C₀₋₄—C(O)OR₁₅, —C₀₋₄—C(O)R₁₆, —C₀₋₄—O—C(O)R₁₆, —C₀₋₄—NR₁₇R₁₈, —C₀₋₄—C(O)NR₁₇R₁₈ and —C₀₋₄—N(R₁₇)—C(O)R₁₆;

R₂ is selected from the group consisting of hydrogen, deuterium, fluorine, chlorine, cyano, methyl, ethyl, cyclopropyl, cyclopropylmethyl, methoxy, ethoxy, trifluoromethyl, trideuteriomethyl, difluoromethyl, dideuteriomethyl, amino and dimethylamino;

R₃ and R₄ are each independently selected from the group consisting of hydrogen, deuterium, fluorine, chlorine, hydroxy, methyl, trifluoromethyl, trideuteriomethyl, ethyl, isopropyl, cyclopropyl, cyclopropylmethyl, methoxy and methoxyethyl, or, R₃ and R₄, together with the carbon atom directly attached thereto, form carbonyl, cyclopropyl, cyclobutyl or oxa-cyclobutyl;

R₁₁ is each independently selected from the group consisting of hydrogen, deuterium, halogen, cyano, nitro, azido, C₁₋₄ alkyl, C₂₋₄ alkenyl, C₂₋₄ alkynyl, C₃₋₈ cycloalkyl, 3-8 membered heterocyclyl, C₅₋₈ aryl, 5-8 membered heteroaryl, —C₀₋₄—S(O)(=NR₁₃)R₁₄, —C₀₋₄—B(OR₁₅)₂, —C₀₋₄—P(O)(R₁₆)₂, —C₀₋₄—S(O)ᵣR₁₄, —C₀₋₄—O—R₁₅, —C₀₋₄—C(O)OR₁₅, —C₀₋₄—C(O)R₁₆, —C₀₋₄—O—C(O)R₁₆, —C₀₋₄—NR₁₇R₁₈, —C₀₋₄—C(O)NR₁₇R₁₈ and —C₀₋₄—N(R₁₇)—C(O)R₁₆, and above groups are optionally further substituted by one or more substituents selected from the group consisting of deuterium, halogen, cyano, nitro, azido, C₁₋₄ alkyl, C₂₋₄ alkenyl, C₂₋₄ alkynyl, C₁₋₄ haloalkyl, C₃₋₈ cycloalkyl, 3-8 membered heterocyclyl, C₅₋₈ aryl, 5-8 membered heteroaryl, —C₀₋₄—S(O)ᵣR₁₄, —C₀₋₄—O—R₁₅, —C₀₋₄—C(O)OR₁₅, —C₀₋₄—C(O)R₁₆, —C₀₋₄—O—C(O)R₁₆, —C₀₋₄—NR₁₇R₁₈, —C₀₋₄—C(O)NR₁₇R₁₈ and —C₀₋₄—N(R₁₇)—C(O)R₁₆;

and $X_6$, $Y_1$, $Y_2$, $R_8$, $R_9$, $R_{13}$, $R_{14}$, $R_{15}$, $R_{16}$, $R_{17}$, $R_{18}$ and r are defined as in the compound of formula (I).

As a more further preferred embodiment, in the compound of formula (I), the stereoisomer or pharmaceutically acceptable salt thereof, $Y_1$ and $Y_2$ are each independently selected from CH or N;

and $R_1$ and $R_{11}$, together with the group directly attached thereto, form $C_{3-6}$ cycloalkyl, 3-6 membered heterocyclyl, $C_{5-6}$ aryl or 5-6 membered heteroaryl, and above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$$R_{14}$, —$C_{0-4}$—O—$R_{15}$, —$C_{0-4}$—C(O)O$R_{15}$, —$C_{0-4}$—C(O)$R_{16}$, —$C_{0-4}$—O—C(O)$R_{16}$, —$C_{0-4}$—N$R_{17}$$R_{18}$, —$C_{0-4}$—C(O)N$R_{17}$$R_{18}$ and —$C_{0-4}$—N($R_{17}$)—C(O)$R_{16}$.

As a further preferred embodiment, the compound of formula (I) is a compound with the structure shown as formula (IIIb):

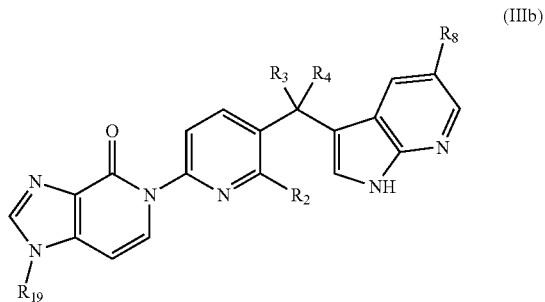

(IIIb)

wherein, $R_2$ is selected from the group consisting of hydrogen, deuterium, fluorine, chlorine, cyano, methyl, ethyl, cyclopropyl, cyclopropylmethyl, methoxy, ethoxy, trifluoromethyl, trideuteriomethyl, difluoromethyl, dideuteriomethyl, amino and dimethylamino;

$R_3$ and $R_4$ are each independently selected from the group consisting of hydrogen, deuterium, fluorine, chlorine, hydroxy, methyl, trifluoromethyl, trideuteriomethyl, ethyl, isopropyl, cyclopropyl, cyclopropylmethyl, methoxy and methoxyethyl, or, $R_3$ and $R_4$, together with the carbon atom directly attached thereto, form carbonyl, cyclopropyl, cyclobutyl or oxa-cyclobutyl;

$R_8$ is selected from the group consisting of hydrogen, deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, —$C_{0-4}$—S(O)(=N$R_{13}$)$R_{14}$, —$C_{0-4}$—B(O$R_{15}$)$_2$, $C_{0-4}$—P(O)($R_{16}$)$_2$, —$C_{0-4}$—S(O)$R_{14}$, —$C_{0-4}$—O—$R_{15}$, —$C_{0-4}$—C(O)O$R_{15}$, —$C_{0-4}$—C(O)$R_{16}$, —$C_{0-4}$—O—C(O)$R_{16}$, —$C_{0-4}$—N$R_{17}$$R_{18}$, —$C_{0-4}$—C(O)N$R_{17}$$R_{18}$ and —$C_{0-8}$—N($R_{17}$)—C(O)$R_{16}$, and above groups are optionally more further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aril, 5-8 membered heteroaryl, —$C_{0-4}$—S(O)$_r$$R_{14}$, —$C_{0-4}$—O—$R_{15}$, —$C_{0-4}$—C(O)O$R_{15}$, —$C_{0-4}$—C(O)$R_{16}$, —$C_{0-4}$—O—C(O)$R_{16}$, —$C_{0-4}$—N$R_{17}$$R_{18}$, —$C_{0-4}$—C(O)N$R_{17}$$R_{18}$ and —$C_{0-4}$—N($R_{17}$)—C(O)$R_{16}$;

$R_{19}$ is selected from the group consisting of hydrogen, deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$$R_{14}$, —$C_{0-4}$—O—$R_{15}$, —$C_{0-4}$—C(O)O$R_{15}$, —$C_{0-4}$—C(O)$R_{16}$, —$C_{0-4}$—O—C(O)$R_{16}$, —$C_{0-4}$—N$R_{17}$$R_{18}$, —$C_{0-4}$—C(O)N$R_{17}$$R_{18}$ and —$C_{0-4}$—N($R_{17}$)—C(O)$R_{16}$;

and $R_{13}$, $R_{14}$, $R_{15}$, $R_{16}$, $R_{17}$, $R_{18}$ and r are defined as in the compound of formula (I).

As a more further preferred embodiment, in the compound of formula (I), the stereoisomer or pharmaceutically acceptable salt thereof, $R_2$ is selected from the group consisting of hydrogen, deuterium, fluorine, chlorine, cyano, methyl, cyclopropyl, cyclopropylmethyl, trifluoromethyl, difluoromethyl, trideuteriomethyl and dideuteriomethyl:

$R_3$ and $R_4$ are each independently selected from the group consisting of hydrogen, deuterium, fluorine, chlorine, hydroxy, methyl, cyclopropyl and cyclopropylmethyl, or, $R_3$ and $R_4$, together with the carbon atom directly attached thereto, form carbonyl, cyclopropyl, cyclobutyl or oxa-cyclobutyl;

and $R_8$ is selected from the group consisting of hydrogen, deuterium, fluorine, chlorine, hydroxy, cyano, methyl, ethyl, cyclopropyl, cyclopropylmethyl, methoxy, ethoxy, trifluoromethyl, trideuteriomethyl, difluoromethyl, dideuteriomethyl, amino and dimethylamino.

As the most preferred embodiment, the compound of formula (I), the stereoisomer or pharmaceutically acceptable salt thereof includes, but is not limited to, the following compounds:

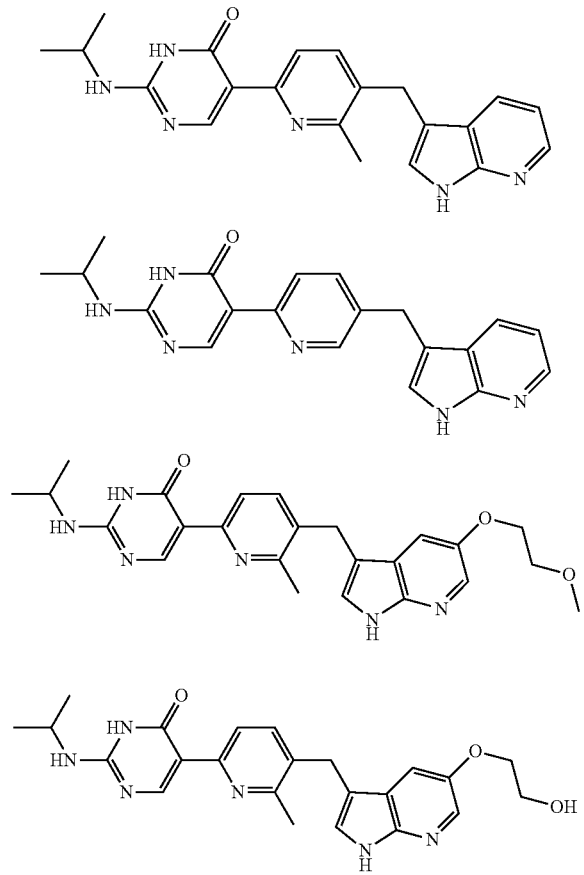

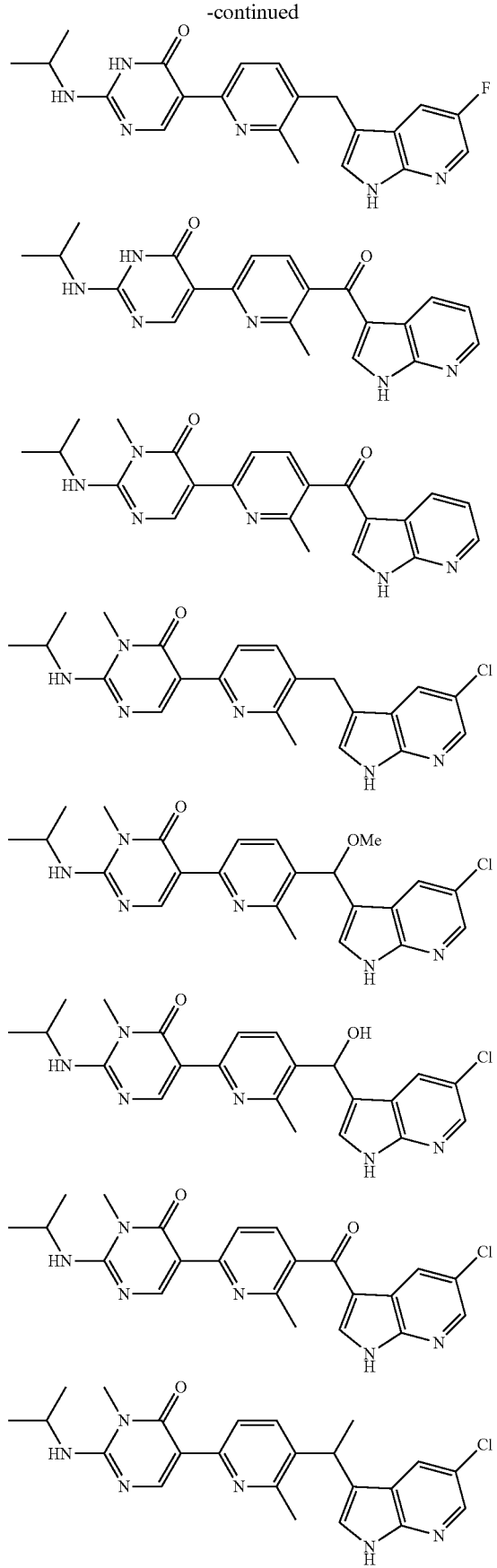
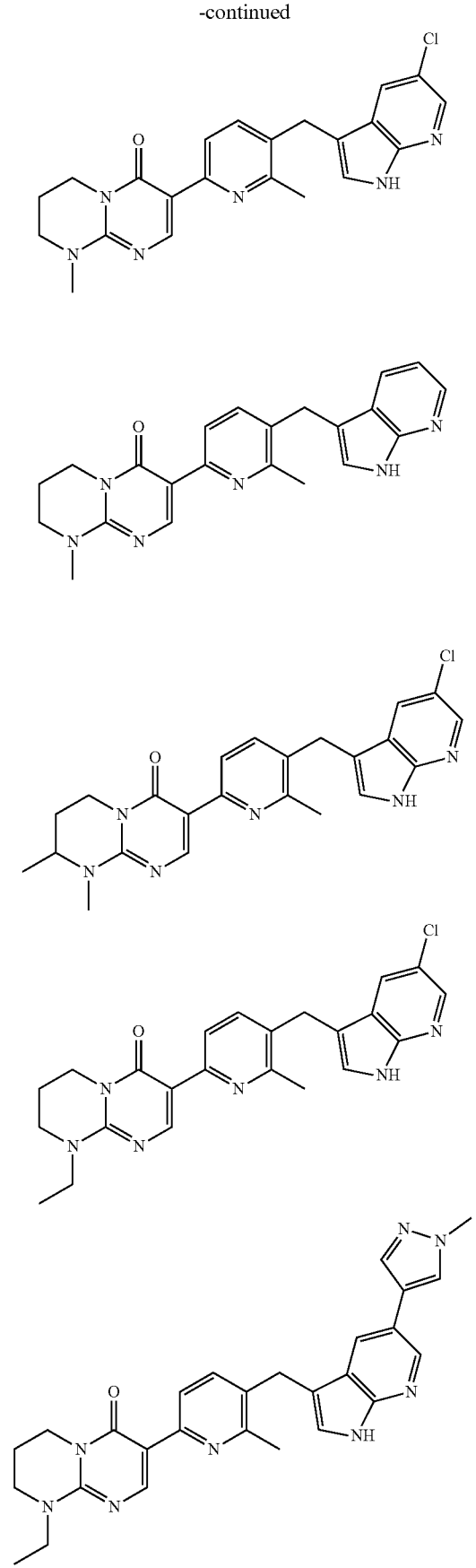

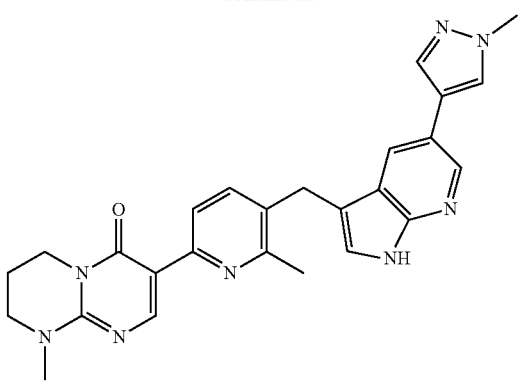
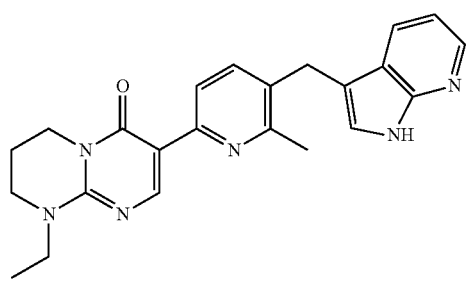
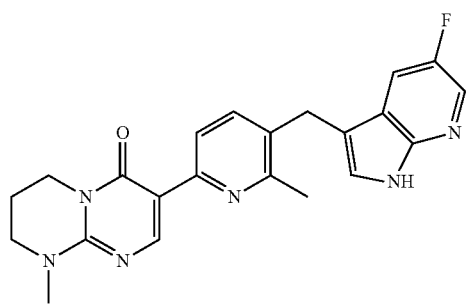
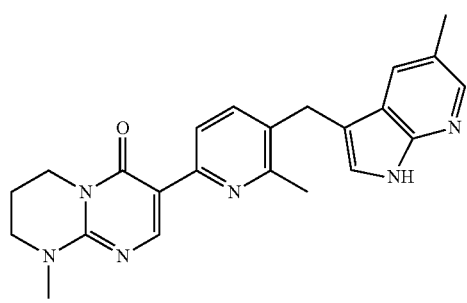
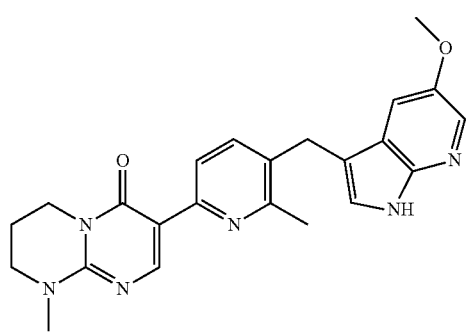
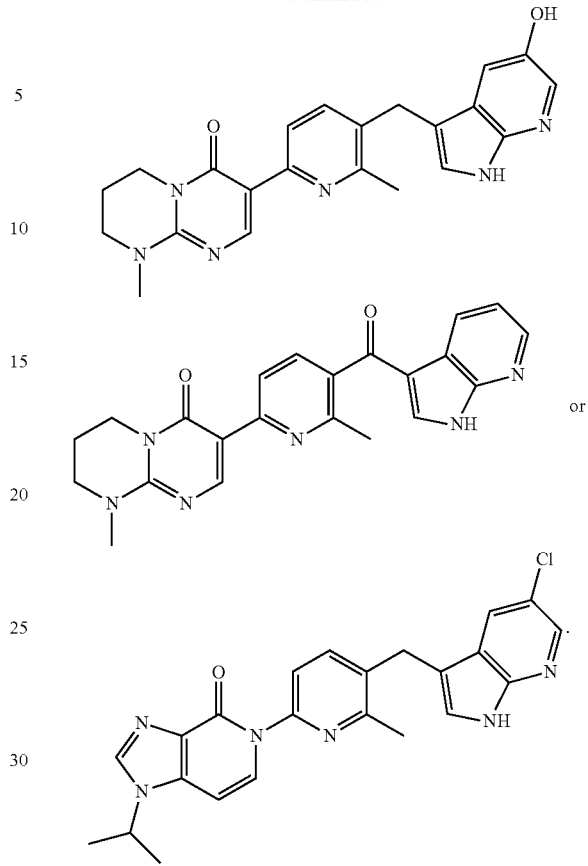
The second aspect of the present invention provides a process for preparing the above compound of formula (I), the stereoisomer or pharmaceutically acceptable salt thereof, comprising the following step:
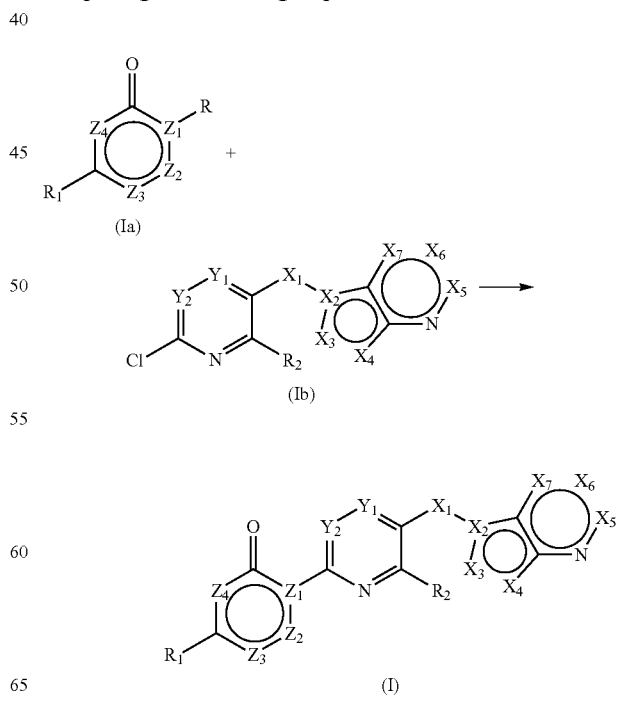

wherein, when $Z_1$ is C, R is

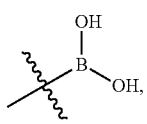

and when $Z_1$ is N, R is hydrogen;
optionally, the compound of formula (I) is obtained through further reactions according to different substituents;
and $X_1$, $X_2$, $X_3$, $X_4$, $X_5$, $X_6$, $X_7$, $Y_1$, $Y_2$, $Z_1$, $Z_2$, $Z_3$, $Z_4$, $R_1$, $R_2$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, m and r are defined as in the compound of formula (I).

The second aspect of the present invention provides a process for preparing the above compound of formula (I), the stereoisomer or pharmaceutically acceptable salt thereof, comprising the following synthesis steps when $X_1$ is —C($R_3R_4$)—:

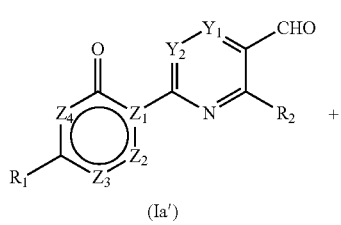
(Ia')

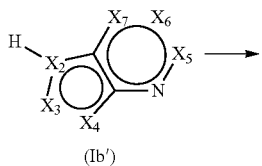
(Ib')

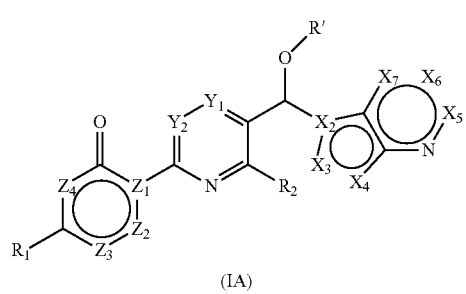
(IA)

wherein, R' is selected from hydrogen or $C_{1-8}$ alkyl;
optionally, the compound of formula (I) is obtained through further reactions according to different substituents;
and $X_1$, $X_2$, $X_3$, $X_4$, $X_5$, $X_6$, $X_7$, $Y_1$, $Y_2$, $Z_1$, $Z_2$, $Z_3$, $Z_4$, $R_1$, $R_2$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, m and r are defined as in the compound of formula (I).

The third aspect of the present invention provides a process for preparing the above compound of formula (I), the stereoisomer or pharmaceutically acceptable salt thereof, comprising the following synthesis steps when $X_1$ is —C($R_3R_4$)— and $R_3$ and $R_4$ are each independently hydrogen:

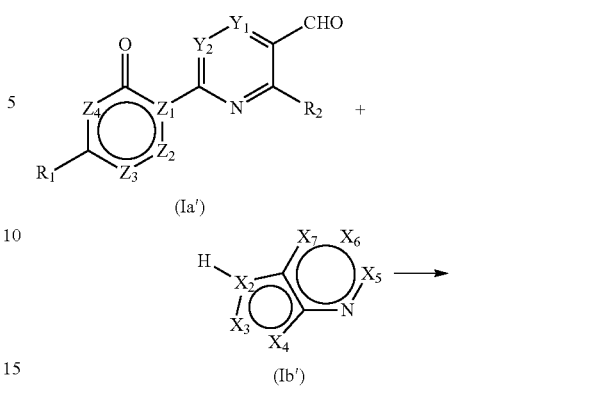

comprising the following synthesis steps when $X_1$ is —C($R_3R_4$)—, $R_3$ is hydrogen, and $R_4$ is a non-hydrogen substituent:

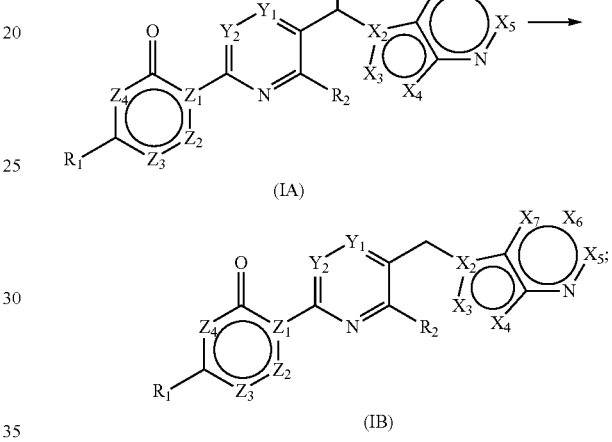

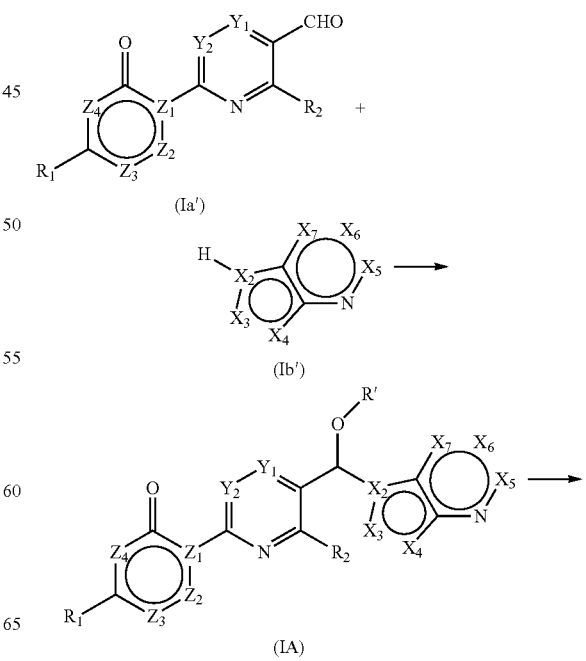

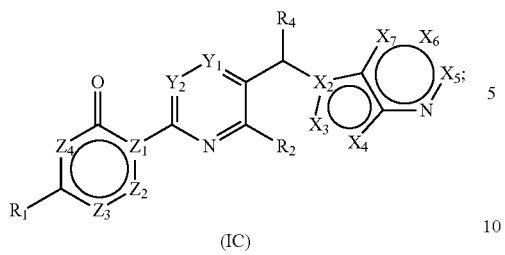

(IC)

comprising the following synthesis steps when $X_1$ is —C($R_3R_4$)—, and, $R_3$ and $R_4$, together with the carbon atom directly attached thereto, form carbonyl:

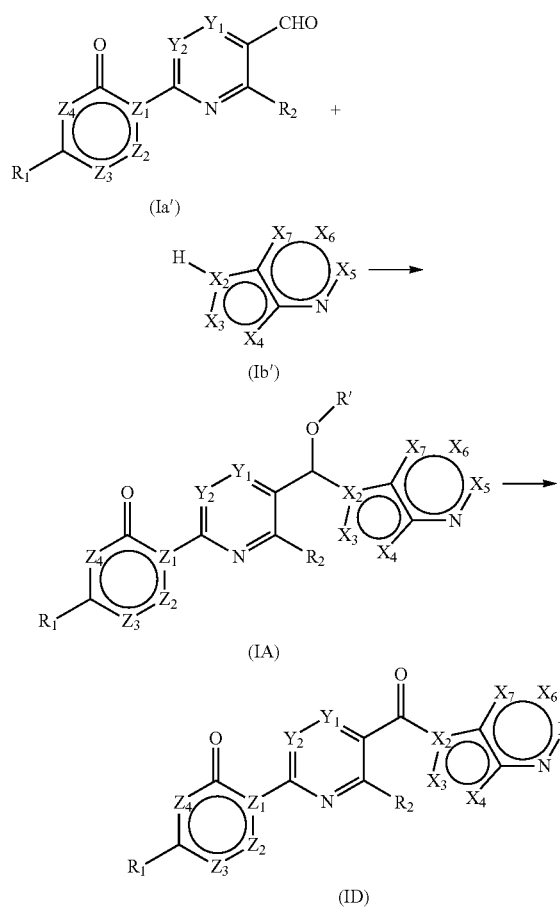

comprising the following synthesis steps when $X_1$ is —C($R_3R_4$)—, and $R_3$ and $R_4$ are each independently a non-hydrogen substituent:

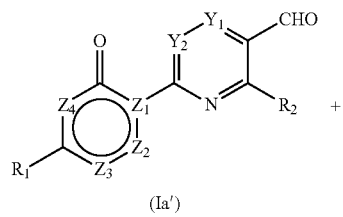

(Ia')

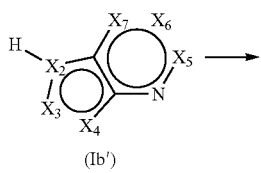

(Ib')

(IA)

(ID)

(IE)

wherein, R' is selected from hydrogen or $C_{1-8}$ alkyl:

optionally, then the compound of formula (I) is obtained through a further reaction in each of above preparing processes according to different substituents;

and $X_1$, $X_2$, $X_3$, $X_4$, $X_5$, $X_6$, $X_7$, $Y_1$, $Y_2$, $Z_1$, $Z_2$, $Z_3$, $Z_4$, $R_1$, $R_2$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, m and r are defined as in the compound of formula (I).

The fourth aspect of the present invention provides a process for preparing the compound of formula (I), the stereoisomer or pharmaceutically acceptable salt thereof, and the compound of formula (I) is a compound with the structure shown as formula (IIa), and is prepared by the following step:

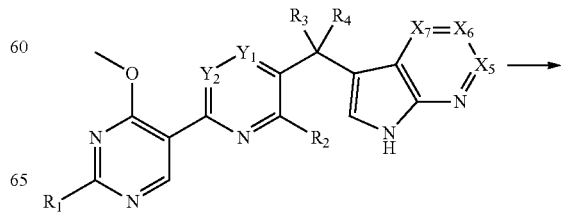

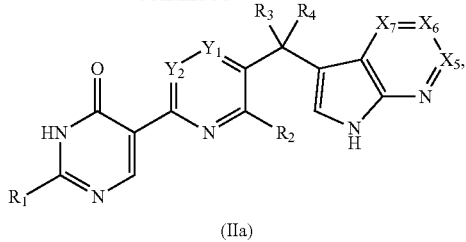

(IIa)

wherein, $R_1$ is selected from the group consisting of hydrogen, deuterium, halogen, cyano, nitro, azido, $C_{1-4}$ alkyl, $C_{2-4}$ alkenyl, $C_{2-4}$ alkynyl $C_{3-8}$ cycloalkyl, 3-8 membered heterocyclyl, $C_{5-8}$ aryl, 5-8 membered heteroaryl, —$C_{0-4}$—S(O)(=$NR_{13}$)$R_{14}$, —$C_{0-4}$—B(O$R_{15}$)$_2$, —$C_{0-4}$—P(O)($R_{16}$)$_2$, —$C_{0-4}$—S(O)$_r R_{14}$, —$C_{0-4}$—O—$R_{15}$, —$C_{0-4}$—C(O)O$R_{15}$, —$C_{0-4}$—C(O)$R_{16}$, —$C_{0-4}$—O—C(O)$R_{16}$, —$C_{0-4}$—N$R_{17}R_{18}$, —$C_{0-4}$—C(O)N$R_{17}R_{18}$ and —$C_{0-4}$—N($R_{17}$)—C(O)$R_{16}$, and above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r R_{14}$, —$C_{0-4}$—O—$R_{15}$, —$C_{0-4}$—C(O)O$R_{15}$, —$C_{0-4}$—C(O)$R_{16}$, —$C_{0-4}$—O—C(O)$R_{16}$, —$C_{0-4}$—N$R_{17}R_{18}$, —$C_{0-4}$—C(O)N$R_{17}R_{18}$ and —$C_{0-4}$—N($R_{17}$)—C(O)$R_{16}$;

or,

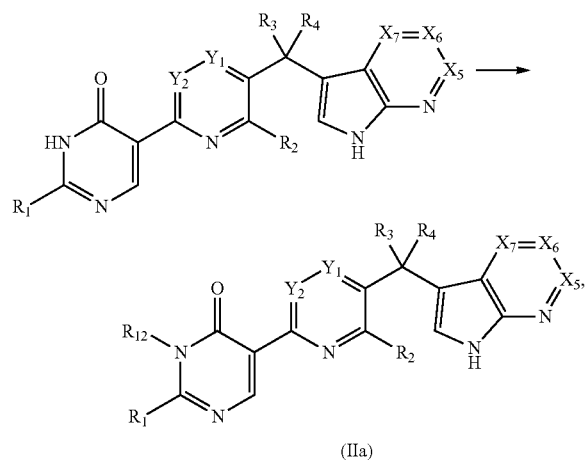

(IIa)

wherein, $R_1$ is selected from the group consisting of hydrogen, deuterium, halogen, cyano, nitro, azido, $C_{1-4}$ alkyl, $C_{2-4}$ alkenyl, $C_{0-4}$ alkynyl, $C_{3-8}$ cycloalkyl, 3-8 membered heterocyclyl, $C_{5-8}$ aryl, 5-8 membered heteroaryl, —$C_{0-4}$—S(O)(=$NR_{13}$)$R_{14}$, —$C_{0-4}$—B(O$R_{15}$)$_2$, —$C_{0-4}$—P(O)($R_{16}$)$_2$, —$C_{0-4}$—S(O)$_r R_{14}$, —$C_{0-4}$—O—$R_{15}$, —$C_{0-4}$—C(O)O$R_{15}$, —$C_{0-4}$—C(O)$R_{16}$, —$C_{0-4}$—O—C(O)$R_{16}$, —$C_{0-4}$—N$R_{17}R_{18}$, —$C_{0-4}$—C(O)N$R_{17}R_{18}$ and —$C_{0-4}$—N($R_{17}$)—C(O)$R_{16}$, and above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r R_{14}$, —$C_{0-4}$—O—$R_{15}$, —$C_{0-4}$—C(O)O$R_{15}$, —$C_{0-4}$—C(O)$R_{16}$, —$C_{0-4}$—O—C(O)$R_{16}$, —$C_{0-4}$—N$R_{17}R_{18}$, —$C_{0-4}$—C(O)N$R_{17}R_{18}$ and —$C_{0-4}$—N($R_{17}$)—C(O)$R_{16}$;

and $R_{12}$ is selected from the group consisting of deuterium, hydroxy, $C_{1-4}$ alkyl, $C_{1-4}$ alkoxy, $C_{2-4}$ alkenyl, $C_{2-4}$ alkynyl, $C_{3-8}$ cycloalkyl, $C_{3-8}$ cycloalkyloxy, 3-8 membered heterocyclyl, 3-8 membered heterocyclyloxy, $C_{5-8}$ aryl, $C_{5-8}$ aryloxy, 5-8 membered heteroaryl, 5-8 membered heteroaryloxy and —N$R_{21}R_{22}$, and above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r R_{14}$, —$C_{0-4}$—O—$R_{15}$, —$C_{0-4}$—C(O)O$R_{15}$, —$C_{0-4}$—C(O)$R_{16}$, —$C_{0-4}$—O—C(O)$R_{16}$, —$C_{0-4}$—N$R_{17}R_{18}$, —$C_{0-4}$—C(O)N$R_{17}R_{18}$ and —$C_{0-4}$—N($R_{17}$)—C(O)$R_{16}$;

or,

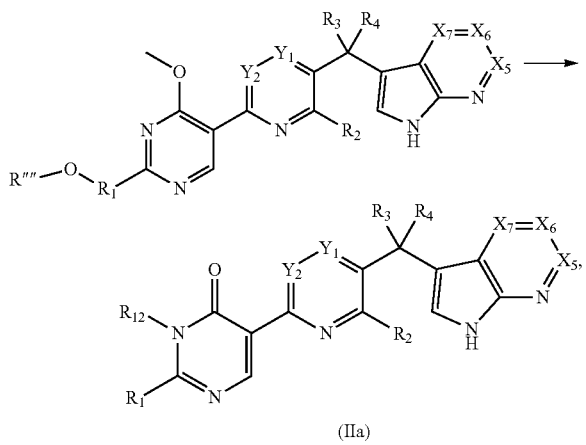

(IIa)

wherein, R'' is selected from hydrogen or a hydroxy protecting group, and preferably, the protecting group is selected from the group consisting of tert-butyldimethylsilyl, trimethylsilyl, isopropyldimethylsilyl, triethylsilyl, triisopropylsilyl, phenyldimethylsilyl, tert-butyldiphenylsilyl, methoxymethyl, P-methoxybenzyl, pivaloyl, tetrahydropyranyl and $C_{1-4}$ alkyl;

$R_1$ and $R_{12}$, together with the group directly attached thereto, form 3-10 membered heterocyclyl or 5-10 membered heteroaryl, and above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r R_{14}$, —$C_{0-4}$—O—$R_{15}$, —$C_{0-4}$—C(O)O$R_{15}$, —$C_{0-4}$—C(O)$R_{16}$, —$C_{0-4}$—O—C(O)$R_{16}$, —$C_{0-4}$—N$R_{17}R_{18}$, —$C_{0-4}$—C(O)N$R_{17}R_{18}$ and —$C_{0-4}$—N($R_{17}$)—C(O)$R_{16}$:

and $X_5$, $X_6$, $X_7$, $Y_1$, $Y_2$, $R_2$, $R_3$, $R_4$, $R_7$, $R_8$, $R_9$, $R_{13}$, $R_{14}$, $R_{15}$, $R_{16}$, $R_{17}$, $R_{18}$ and r are defined as in the compound of formula (I).

The fifth aspect of the present invention provides a pharmaceutical composition, comprising the above compound of formula (I), the stereoisomer or pharmaceutically acceptable salt thereof and a pharmaceutically acceptable carrier.

The sixth aspect of the present invention provides a use of the above compound of formula (I), the stereoisomer or pharmaceutically acceptable salt thereof or the aforementioned pharmaceutical composition in the preparation of medicament for treating cancer, tumor, autoimmune disease, metabolic disease or metastatic disease.

The seventh aspect of the present invention provides a use of the above compound of formula (I), the stereoisomer or pharmaceutically acceptable salt thereof or the aforementioned pharmaceutical composition in the preparation of medicament for treating ovarian cancer, pancreatic cancer, prostate cancer, lung cancer, breast cancer, renal carcinoma, liver cancer, cervical cancer, osseous metastatic cancer, papillary thyroid cancer, non-small cell lung cancer, colon cancer, gastrointestinal stromal tumor, solid tumor, melanoma, mesothelioma, glioblastoma, osteosarcoma, multiple myeloma, hyperproliferative disease, metabolic disease, neurodegenerative disease, primary tumor site metastasis, myeloproliferative disease, leukemia, rheumatic arthritis, rheumatoid arthritis, osteoarthritis, multiple sclerosis, autoimmune nephritis, lupus, Crohn's disease, asthma, chronic obstructive pulmonary disease, osteoporosis, hypereosinophilic syndrome, mastocytosis or mast cell leukemia.

As a preferred embodiment, the present invention provides uses of the above compound of formula (I), the stereoisomer or pharmaceutically acceptable salt thereof or the aforementioned pharmaceutical composition in the preparation of medicament for treating ovarian cancer, pancreatic cancer, prostate cancer, breast cancer, cervical cancer, glioblastoma, multiple myeloma, metabolic disease, neurodegenerative disease, primary tumor site metastasis or osseous metastatic cancer.

The eighth aspect of the present invention provides the above compound of formula (I), the stereoisomer or pharmaceutically acceptable salt thereof or the aforementioned pharmaceutical composition for use as a medicament for treating cancer, tumor, autoimmune disease, metabolic disease or metastatic disease.

The ninth aspect of the present invention provides the compound of formula (I), the above stereoisomer or pharmaceutically acceptable salt thereof or the aforementioned pharmaceutical composition for use as a medicament for treating ovarian cancer, pancreatic cancer, prostate cancer, lung cancer, breast cancer, renal carcinoma, liver cancer, cervical cancer, osseous metastatic cancer, papillary thyroid cancer, non-small cell lung cancer, colon cancer, gastrointestinal stromal tumor, solid tumor, melanoma, mesothelioma, glioblastoma, osteosarcoma, multiple myeloma, hyperproliferative disease, metabolic disease, neurodegenerative disease, primary tumor site metastasis, myeloproliferative disease, leukemia, rheumatic arthritis, rheumatoid arthritis, osteoarthritis, multiple sclerosis, autoimmune nephritis, lupus, Crohn's disease, asthma, chronic obstructive pulmonary disease, osteoporosis, hypereosinophilic syndrome, mastocytosis or mast cell leukemia:

and as a preferred embodiment, the present invention provides the above compound of formula (I), the stereoisomer or pharmaceutically acceptable salt thereof or the aforementioned pharmaceutical composition for use as a medicament for treating ovarian cancer, pancreatic cancer, prostate cancer, breast cancer, cervical cancer, glioblastoma, multiple myeloma, metabolic disease, neurodegenerative disease, primary tumor site metastasis or osseous metastatic cancer.

The tenth aspect of the present invention provides a method for treating cancer, tumor, autoimmune disease, metabolic disease or metastatic disease, comprising administering the above compound of formula (I), the stereoisomer or pharmaceutically acceptable salt thereof or the aforementioned pharmaceutical composition to a patient.

The eleventh aspect of the present invention provides a method for treating ovarian cancer, pancreatic cancer, prostate cancer, lung cancer, breast cancer, renal carcinoma, liver cancer, cervical cancer, osseous metastatic cancer, papillary thyroid cancer, non-small cell lung cancer, colon cancer, gastrointestinal stromal tumor, solid tumor, melanoma, mesothelioma, glioblastoma, osteosarcoma, multiple myeloma, hyperproliferative disease, metabolic disease, neurodegenerative disease, primary tumor site metastasis, myeloproliferative disease, leukemia, rheumatic arthritis, rheumatoid arthritis, osteoarthritis, multiple sclerosis, autoimmune nephritis, lupus, Crohn's disease, asthma, chronic obstructive pulmonary disease, osteoporosis, hypereosinophilic syndrome, mastocytosis or mast cell leukemia, comprising administering the above compound of formula (I), the stereoisomer or pharmaceutically acceptable salt thereof or the aforementioned pharmaceutical composition to a patient.

DETAILED DESCRIPTION OF EMBODIMENTS

After an extensive and intensive research, the inventors of the present invention develop an azaaryl derivative with the structure of formula (I), a preparation method therefor and a pharmaceutical use thereof for the first time. With a strong inhibitory effect on the activity of CSF-1R kinase, the series of compounds of the present invention can be widely applied in the preparation of drugs for treating cancer, tumor, autoimmune disease, metabolic disease or metastatic disease, particularly for treating ovarian cancer, pancreatic cancer, prostate cancer, breast cancer, cervical cancer, glioblastoma, multiple myeloma, metabolic disease, neurodegenerative disease, primary tumor site metastasis or osseous metastatic cancer, and are expected to be developed into a new generation of CSF-1R inhibitor drugs. The present invention is achieved on this basis.

Detailed description: unless otherwise stated, the following terms used in the specification and claims have the following meanings.

"Alkyl" refers to linear or branched saturated aliphatic alkyl groups, for example, "$C_{1-8}$ alkyl" means a linear or branched alkyl having 1 to 8 carbon atoms, including but not limited to methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl or various branched isomers thereof, etc.

Alkyl can be optionally substituted or unsubstituted, and when it is substituted, the substituent is preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, $—C_{0-8}—S(O)_rR_{14}$, $—C_{0-8}—O—R_{15}$, $—C_{0-8}—C(O)OR_{15}$, $—C_{0-8}—C(O)R_{16}$, $—C_{0-8}—O—C(O)R_{16}$, $—C_{0-8}—NR_{17}R_{18}$, $—C_{0-8}—C(O)NR_{17}R_{18}$ and $—C_{0-8}—N(R_{17})—C(O)R_{16}$.

"Cycloalkyl" refers to monocyclic or polycyclic hydrocarbon substituents that are saturated or partially unsaturated, for example, "$C_{3-10}$ cycloalkyl" means a cycloalkyl containing 3 to 10 carbon atoms, which may be monocyclic cycloalkyl and polycyclic cycloalkyl, wherein, monocyclic cycloalkyl includes but is not limited to cyclopropyl, cyclobutyl, cyclopentyl, cyclopentenyl, cyclohexyl, cyclohexenyl, cyclohexadienyl, cycloheptyl, cycloheptatrienyl, cyclooctyl, etc.

Polycyclic cycloalkyl includes spirocycloalkyl, fused cycloalkyl and bridged cycloalkyl. "Spirocycloalkyl" refers to a polycyclic group in which a carbon atom (called spiro-atom) is shared among monocyclic rings, wherein those rings may contain one or more double bonds, but none of them has a fully conjugated π-electron system. According to the number of the spiro-atoms shared among the rings, the spirocycloalkyl may be monospirocycloalkyl, bispirocycloalkyl or polyspirocycloalkyl, including but not limited to:

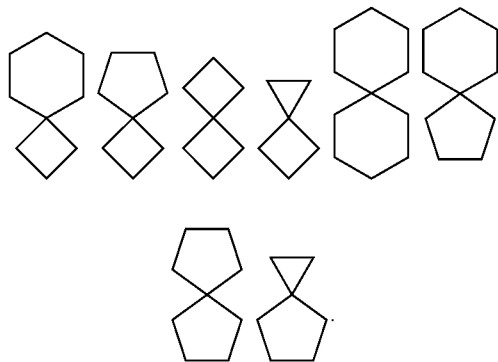

"Fused cycloalkyl" refers to an all-carbon polycyclic group in which each ring share a pair of adjacent carbon atoms with the other rings in the system, wherein one or more of the rings may contain one or more double bonds, but none of them has a fully conjugated π-electron system. According to the number of formed rings, the fused cycloalkyl may be bicyclic, tricyclic, tetracyclic or polycyclic, including but not limited to:

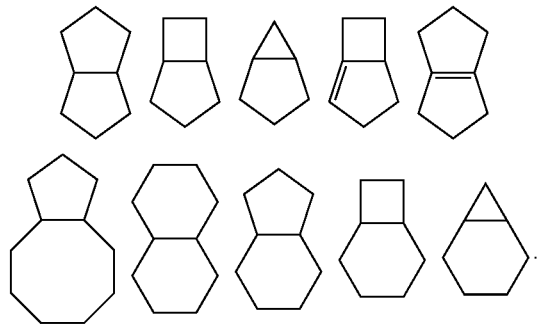

"Bridged cycloalklyl" refers to an all-carbon polycyclic group in which any two rings share two carbon atoms that are not directly connected to each other, wherein these rings may contain one or more double bonds, but none of them has a fully conjugated π-electron system. According to the number of formed rings, the bridged cycloalkyl may be bicyclic, tricyclic, tetracyclic or polycyclic, including but not limited to:

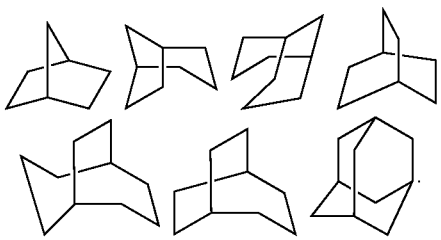

The cycloalkyl ring can be fused to an aryl, heteroaryl or heterocycloalkyl ring, wherein the ring attached to the parent structure is cycloalkyl, which includes but is not limited to indanyl, tetrahydronaphthyl, benzocycloheptyl, etc.

Cycloalkyl may be optionally substituted or unsubstituted, and when it is substituted, the substituent is preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$R$_{14}$, —$C_{0-8}$—O—R$_{15}$, —$C_{0-8}$—C(O)OR$_{15}$, —$C_{0-8}$—C(O)R$_{16}$, —$C_{0-8}$—O—C(O)R$_{16}$, —$C_{0-8}$—NR$_{17}$R$_{18}$, —$C_{0-8}$—C(O)NR$_{17}$R$_{18}$ and —$C_{0-8}$—N(R$_{17}$)—C(O)R$_{16}$.

"Heterocyclyl" refers to a monocyclic or polycyclic hydrocarbon substituent that is saturated or partially unsaturated, wherein one or more of the ring atoms are heteroatoms selected from nitrogen, oxygen or S(O)$_r$ (wherein r is an integer of 0, 1 or 2), excluding ring portions of —O—O—, —O—S— or —S—S—, and the remaining ring atoms are carbon atoms. For example, "5-10 membered heterocyclyl" refers to a cyclic group containing 5 to 10 ring atoms, and "3-10 membered heterocyclyl" means a cyclic group containing 3 to 10 ring atoms.

Monocyclic heterocyclyl includes but is not limited to pyrrolidinyl, piperidinyl, piperazinyl, morpholinyl, thiomorpholinyl, homopiperazinyl, etc.

Polycyclic heterocyclyl includes spiroheterocyclyl, fused heterocyclyl, and bridged heterocyclyl. "Spiroheterocyclyl" refers to a polycyclic heterocyclyl group in which an atom (called spiro-atom) is shared among monocyclic rings, wherein one or more ring atoms are heteroatoms selected from nitrogen, oxygen or S(O)$_r$ (wherein r is an integer of 0, 1 or 2), and the remaining ring atoms are carbon atoms. These rings may contain one or more double bonds, but none of them has a fully conjugated π-electron system. According to the number of spiro-atoms shared among the rings, spiroheterocyclyl may be monospiroheterocyclyl, bispiroheterocyclyl or polyspiroheterocyclyl. Spiroheterocyclyl includes but is not limited to:

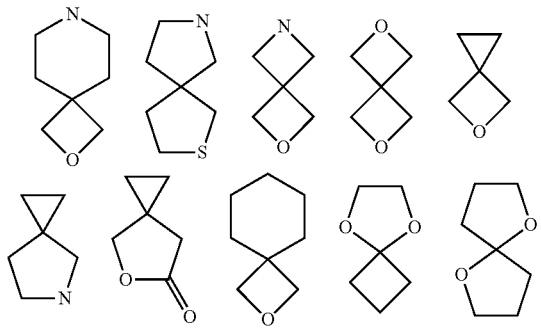

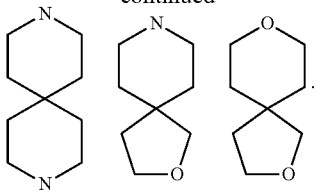

"Fused heterocyclyl" refers to a polycyclic heterocyclyl in which each ring shares a pair of adjacent atoms with the other rings in the system, wherein one or more of the rings may contain one or more double bonds, but none of them has a fully conjugated π-electron system, wherein one or more of the ring atoms are heteroatoms selected from nitrogen, oxygen or $S(O)_r$ (wherein r is an integer of 0, 1 or 2), and the remaining ring atoms are carbon atoms. According to the number of formed rings, the fused heterocyclyl may be bicyclic, tricyclic, tetracyclic or polycyclic, including but not limited to:

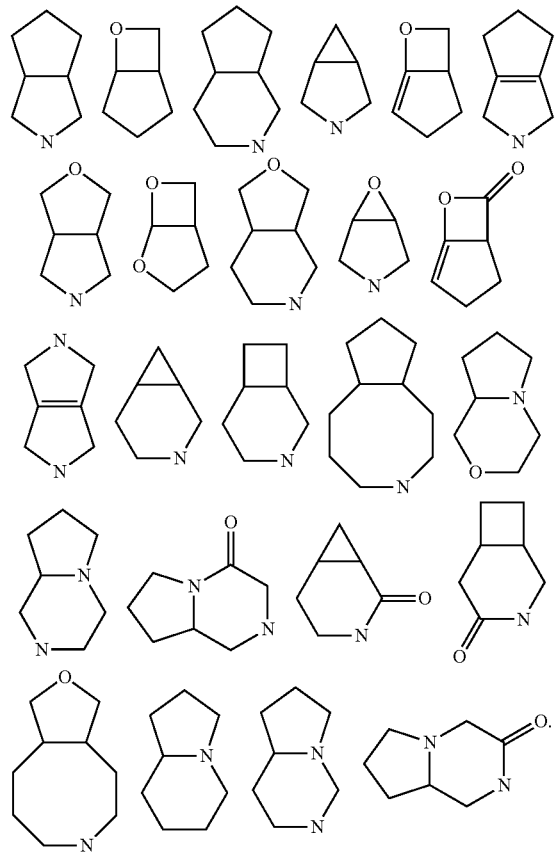

"Bridged heterocyclyl" refers to a polycyclic heterocyclyl in which any two rings share two carbon atoms that are not directly attached to each other, wherein these rings may contain one or more double bonds, but none of them has a fully conjugated π-electron system, wherein one or more of the ring atoms are heteroatoms selected from nitrogen, oxygen or $S(O)_r$ (wherein r is an integer of 0, 1 or 2), and the remaining ring atoms are carbon atoms. According to the number of formed rings, the bridged heterocyclyl may be bicyclic, tricyclic, tetracyclic or polycyclic, including but not limited to:

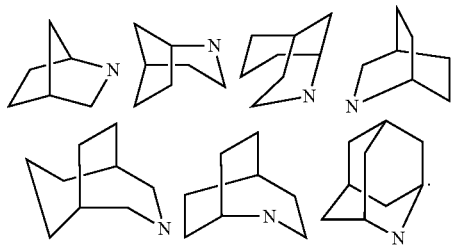

The heterocyclyl ring may be fused to an aryl, heteroaryl or cycloalkyl ring, wherein the ring attached to the parent structure is heterocyclyl, including but not limited to:

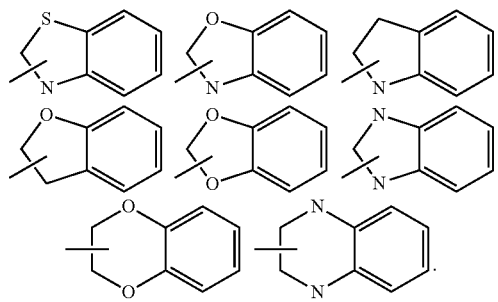

Heterocyclyl can be optionally substituted or unsubstituted, and when it is substituted, the substituent is preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, $—C_{0-8}—S(O)_rR_{14}$, $—C_{0-8}—O—R_{15}$, $—C_{0-8}—C(O)OR_{15}$, $—C_{0-8}—C(O)R_{16}$, $—C_{0-8}—O—C(O)R_{16}$, $—C_{0-8}—NR_{17}R_{18}$, $—C_{0-8}—C(O)NR_{17}R_{18}$ and $—C_{0-8}—N(R_{17})—C(O)R_{16}$.

"Aryl" means an all-carbon monocyclic or fused-polycyclic group (i.e., rings that share a pair of adjacent carbon atoms) and a polycyclic group having a conjugated π-electron system (i.e., rings with adjacent pairs of carbon atoms), for example, "$C_{5-10}$ aryl" means an all-carbon aryl containing 5 to 10 carbon atoms, and "5-10 membered aryl" means an all-carbon aryl containing 5 to 10 carbon atoms, including but not limited to phenyl and naphthyl. The aryl ring can be fused to a heteroaryl, heterocyclyl or cycloalkyl ring, wherein the ring attached to the parent structure is the aryl ring, including but not limited to:

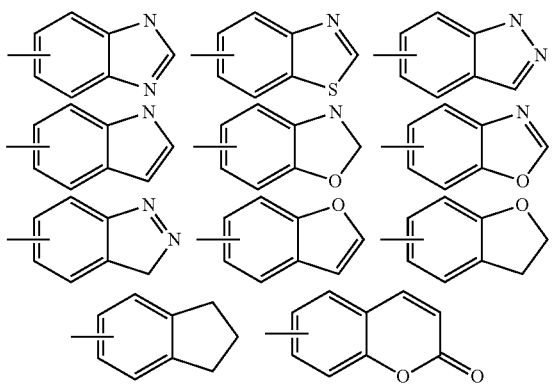

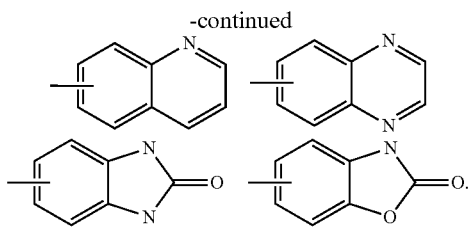

Aryl can be substituted or unsubstituted, and when it is substituted, the substituent is preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$R$_{14}$, —$C_{0-8}$—O—R$_{15}$, —$C_{0-8}$—C(O)OR$_{15}$, —$C_{0-8}$—C(O)R$_{16}$, —$C_{0-8}$—O—C(O)R$_{16}$, —$C_{0-8}$—NR$_{17}$R$_{18}$, —$C_{0-8}$—C(O)NR$_{17}$R$_{18}$ and —$C_{0-8}$—N(R$_{17}$)—C(O)R$_{16}$.

"Heteroaryl" refers to a heteroaromatic system containing 1 to 4 heteroatoms, and the heteroatoms include heteroatoms selected from nitrogen, oxygen or S(O)r (wherein r is an integer of 0, 1 or 2), for example, 5-8 membered heteroaryl means a heteroaromatic system containing 5 to 8 ring atoms, and 5-10 membered heteroaryl means a heteroaromatic system containing 5 to 10 ring atoms, including but not limited to furyl, thiophenyl, pyridyl, pyrrolyl, N-alkylpyrrolyl, pyrimidinyl, pyrazinyl, imidazolyl, tetrazolyl, etc. The heteroaryl ring can be fused to an aryl, heterocyclyl or cycloalkyl ring, wherein the ring attached to the parent structure is the heteroaryl ring, including but not limited to:

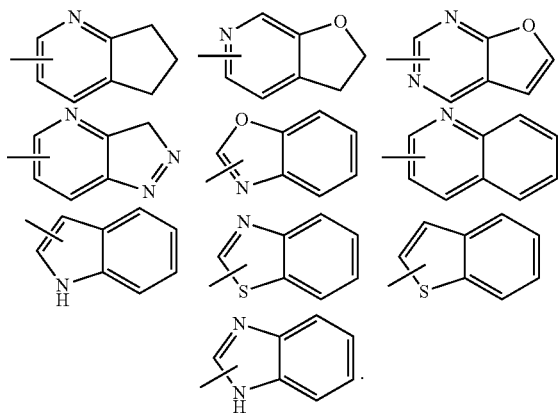

Heteroaryl can be optionally substituted or unsubstituted, and when it is substituted, the substituent is preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$R$_{14}$, —$C_{0-8}$—O—R$_{15}$, —$C_{0-8}$—C(O)OR$_{15}$, —$C_{0-8}$—C(O)R$_{16}$, —$C_{0-8}$—O—C(O)R$_{16}$, —$C_{0-8}$—NR$_{17}$R$_{18}$, —$C_{0-8}$—C(O)NR$_{17}$R$_{18}$ and —$C_{0-8}$—N(R$_{17}$)—C(O)R$_{16}$.

"Alkenyl" refers to an alkyl defined as above consisting of at least two carbon atoms and at least one carbon-carbon double bond, for example, $C_{2-8}$ alkenyl means a linear or branched alkenyl containing 2 to 8 carbon atoms. The alkenyl includes but is not limited to vinyl, 1-propenyl, 2-propenyl, 1-, 2- or 3-butenyl, etc.

Alkenyl can be substituted or unsubstituted, and when it is substituted, the substituent is preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$R$_{14}$, —$C_{0-8}$—O—R$_{15}$, —$C_{0-8}$—C(O)OR$_{15}$, —$C_{0-8}$—C(O)R$_{16}$, —$C_{0-8}$—O—C(O)R$_{16}$, —$C_{0-8}$—NR$_{17}$R$_{18}$, —$C_{0-8}$—C(O)NR$_{17}$R$_{18}$ and —$C_{0-8}$—N(R$_{17}$)—C(O)R$_{16}$.

"Alkynyl" refers to an alkyl defined as above consisting of at least two carbon atoms and at least one carbon-carbon triple bond, for example, $C_{2-8}$ alkynyl means a linear or branched alkynyl containing 2 to 8 carbon atoms. The alkynyl includes but is not limited to ethynyl, 1-propynyl, 2-propynyl, 1-, 2- or 3-butynyl, etc.

Alkynyl can be substituted or unsubstituted, and when it is substituted, the substituent is preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$R$_{14}$, —$C_{0-8}$—O—R$_{15}$, —$C_{0-8}$—C(O)OR$_{15}$, —$C_{0-8}$—C(O)R$_{16}$, —$C_{0-8}$—O—C(O)R$_{16}$, —$C_{0-8}$—NR$_{17}$R$_{18}$, —$C_{0-8}$—C(O)NR$_{17}$R$_{18}$ and —$C_{0-8}$—N(R$_{17}$)—C(O)R$_{16}$.

"Alkoxy" refers to —O-(alkyl), wherein the alkyl is defined as above, for example, "$C_{1-8}$ alkoxy" means an alkoxy containing 1 to 8 carbons atoms, including but not limited to methoxy, ethoxy, propoxy, butoxy, etc.

Alkoxy can be optionally substituted or unsubstituted, and when it is substituted, the substituent is preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$R$_{14}$, —$C_{0-8}$—O—R$_{15}$, —$C_{0-8}$—C(O)OR$_{15}$, —$C_{0-8}$—C(O)R$_{16}$, —$C_{0-8}$—O—C(O)R$_{16}$, —$C_{0-8}$—NR$_{17}$R$_{18}$, —$C_{0-8}$—C(O)NR$_{17}$R$_{18}$ and —$C_{0-8}$—N(R$_{17}$)—C(O)R$_{16}$.

"Cycloalkyloxy" refers to —O-(unsubstituted cycloalkyl), wherein the cycloalkyl is defined as above, for example, "$C_{3-10}$ cycloalkyloxy" means a cycloalkyloxy containing 3 to 10 carbon atoms, including but not limited to cyclopropyloxy, cyclobutyloxy, cyclopentyloxy, cyclohexyloxy, etc.

Cycloalkyloxy can be optionally substituted or unsubstituted, and when it is substituted, the substituent is preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$R$_{14}$, —$C_{0-8}$—O—R$_{15}$, —$C_{0-8}$—C(O)OR$_{15}$, —$C_{0-8}$—C(O)R$_{16}$, —$C_{0-8}$—O—C(O)R$_{16}$, —$C_{0-8}$—NR$_{17}$R$_{18}$, —$C_{0-8}$—C(O)NR$_{17}$R$_{18}$ and —$C_{0-8}$—N(R$_{17}$)—C(O)R$_{16}$.

"3-10 membered heterocyclyloxy" refers to —O-(unsubstituted 3-10 membered heterocyclyl), wherein 3-10 membered heterocyclyl is defined as above. The 3-10 membered heterocyclyloxy can be optionally substituted or unsubstituted, and when it is substituted, the substituent is preferably one or more of the groups independently selected from the group consisting of deuterium, halogen, cyano, nitro, azido. $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$R$_{14}$, —$C_{0-8}$—O—R$_{15}$, —$C_{0-8}$—C(O)$OR_{15}$, —$C_{0-8}$—C(O)$R_{16}$, —$C_{0-8}$—O—C(O)$R_{16}$, —$C_{0-8}$—$NR_{17}R_{18}$, —$C_{0-8}$—C(O)$NR_{17}R_{18}$ and —$C_{0-8}$—N($R_{17}$)—C(O)$R_{16}$.

"$C_{5-10}$ aryloxy" refers to —O-(unsubstituted $C_{5-10}$ aryl), wherein $C_{5-10}$ aryl is defined as above. The $C_{5-10}$ aryloxy can be optionally substituted or unsubstituted, and when it is substituted, the substituent is preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r R_{14}$, —$C_{0-8}$—O—$R_{15}$, —$C_{0-8}$—C(O)$OR_{15}$, —$C_{0-8}$—C(O)$R_{16}$, —$C_{0-8}$—O—C(O)$R_{16}$, —$C_{0-8}$—$NR_{17}R_{18}$, —$C_{0-8}$—C(O)$NR_{17}R_{18}$ and —$C_{0-8}$—N($R_{17}$)—C(O)$R_{16}$.

"5-10 membered heteroaryloxy" refers to —O-(unsubstituted 5-10 membered heteroaryl), wherein the 5-10 membered heteroaryl is defined as above. The 5-10 membered heteroarylox can be optionally substituted or unsubstituted, and when it is substituted, the substituent is preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r R_{14}$, —$C_{0-8}$—O—$R_{15}$, —$C_{0-8}$—C(O)$OR_{15}$, —$C_{0-8}$—C(O)$R_{16}$, —$C_{0-8}$—O—C(O)$R_{16}$, —$C_{0-8}$—$NR_{17}R_{18}$, —$C_{0-8}$—C(O)$NR_{17}R_{18}$ and —$C_{0-8}$—N($R_{17}$)—C(O)$R_{16}$.

"$C_{1-8}$ alkanoyl" refers to a monovalent atomic group which is obtained after a hydroxy is removed from the $C_{1-8}$ alkyl acid, and is also generally referred to as "$C_{0-7}$—C(O)—", for example, "$C_1$—C(O)—" refers to an acetyl: "$C_2$—C(O)—" refers to a propionyl; and "$C_3$—C(O)—" refers to a butyryl or isobutyryl.

"—$C_{0-8}$—S(O)(=$NR_{13}$)$R_{14}$" means that the sulfur atom in —S(O)(=$NR_{13}$)$R_{14}$ is attached to $C_{0-8}$ alkyl, wherein $C_0$ alkyl refers to a bond, and $C_{1-8}$ alkyl is defined as above.

"—$C_{0-8}$—B(O$R_{15}$)$_2$" means that the boron atom in —B(O$R_{15}$)$_2$ is attached to $C_{0-8}$ alkyl, wherein $C_0$ alkyl refers to a bond, and $C_{1-8}$ alkyl is defined as above.

"—$C_{0-8}$—P(O)($R_{16}$)$_2$" means that the phosphorus atom in —P(O)($R_{16}$)$_2$ is attached to $C_{0-8}$ alkyl, wherein $C_0$ alkyl refers to a bond, and $C_{1-8}$ alkyl is defined as above.

"—$C_{0-8}$—S(O)$_r R_{14}$" means that the sulfur atom in —S(O)$_r R_{14}$ is attached to $C_{0-8}$ alkyl, wherein $C_0$ alkyl means a bond, and $C_{1-8}$ alkyl is defined as above.

"—$C_{0-8}$—O—$R_{15}$" means that the oxygen atom in —O—$R_{15}$ is attached to $C_{0-8}$ alkyl, wherein $C_0$ alkyl means a bond, and $C_{1-8}$ alkyl is defined as above.

"—$C_{0-8}$—C(O)$OR_{15}$" means that the carbonyl group in —C(O)$OR_{15}$ is attached to $C_{0-8}$ alkyl, wherein $C_0$ alkyl means a bond, and $C_{1-8}$ alkyl is defined as above.

"—$C_{0-8}$—C(O)$R_{16}$" means that the carbonyl group in —C(O)$R_{16}$ is attached to $C_{0-8}$ alkyl, wherein $C_0$ alkyl means a bond, and $C_{1-8}$ alkyl is defined as above.

"—$C_{0-8}$—O—C(O)$R_{16}$" means that the oxygen atom in —O—C(O)$R_{16}$ is attached to $C_{0-8}$ alkyl, wherein $C_0$ alkyl means a bond, and $C_{1-8}$ alkyl is defined as above.

"—$C_{0-8}$—$NR_{17}R_{18}$" means that the nitrogen atom in —$NR_{17}R_{18}$ is attached to $C_{0-8}$ alkyl, wherein $C_0$ alkyl means a bond, and $C_{1-8}$ alkyl is defined as above.

"—$C_{0-8}$—C(O)$NR_{17}R_{18}$" means that the carbonyl group in —C(O)$NR_{17}R_{18}$ is attached to $C_{0-8}$ alkyl, wherein $C_0$ alkyl means a bond, and $C_{1-8}$ alkyl is defined as above.

"—$C_{0-8}$—N($R_{17}$)—C(O)$R_{16}$" means that the nitrogen atom in —N($R_{17}$)—C(O)$R_{16}$ is attached to $C_{0-8}$ alkyl, wherein $C_0$ alkyl means a bond, and $C_{1-8}$ alkyl is defined as above.

"$C_{1-8}$ haloalkyl" refers to an alkyl having 1 to 8 carbon atoms in which hydrogens on the alkyl are optionally substituted by a fluorine, chlorine, bromine or iodine atom, including but not limited to difluoromethyl, dichloromethyl, dibromomethyl, trifluoromethyl, trichloromethyl, tribromomethyl, etc.

"$C_{1-8}$ haloalkoxy" refers to an alkoxy having 1 to 8 carbon atoms in which hydrogens on the alkyl are optionally substituted by a fluorine, chlorine, bromine or iodine atom, including but not limited to difluoromethoxy, dichloromethoxy, dibromomethoxy, trifluoromethoxy, trichloromethoxy, tribromomethoxy, etc.

"Halogen" refers to fluorine, chlorine, bromine or iodine. "THF" refers to tetrahydrofuran. "PE" refers to petroleum ether. "EA" refers to ethyl acetate. "DMF" refers to N,N-dimethylformamide. "DMSO" refers to dimethylsulfoxide. "$CH_2Cl_2$" refers to dichloromethane. "MeOH" refers to methanol. "DIPEA" refers to N,N-diisopropylethylamine. "DEAD" refers to diethyl azodiformate. "SEM-Cl" refers to 2-(trimethylsilyl)ethoxymethyl chloride. "X-phos" refers to 4,5-bis(diphenylphosphino)-9,9-dimethylxanthene. "Pd(dppf)$Cl_2$" refers to [1,1'-bis(diphenylphosphino)ferrocene] palladium dichloride dichloromethane. "HATU" refers to 2-(7-azabenzotriazol-1-yl)-N,N,N',N'-tetramethyluronium hexafluorophosphate.

The term "optional" or "optionally" means that the event or circumstance subsequently described may, but not necessarily, occur, and that the description includes instances where the event or circumstance occurs or does not occur. For example, "heterocyclyl group optionally substituted by alkyl" means that alkyl may be, but not necessarily, present, and that the description includes instances where the heterocyclyl group is or is not substituted by alkyl.

The term "substituted" means that one or more hydrogen atoms in a group are each independently substituted by a corresponding number of substituents. It goes without saying that a substituent is only in its possible chemical position, and those skilled in the art will be able to determine (by experiments or theories) possible or impossible substitution without undue efforts. For example, it may be unstable when an amino or hydroxy having a free hydrogen is bound to a carbon atom having an unsaturated bond (such as olefin).

"Pharmaceutical composition" refers to a mixture containing one or more of the compounds described herein or a physiologically/pharmaceutically acceptable salt or prodrug thereof, and other chemical components, for example physiologically/pharmaceutically acceptable carriers and excipients. The purpose of the pharmaceutical composition is to promote the administration to an organism, which facilitates the absorption of the active ingredient, thereby exerting biological activities.

The present invention is further explained in detail below with reference to examples, which are not intended to limit the present invention, and the present invention is not merely limited to the contents of the examples.

The compound structure of the present invention is determined by nuclear magnetic resonance (NMR) and/or liquid chromatography-mass spectrometry (LC-MS). The NMR chemical shift (δ) is given in parts per million (ppm). The NMR determination is conducted by using a Bruker AVANCE-400 nuclear magnetic resonance apparatus, with hexadeuterodimethyl sulfoxide (DMSO-$d_6$), tetradeuteromethanol (CD₃OD), and deuterated chloroform (CDCl₃) as determination solvents, and tetramethylsilane (TMS) as internal standard.

The LC-MS determination is conducted by using an Agilent 6120 mass spectrometer. The HPLC determination is conducted by using an Agilent 1200 DAD high pressure liquid chromatograph (Sunfire C18 150*4.6 mm chromatographic column) and a Waters 2695-2996 high pressure liquid chromatograph (Gimini C18 150*4.6 mm chromatographic column).

Yantai Yellow Sea HSGF254 or Qingdao GF254 silica gel plate is adopted as a thin layer chromatography (TLC) silica gel plate. The specification adopted by the TLC is 0.15-0.20 mm, and the specification adopted by the thin layer chromatography for the separation and purification of products is 0.4-0.5 mm. The Yantai Yellow Sea silica gel of 200-300 mesh is generally utilized as a carrier in column chromatography.

Starting materials in the examples of the present invention are known and commercially available, or may be synthesized by using or according to methods known in the art.

Unless otherwise stated, all reactions of the present invention are carried out under a dry nitrogen or argon atmosphere with continuous magnetic stirring, wherein the solvent is a dry solvent, and the reaction temperature is in degree centigrade (° C.).

Preparation of Intermediates

1. Preparation of 5-bromo-N-isopropyl-4-methoxypyrimidin-2-amine (Intermediate A1)

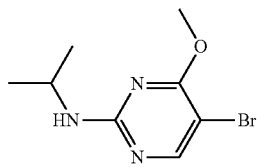

5-bromo-2-chloro-4-methoxypyrimidine (2.4 g, 10.8 mmol), isopropylamine (6 mL, 72.4 mmol) and DIPEA (4 mL, 21.6 mmol) were added to a sealed tube, and then tetrahydrofuran (20 mL) was added. The reaction mixture was heated to 80° C. and reacted for 5 hrs, and the reaction solution was cooled, and the crude product was separated by column chromatography to obtain 5-bromo-N-isopropyl-4-methoxypyrimidin-2-amine (2.3 g, yield 88%).

2. Preparation of (2-(isopropylamino)-4-methoxypyrimidin-5-yl)boronic Acid (Intermediate B1)

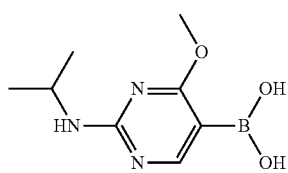

5-bromo-N-isopropyl-4-methoxypyrimidin-2-amine (4.4 g, 18 mmol) was dissolved in dimethylformamide (30 mL), and bis(pinacolato)diboron (13.7 g, 53.9 mmol), [1,1'-bis (diphenylphosphino)ferrocene]palladium dichloride (2.6 g, 3.6 mmol) and potassium acetate (10.6 g, 107.8 mmol) were added. The nitrogen was charged to replace three times by evacuation at room temperature, and the reaction solution was heated to 90° C. and stirred for 2 hrs at this temperature. Ethyl acetate and water were added, and then the mixture solution was separated. The organic phase was successively washed with water and a saturated brine, then dried over anhydrous sodium sulfate, filtered, concentrated, and separated by column chromatography [eluent: petroleum ether/ethyl acetate (5:1)~(3:1)] to obtain (2-(isopropylamino)-4-methoxypyrimidin-5-yl)boronic acid (4.3 g, yield 81.7%). MS m/z (ESI): 212 [M+H]⁺.

3. Preparation of 6-chloro-2-methylnicotinaldehyde (Intermediate C1)

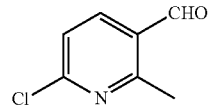

N-butyllithium (1.6 M, 94 mL, 146.6 mmol) was dissolved in dry tetrahydrofuran (100 mL), then the solution of 3-bromo-6-chloro-2-methylpyridine (20 g, 97.7 mmol) in dry tetrahydrofuran was slowly added dropwise after the mixture solution was cooled down to −70° C. under a nitrogen atmosphere. The reaction solution was continuously stirred for 15 min at −70° C., then dry N,N-dimethylformamide (14.6 g, 195.4 mmol) was added dropwise at −70° C. The reaction solution was warmed to room temperature, and stirred for 2 hrs. Water (200 mL) was added, and the mixture solution was extracted with ethyl acetate (150 mL*3). The organic phases were combined, successively washed with water (200 mL*3) and a saturated brine (200 mL), dried over anhydrous sodium sulfate, concentrated and then separated by column chromatography [eluent: PE/EA (10:1)] to obtain 6-chloro-2-methylnicotinaldehyde (11 g, yield 72.6%). MS m/z (ESI): 156 [M+H]⁺.

4. Preparation of 5-(1-methyl-1H-pyrazol-4-yl)-1H-pyrrolo[2,3-b]pyridine (Intermediate D1)

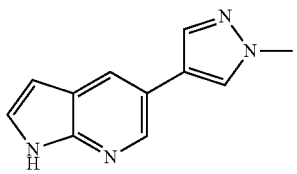

5-bromo-1H-pyrrolo[2,3-b]pyridine (1.0 g, 5.1 mmol) was dissolved the mixture of 1,4-dioxane/water (20 mL/10 mL), and 1-methyl-4-(4,4,5,5-tetramethyl-1,3,2-dioxaborolan-2-yl)-1H-pyrazol (1.27 g, 6.1 mmol), [1,1'-bis(diphenylphosphino)ferrocene]palladium dichloride (0.37 g, 0.51 mmol) and sodium carbonate (1.62 g, 15.3 mmol) were added. The nitrogen was charged to replace three times by evacuation at room temperature, and the reaction solution was heated to 90° C. and stirred for 2 hrs at this temperature. The reaction solution was cooled down to room temperature, and water (100 mL) was added. The mixture solution was extracted with ethyl acetate (50 mL*3), and the organic phases were combined, washed three times with a saturated brine, concentrated, and then separated by thin-layer plate chromatography [eluent: petroleum ether/ethyl acetate (1:5)] to obtain 5-(1-methyl-1H-pyrazol-4-yl)-1H-pyrrolo[2,3-b]pyridine (900 mg, yield 90%). MS m/z (ESI): 199 [M+H]$^+$.

5. Preparation of (6-chloro-2-methylpyridin-3-yl)(1H-pyrrolo[2,3-b]pyridin-3-yl)methanol and 3-((6-chloro-2-methylpyridin-3-yl)(methoxy)methyl)-1H-pyrrolo[2,3-b]pyridine (Intermediate E1)

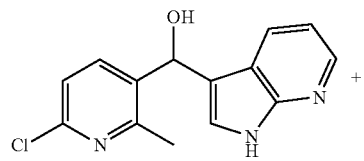

+

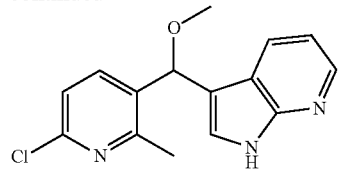

6-chloro-2-methylnicotinaldehyde (156 mg, 1.0 mmol) was dissolved in methanol (6 mL), and 7-azaindole (118 mg, 1.0 mmol) and potassium hydroxide (196 mg, 3.5 mmol) were added. The reaction solution was stirred overnight at room temperature. The reaction solution was diluted with water and extracted with ethyl acetate, and the organic phase was dried, concentrated and then separated by column chromatography [eluent: petroleum ether~petroleum ether/ethyl acetate (1:1)] to obtain (6-chloro-2-methylpyridin-3-yl)(1H-pyrrolo[2,3-b]pyridin-3-yl)methanol (115 mg, yield 42%). MS m/z (ESI): 274 [M+H]$^+$. Meanwhile, 3-((6-chloro-2-methylpyridin-3-yl)(methoxy)methyl)-1H-pyrrolo[2,3-b]pyridine (50 mg, yield 17%) was obtained. MS m/z (ESI): 288[M+H]$^+$.

Intermediates E2 to E8 were prepared according to the synthesis method of intermediate E1.

| Intermediate No. | Structural formula | Chemical name | ESI-MS: [M + H]$^+$ |
|---|---|---|---|
| E2 | | (6-chloropyridin-3-yl)(1H-pyrrolo[2,3-b]pyridin-3-yl)methanol & 3-((6-chloropyridin-3-yl)(methoxy)methyl)-1H-pyrrolo[2,3-b]pyridine | 260 & 274 |
| E3 | | (6-chloro-2-methylpyridin-3-yl)(5-(2-methoxyethoxy)-1H-pyrrolo[2,3-b]pyridin-3-yl)methanol & 3-((6-chloro-2-methylpyridin-3-yl)(methoxy)methyl)-5-(2-methoxyethoxy)-1H-pyrrolo[2,3-b]pyridine | 348 & 362 |

Intermediates E2 to E8 were prepared according to the synthesis method of intermediate E1.

| Intermediate No. | Structural formula | Chemical name | ESI-MS: [M + H]+ |
|---|---|---|---|
| E4 | | (6-chloro-2-methylpyridin-3-yl)(5-fluoro-1H-pyrrolo[2,3-b]pyridin-3-yl)methanol | 292 |
| E5 | | (5-chloro-1H-pyrrolo[2,3-b]pyridin-3-yl)(6-chloro-2-methylpyridin-3-yl)methanol | 308 |
| E6 | | (6-chloro-2-methylpyridin-3-yl)(5-methyl-1H-pyrrolo[2,3-b]pyridin-3-yl)methanol | 288 |
| E7 | | (6-chloro-2-methylpyridin-3-yl)(5-(1-methyl-1H-pyrazol-4-yl)-1H-pyrrolo[2,3-b]pyridin-3-yl)methanol | 368 |
| E8 | | (6-chloro-2-methylpyridin-3-yl)(5-methoxy-1H-pyrrolo[2,3-b]pyridin-3-yl)methanol | 318 |

6. Preparation of 3-((6-chloro-2-methylpyridin-3-yl)methyl)-1H-pyrrolo[2,3-b]pyridine (Intermediate F1)

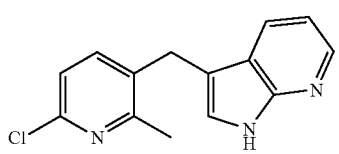 [SMILES: Cc1nc(Cl)ccc1Cc1c[nH]c2ncccc12]

(6-chloro-2-methylpyridin-3-yl)(1H-pyrrolo[2,3-b]pyridin-3-yl)methanol (115 mg, 0.42 mmol) and 3-((6-chloro-2-methylpyridin-3-yl)(methoxy)methyl)-1H-pyrrolo[2,3-b]pyridine (50 mg, 0.17 mmol) were dissolved in acetonitrile (15 mL), and triethylsilane (0.95 mL, 5.9 mmol) and trifluoroacetic acid (0.44 mL, 5.9 mmol) were added. The reaction solution was stirred for 4 hrs at 80° C. After the reaction was completed, the reaction solution was concentrated, then alkalified with a saturated sodium bicarbonate aqueous solution, and extracted with ethyl acetate, and the organic phase was dried, concentrated and then separated by column chromatography [eluent: Dichloromethane~dichloromethane/methanol (10:1)] to obtain 3-((6-chloro-2-methylpyridin-3-yl)methyl)-1H-pyrrolo[2,3-b]pyridine (126 mg, yield 82%). MS m/z (ESI): 258 [M+H]+.

Intermediates F2 to F8 were prepared according to the synthesis method of intermediate F1.

| Intermediate No. | Structural formula | Chemical name | MS m/z (ESI): [M + H]+ |
|---|---|---|---|
| F2 | | 3-((6-chloropyridin-3-yl)methyl)-1H-pyrrolo[2,3-b]pyridine | 244 |
| F3 | | 3-((6-chloro-2-methylpyridin-3-yl)methyl)-5-(2-methoxyethoxy)-1H-pyrrolo[2,3-b]pyridine | 332 |
| F4 | | 3-((6-chloro-2-methylpyridin-3-yl)methyl)-5-fluoro-1H-pyrrolo[2,3-b]pyridine | 276 |
| F5 | | 5-chloro-3-((6-chloro-2-methylpyridin-3-yl)methyl)-1H-pyrrolo[2,3-b]pyridine | 292 |
| F6 | | 3-((6-chloro-2-methylpyridin-3-yl)methyl)-5-methyl-1H-pyrrolo[2,3-b]pyridine | 272 |
| F7 | | 3-((6-chloro-2-methylpyridin-3-yl)methyl)-5-(1-methyl-1H-pyrazol-4-yl)-1H-pyrrolo[2,3-b]pyridine | 338 |
| F8 | | 3-((6-chloro-2-methylpyridin-3-yl)methyl)-5-methoxy-1H-pyrrolo[2,3-b]pyridine | 288 |

7. Preparation of 5-(5-((1H-pyrrolo[2,3-b]pyridin-3-yl)methyl)-6-methylpyridin-2-yl)-N-isopropyl-4-methoxypyrimidin-2-amine (Intermediate G1)

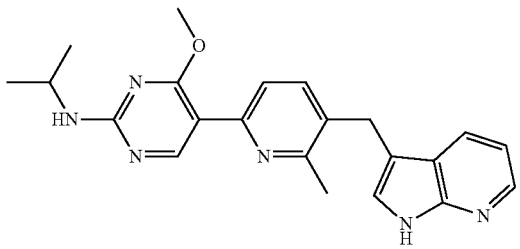 [SMILES: COc1nc(NC(C)C)ncc1-c1ccc(Cc2c[nH]c3ncccc23)c(C)n1]

(2-(isopropylamino)-4-methoxypyrimidin-5-yl)boronic acid (92 mg, 0.43 mmol) was dissolved in the mixture solvent of dioxane and water (10 mL, volume ratio 2:1), and 3-((6-chloro-2-methylpyridin-3-yl)methyl)-1H-pyrrolo[2,3-b]pyridine (56 mg, 0.22 mmol), potassium carbonate (90 mg, 0.65 mmol) and [1,1'-bis(diphenylphosphino)ferrocene] palladium dichloride (32 mg, 0.04 mmol) were successively added. The mixture solution was stirred overnight at 110° C. under a nitrogen atmosphere. Then the reaction solution was cooled, filtered, concentrated and separated by column chromatography [eluent: Dichloromethane~dichloromethane/methanol (12:1)] to obtain 5-(5-((1H-pyrrolo[2,3-b]pyridin-3-yl)methyl)-6-methylpyridin-2-yl)-N-isopropyl-4-methoxypyrimidin-2-amine (30 mg, yield 35%). MS m/z (ESI): 389 [M+H]+.

Intermediates G2 to G4 were prepared according to the synthesis method of intermediate G1.

| Intermediate No. | Structural formula | Chemical name | MS m/z (ESI): [M + H]+ |
|---|---|---|---|
| G2 | | 5-(5-((1H-pyrrolo[2,3-b]pyridin-3-yl)methyl)pyridin-2-yl)-N-isopropyl-4-methoxypyrimidin-2-amine | 375 |
| G3 | | N-isopropyl-4-methoxy-5-(5-((5-(2-methoxyethoxy)-1H-pyrrrolo[2,3-b]pyridin-3-yl)methyl)-6-methylpyridin-2-yl)pyrimidin-2-amine | 463 |
| G4 | | 5-(5-((5-fluoro-1H-pyrrolo[2,3-b]pyridin-3-yl)methyl)-6-methylpyridin-2-yl)-N-isopropyl-4-methoxypyrimidin-2-amine | 407 |

8. Preparation of 6-(2-(isopropylamino)-4-methoxy-pyrimidin-5-yl)-2-methylnicotinaldehyde (Intermediate H1)

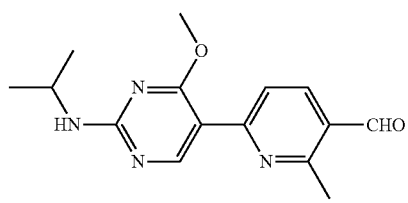 [SMILES: COc1nc(NC(C)C)ncc1-c1ccc(C=O)c(C)n1]

(2-(isopropylamino)-4-methoxypyrimidin-5-yl)boronic acid (814 mg, 3.86 mmol), 6-chloro-2-methylnicotinaldehyde (200 mg, 1.29 mmol), sodium carbonate (273 mg, 2.57 mmol) and tetrakis(triphenylphosphine)palladium (149 mg, 0.13 mmol) were added into a dry single-necked flask. The nitrogen was charged to replace three times by evacuation, then the mixture solvent of 1,4-dioxane and water (12 mL, volume ratio 2:1) was added. The reaction solution was stirred for 3 hrs at 85° C. After the reaction was completed, the solution was diluted with ethyl acetate (30 mL), and filtered through the celite pad to remove the solid. The filtrate was concentrated and separated by column chromatography [eluent: petroleum ether~petroleum ether/ethyl acetate (3:1)] to obtain 6-(2-(isopropylamino)-4-methoxy-pyrimidin-5-yl)-2-methylnicotinaldehyde (300 mg, yield 81%). MS m/z (ESI): 287 [M+H]$^+$.

9. Preparation of (6-(2-(isopropylamino)-4-methoxypyrimidin-5-yl)-2-methylpyridin-3-yl)(1H-pyrrolo[2,3-b]pyridin-3-yl)methanol (Intermediate I1)

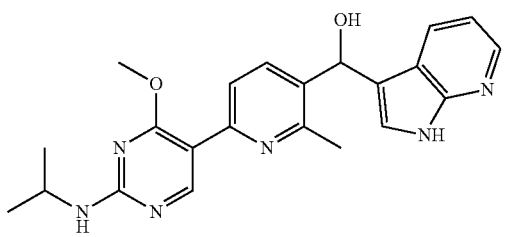 [SMILES: COc1nc(NC(C)C)ncc1-c1ccc(C(O)c2c[nH]c3ncccc23)c(C)n1]

1H-pyrrolo[2,3-b]pyridine (219 mg, 1.86 mmol) and potassium hydroxide (346 mg, 6, 18 mmol) were added to the solution of 6-(2-(isopropylamino)-4-methoxypyrimidin-5-yl)-2-methylnicotinaldehyde (590 mg, 2.06 mmol) in methanol (15 mL), and the mixture solution reacted at room temperature for 2 days. Dichloromethane and water were added, and then the mixture was separated. The organic phase was successively washed with water and a saturated brine, then dried over anhydrous sodium sulfate, filtered, concentrated, and separated by column chromatography [eluent: methanol/dichloromethane (1:15)] to obtain (6-(2-(isopropylamino)-4-methoxypyrimidin-5-yl)-2-methylpyridin-3-yl) 1H-pyrrolo[2,3-b]pyridin-3-yl)methanol (200 mg, yield 26.5%). MS m/z (ESI): 406 [M+1]$^+$.

10. Preparation of (6-(2-(isopropylamino)-4-methoxypyrimidin-5-yl)-2-methylpyridin-3-yl)(1H-pyrrolo[2,3-b]pyridin-3-yl)methanone (Intermediate J1)

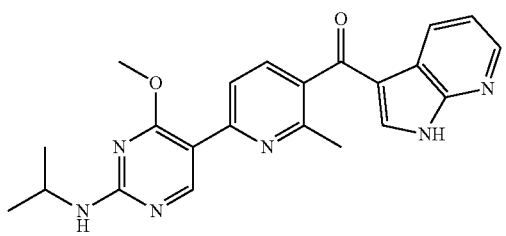 [SMILES: COc1nc(NC(C)C)ncc1-c1ccc(C(=O)c2c[nH]c3ncccc23)c(C)n1]

1,1-dihydro-1,1,1-triacetoxy-1,2-benzoiodoxazol-3(1H)-one (315 mg, 0.74 mmol) was added to the solution of (6-(2-(isopropylamino)-4-methoxypyrimidin-5-yl)-2-methylpyridin-3-yl) (1H-pyrrolo[2,3-b]pyridin-3-yl)methanol (200 mg, 0.49 mmol) in dichloromethane (20 mL), and the reaction solution was stirred at room temperature for 3 hrs. Dichloromethane and saturated sodium hydrogen sulfite solution were added, and then the mixture solution was separated. The organic phase was successively washed with water and a saturated brine, then dried over anhydrous sodium sulfate, filtered, concentrated and separated by column chromatography [eluent: methanol/dichloromethane (1:15)] to obtain (6-(2-(isopropylamino)-4-methoxypyrimidin-5-yl)-2-methylpyridin-3-yl)(1H-pyrrolo[2,3-b]pyridin-3-yl)methanone (120 mg, yield 61%). MS m/z (ESI): 404 [M+H]$^+$.

11. Preparation of 6-(2-(isopropylamino)-6-oxo-1,6-dihydropyrimidin-5-yl)-2-methylnicotinaldehyde (Intermediate K1)

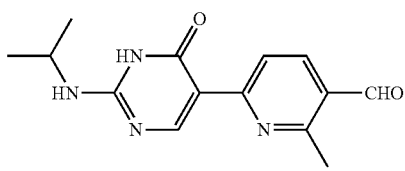 [SMILES: Cc1nc(-c2cnc(NC(C)C)[nH]c2=O)ccc1C=O]

6-(2-(isopropylamino)-4-methoxypyrimidin-5-yl)-2-methylnicotinaldehyde (300 mg, 1.05 mmol) was dissolved in acetic acid (15 mL), and 40% hydrobromic acid aqueous solution (0.4 mL) was added. The reaction solution was stirred at 90° C. for 2 hrs. The reaction solution was cooled, then filtered and dried to obtain the hydrobromide of 6-(2-(isopropylamino)-6-oxo-1,6-dihydropyrimidin-5-yl)-2-methylnicotinaldehyde (318 mg, yield 89%). MS m/z (ESI): 273 [M+H]$^+$.

12. Preparation of 6-(2-(isopropylamino)-1-methyl-6-oxo-1,6-dihydropyrimidin-5-yl)-2-methylnicotinaldehyde (Intermediate L1)

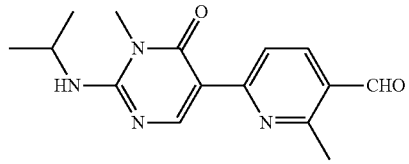 [SMILES: Cc1nc(-c2cnc(NC(C)C)n(C)c2=O)ccc1C=O]

The hydrobromide of 6-(2-(isopropylamino)-6-oxo-1,6-dihydropyrimidin-5-yl)-2-methylnicotinaldehyde (300 mg, 0.85 mmol) was dissolved in N,N-dimethylformamide (7 mL), and potassium carbonate (470 mg, 3.4 mmol) was added. The reaction solution was stirred a t room temperature for 0.5 hr. Then iodomethane (0.16 mL, 2.55 mmol) was added, and the reaction solution was continuously stirred for 2 hrs. After the reaction was completed, the reaction solution was diluted with ethyl acetate (20 mL), and washed twice with water, and the organic phase was dried, concentrated and then separated by column chromatography [eluent: petroleum ether~petroleum ether/ethyl acetate (1:3)] to obtain 6-(2-(isopropylamino)-1-methyl-6-oxo-1,6-dihydropyrimidin-5-yl)-2-methylnicotinaldehyde (139 mg, yield 60%). MS m/z (ESI): 287 [M+H]$^+$.

13. Preparation of 3-(ethylamino)propan-1-ol (Intermediate M1)

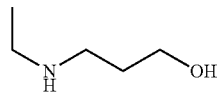

3-aminopropan-1-ol (5 g, 67 mmol) was dissolved in dichloromethane (10 mL), and acetaldehyde (1.76 g, 40 mmol) was added dropwise at 0° C. The mixture solution reacted at room temperature for 16 hrs. Sodium borohydride (2.7 g, 80 mmol) was added in batches after the solution was cooled down to 0° C., and the reaction solution was continuously stirred for 0.5 hr. The reaction solution was added with water, extracted with dichloromethane, dried over anhydrous sodium sulfate and concentrated to obtain the crude product of 3-(ethylamino)propan-1-ol (3 g, yield 50%), which was directly used in the next step.

14. Preparation of 3-(methylamino)butan-1-ol (Intermediate M2)

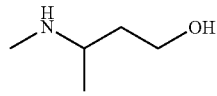

4-hydroxylbutan-2-one (3 g, 34 mmol) and methylamine (12.77 g, 68 mmol) were dissolved in ethanol (10 mL), and 10% palladium on carbon (300 mg) was added. The mixture solution reacted at room temperature for 16 hrs. The reaction solution was filtered, and the filtrate was concentrated to obtain 3-(methylamino)butan-1-ol (3 g, yield 87%), which was directly used in the next step.

15. Preparation of 3-((5-bromo-4-methoxypyrimidin-2-yl)(methyl)amino)propan-1-ol (Intermediate N1)

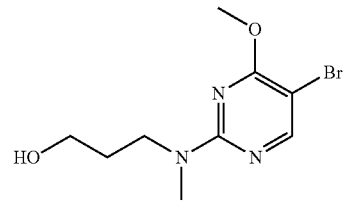

5-bromo-2-chloro-4-methoxypyrimidine (1.16 g, 5.23 mmol), 3-(methylamino)propan-1-ol (698 mg, 7.84 mmol) and diisopropylethylamine (1.35 g, 10.46 mmol) were dissolved in tetrahydrofuran (10 mL), and the mixture solution reacted at 80° C. for 16 hrs. The reaction solution was concentrated and then separated by column chromatography [eluent: petroleum ether/ethyl acetate (1:1)] to obtain 3-((5-bromo-4-methoxypyrimidin-2-yl)(methyl)amino)propan-1-ol (1.25 g, yield 87%). MS m/z (ESI): 276 [M+H]$^+$.

Intermediates N2 to N3 were prepared according to the synthesis method of intermediate N1.

| Intermediate No. | Structural formula | Chemical name | MS m/z (ESI):[M + H]$^+$ |
|---|---|---|---|
| N2 |  | 3-((5-bromo-4-methoxypyrimidin-2-yl)(ethyl)amino)propan-1-ol | 290 |

| Intermediates N2 to N3 were prepared according to the synthesis method of intermediate N1. | | | |
|---|---|---|---|
| Intermediate No. | Structural formula | Chemical name | MS m/z (ESI):[M + H]+ |
| N3 | 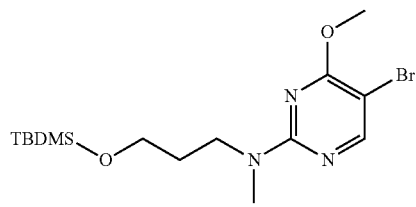 | 3-((5-bromo-4-methoxypyrimidin-2-yl)(methyl)amino)butan-1-ol | 290 |

16. Preparation of 5-bromo-N-(3-((tert-butyldimethylsilyl)oxy)propyl)-4-methoxy-N-methylpyrimidin-2-amine (Intermediate O1)

3-((5-bromo-4-methoxypyrimidin-2-yl)(methyl)amino)propan-1-ol (4 g, 14.49 mmol) and imidazole (1.48 g, 21.74 mmol) were dissolved in dichloromethane (10 mL), and tert-butyldimethylsilyl chloride (3.26 g, 27.74 mmol) was added dropwise at 0° C. The mixture solution reacted at room temperature for 4 hrs. The reaction solution was washed with water, and the organic layer was dried over sodium sulfate, concentrated and then separated by column chromatography [developing solvent: PE:EA (10:1)] to obtain 5-bromo-N-(3-((tert-butyldimethylsilyl)oxy)propyl)-4-methoxy-N-methylprimidin-2-amine (5 g, yield 89%). MS m/z (ESI): 390 [M+H]+.

| Intermediates O2, O3 and O1-b were prepared according to the synthesis method of intermediate O1. | | | |
|---|---|---|---|
| Intermediate No. | Structural formula | Chemical name | ESI-MS:[M + H]+ |
| O2 | | 5-bromo-N-(3-((tert-butyldiphenylsilyl)oxy)propyl)-N-ethyl-4-methoxypyrimidin-2-amine | 528 |
| O3 | | 5-bromo-N-(4-((tert-butyldiphenylsilyl)oxy)butan-2-yl)-4-methoxy-N-methylpyrimidin-2-amine | 528 |
| O1-b | | 5-bromo-N-(3-((tert-butyldiphenylsilyl)oxy)propyl)-4-methoxy-N-methylpyrimidin-2-amine | 514 |

17. Preparation of (2-((3-((tert-butyldimethylsilyl)oxy)propyl)(methyl)amino)-4-methoxypyrimidin-5-yl)boronic Acid (Intermediate P1)

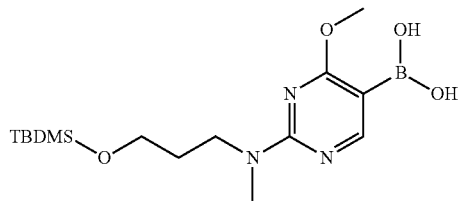

5-bromo-N-(3-((tert-butyldimethylsilyl)oxy)propyl)-4-methoxy-N-methylpyrimidin-2-amine (3.5 g, 9.0 mmol), 4,4,4',4',5,5,5',5'-octamethyl-2,2'-bi(1,3,2-dioxaborolan) (4.57 g, 18 mmol), potassium acetate (2.65 g, 27 mmol) and palladium 1,1'-didiphenylphosphineferrocenedichloride (900 mg, 0.1 mmol) were dissolved in N,N-dimethylformamide (20 mL), and the mixture solution reacted at 120° C. for 2 hrs under a nitrogen atmosphere. After the reaction was completed, the reaction solution was added with water (50 mL) and extracted with ethyl acetate, and the organic phase was washed with water and brine, dried over sodium sulfate, concentrated and then separated by column chromatography [developing solvent: PE/EA (1:1)] to obtain (2-((3-((tert-butyldimethylsilyl)oxy)propyl)(methyl)amino)-4-methoxypyrimidin-5-yl)boronic acid (assumed as boric acid according to LCMS) (2 g, yield 63%). MS m/z (ESI): 356 [M+H]+.

Intermediates P2 to P4 and P1-b were prepared according to the synthesis method of in P1.

| Intermediate No. | Structural formula | Chemical name | ESI-MS:[M + H]+ |
|---|---|---|---|
| P2 | | (2-((3-((Tert-butyldiphenylsilyl)oxy)propyl)(ethyl)-amino)-4-methoxypyrimidin-5-yl)boronic acid | 494 |
| P3 | | (2-((4-((tert-butyldiphenylsilyl)oxy)butan-2-yl)(methyl)amino)-4-methoxypyrimidin-5-yl)boronic acid | 494 |
| P4 | | (2-((3-hydroxypropyl)(methyl)amino)-4-methoxypyrimidin-5-yl)boronic acid | 242 |
| P1-b | | (2-((3-((tert-butyldiphenylsilyl)oxy)propyl)(methyl)-amino)-4-methoxypyrimidin-5-yl)boronic acid | 480 |

18. Preparation of N-(3-((tert-butyldimethylsilyl)oxy)propyl)-5-(5-((5-chloro-1H-pyrrolo[2,3-b]pyridin-3-yl)methyl)-6-methylpyridin-2-yl)-4-methoxy-N-methylpyrimidin-2-amine (Intermediate Q1)

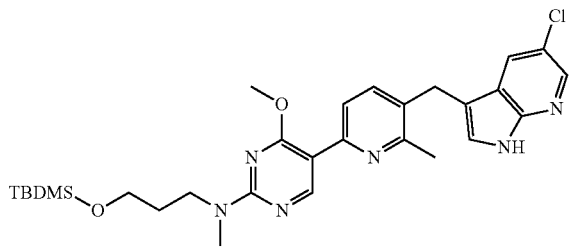

(2-((3-((tert-butyldimethylsilyl)oxy)propy)(methyl)amino)-4-methoxypyrimidin-5-yl)boronic acid (1.22 g, 3.43 mmol), 5-chloro-3-((6-chloro-2-methylpyridin-3-yl)methyl)-1H-pyrrolo[2,3-b]pyridine (1 g, 3.43 mmol), potassium carbonate (947 mg, 6.86 mmol) and palladium 1,1'-didiphenylphosphineferrocenedichloride (250 mg, 0.343 mmol) were dissolved in the mixture of dioxane (15 mL) and water (5 mL), and the mixture solution reacted at 90° C. for 2 hrs under a nitrogen atmosphere. Then the reaction solution was diluted with ethyl acetate (5 mL), successively washed with water (5 mL*3) and a saturated brine (5 mL), dried over anhydrous sodium sulfate, concentrated and then separated by thin-layer plate chromatography [developing solvent: PE:EA (1:1)] to obtain N-(3-((tert-butyldimethylsilyl)oxy)propyl)-5-(5-((5-chloro-1H-pyrrolo[2,3-b]pyridin-3-yl)methyl)-6-methylpyridin-2-yl)-4-methoxy-N-methylpyrimidin-2-amine (1.2 g, yield 62%). MS m/z (ESI): 567 [M+H]$^+$.

Intermediates Q2 to Q9 were prepared according to the synthesis method of intermediate Q1.

| Intermediate No. | Structural formula | Chemical name | MS m/z (ESI): [M + H]$^+$ |
|---|---|---|---|
| Q2 | | 5-(5-((1H-pyrrolo[2,3-b]pyridin-3-yl)methyl)-6-methylpyridin-2-yl)-N-(3-((tert-butyldimethylsilyl)oxy)propyl)-4-methoxy-N-methylpyrimidin-2-amine | 533 |
| Q3 | | N-(4-((tert-butyldiphenylsilyl)oxy)butan-2-yl)-5-(5-((5-chloro-1H-pyrrolo[2,3-6]pyridin-3-yl)methyl)-6-methylpyridin-2-yl)-4-methoxy-N-methylpyrimidin-2-amine | 705 |
| Q4 | | N-(3-((tert-butyldiphenylsilyl)oxy)propyl)-5-(5-((5-chloro-1H-pyrrolo[2,3-b]pyridin-3-yl)methyl)-6-methylpyridin-2-yl)-N-ethyl-4-methoxypyridin-2-amine | 705 |

-continued

Intermediates Q2 to Q9 were prepared according to the synthesis method of intermediate Q1.

| Intermediate No. | Structural formula | Chemical name | MS m/z (ESI): [M + H]+ |
|---|---|---|---|
| Q5 | | N-(3-((tert-butyldiphenylsilyl)oxy)propyl)-N-ethyl-4-methoxy-5-(6-methyl-5-((5-(1-methyl-1H-pyrazol-4-yl)-1H-pyrrolo[2,3-b]pyridin-3-yl)methyl)pyridin-2-yl)pyrimidin-2-amine | 751 |
| Q6 | | N-(3-((tert-butyldiphenylsilyl)oxy)propyl)-4-methoxy-N-methyl-5-(6-methyl-5-((5-(1-methyl-1H-pyrazol-4-yl)-1H-pyrrolo[2,3-b]pyridin-3-yl)methyl)pyridin-2-yl)pyrimidin-2-amine | 737 |
| Q7 | | 5-(5-((1H-pyrrolo[2,3-b]pyridin-3-yl)methyl)-6-methylpyridin-2-yl)-N-(3-((tert-butyldiphenylsilyl)oxy)propyl)-N-ethyl-4-methoxypyrimidin-2-amine | 671 |
| Q8 | | N-(3-((tert-butyldiphenylsilyl)oxy)propyl)-5-(5-((5-fluoro-1H-pyrrolo[2,3-b]pyridin-3-yl)methyl)-6-methylpyridin-2-yl)-4-methoxy-N-methylpyrimidin-2-amine | 675 |

-continued

| Intermediate No. | Structural formula | Chemical name | MS m/z (ESI): [M + H]+ |
|---|---|---|---|
| Q9 | | N-(3-((tert-butyldiphenylsilyl)oxy)propyl)-4-methoxy-N-methyl-5-(6-methyl-5-((5-methyl-1H-pyrrolo[2,3-b]pyridin-3-yl)methyl)pyridin-2-yl)pyrimidin-2-amine | 671 |

Intermediates Q2 to Q9 were prepared according to the synthesis method of intermediate Q1.

19. Preparation of 3-((5-(5-((5-chloro-1H-pyrrolo[2,3-b]pyridin-3-yl)methyl)-6-methylpyridin-2-yl)-4-methoxypyrimidin-2-yl)(methyl)amino)propan-1-ol (Intermediate R1)

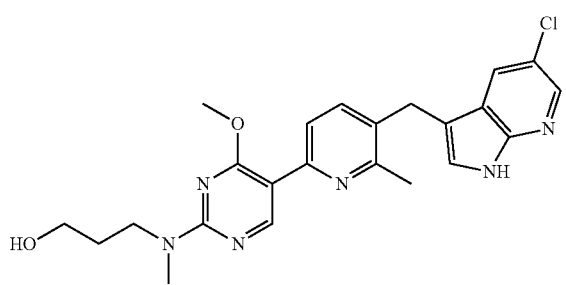 [SMILES: COc1nc(N(C)CCCO)ncc1-c1ccc(Cc2c[nH]c3ncc(Cl)cc23)c(C)n1]

N-(3-((tert-butyldimethylsilyl)oxy)propyl)-5-(5-((5-chloro-1H-pyrrolo[2,3-b]pyridin-3-yl)methyl)-6-methylpyridin-2-yl)-4-methoxy-N-methylpyrimidin-2-amine (1.2 g, 2.12 mmol) was dissolved in tetrahydrofuran (15 mL), and tetrabutylammonium fluoride (4.24 mL, 4.24 mmol) was added dropwise. The mixture solution reacted at room temperature for 2 hrs. Then the reaction solution was diluted with ethyl acetate (50 mL), successively washed with water (50 mL*3) and a saturated brine (50 mL), dried over anhydrous sodium sulfate, concentrated and separated by column chromatography to obtain 3-((5-(5-((5-chloro-1H-pyrrolo[2,3-b]pyridin-3-yl)methyl)-6-methylpyridin-2-yl)-4-methoxypyrimidin-2-yl)(methyl)amino)propan-1-ol (400 mg, yield 42%). MS m/z (ESI): 453 [M+H]+.

Intermediates R2 to R9 were prepared according to the synthesis method of intermediate R1.

| Intermediate No. | Structural formula | Chemical name | MS m/z (ESI): [M + H]+ |
|---|---|---|---|
| R2 | | 3-((5-(5-((1H-pyrrolo[2,3-b]pyridin-3-yl)methyl)-6-methylpyridin-2-yl)-4-methoxypyrimidin-2-yl)(methyl)amino)propan-1-ol | 419 |
| R3 | | 3-((5-(5-((5-chloro-1H-pyrrolo[2,3-b]pyridin-3-yl)methyl)-6-methylpyridin-2-yl)-4-methoxypyrimidin-2-yl)(methyl)amino)butan-1-ol | 467 |

-continued

Intermediates R2 to R9 were prepared according to the synthesis method of intermediate R1.

| Intermediate No. | Structural formula | Chemical name | MS m/z (ESI): [M + H]+ |
|---|---|---|---|
| R4 | | 3-((5-(5-((5-chloro-1H-pyrrolo[2,3-b]pyridin-3-yl)methyl)-6-methylpyridin-2-yl)-4-methoxypyrimidin-2-yl)(ethyl)amino)propan-1-ol | 467 |
| R5 | | 3-(ethyl(4-methoxy-5-(6-methyl-5-((5-(1-methyl-1H-pyrazol-4-yl)-1H-pyrrolo[2,3-b]pyridin-3-yl)methyl)pyridin-2-yl)pyrimidin-2-yl)amino)propan-1-ol | 513 |
| R6 | | 3-((4-methoxy-5-(6-methyl-5-((5-(1-methyl-1H-pyrazol-4-yl)-1H-pyrrolo[2,3-b]pyridin-3-yl)methyl)pyridin-2-yl)pyrimidin-2-yl)(methyl)amino)propan-1-ol | 499 |
| R7 | | 3-((5-(5-((1H-pyrrolo[2,3-b]pyridin-3-yl)methyl)-6-methylpyridin-2-yl)-4-methoxypyrimidin-2-yl)(ethyl)amino)propan-1-ol | 433 |

Intermediates R2 to R9 were prepared according to the synthesis method of intermediate R1.

| Intermediate No. | Structural formula | Chemical name | MS m/z (ESI): [M + H]+ |
|---|---|---|---|
| R8 | | 3-((5-(5-((5-fluoro-1H-pyrrolo[2,3-b]pyridin-3-yl)methyl)-6-methylpyridin-2-yl)-4-methoxypyrimidin-2-yl)(methyl)amino)propan-1-ol | 437 |
| R9 | | 3-((4-methoxy-5-(6-methyl-5-((5-methyl-1H-pyrrolo[2,3-b]pyridin-3-yl)methyl)pyridin-2-yl)pyrimidin-2-yl)(methyl)amino)propan-1-ol | 433 |

20. Preparation of 3-((4-methoxy-5-(5-((5-methoxy-1H-pyrrolo[2,3-b]pyridin-3-yl)methyl)-6-methylpyridin-2-yl)pyrimidin-2-yl)(methyl)amino)propan-1-ol (Intermediate R10)

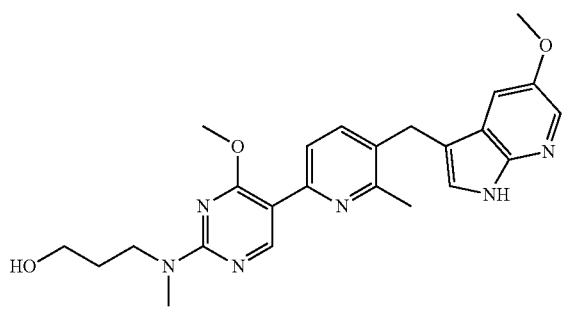 [SMILES: COc1cnc2[nH]cc(Cc3ccc(-c4cnc(N(C)CCCO)nc4OC)nc3C)c2c1]

(2-((3-hydroxypropyl)(methyl)amino)-4-methoxypyrimidin-5-yl)boronic acid (400 mg, 1.66 mmol), 3-((6-chloro-2-methylpyridin-3-yl)methyl)-5-methoxy-1H-pyrrolo[2,3-b]pyridine (476 mg, 1.66 mmol), potassium carbonate (458 mg, 3.22 mmol) and palladium 1,1'-didiphenylphosphine-ferrocenedichloride (120 mg, 0.166 mmol) were dissolved in the mixture of 1,4-dioxane (15 mL) and water (5 mL), and the reaction solution reacted at 90° C. for 2 hrs under a nitrogen atmosphere. The reaction solution was diluted with ethyl acetate (5 mL), successively washed with water (5 mL*3) and a saturated brine (5 mL), dried over anhydrous sodium sulfate, concentrated and then separated by thin-layer plate chromatography [developing solvent: PE/EA (1:1)] to obtain 3-((4-methoxy-5-(5-((5-methoxy-1H-pyrrolo[2,3-b]pyridin-3-yl)methyl)-6-methylpyridin-2-yl)pyrimidin-2-yl)(methyl)amino)propan-1-ol (372 mg, yield 50%). MS m/z (ESI): 449 [M+H]+.

21. Preparation of Tert-Butyl 3-(6-(2-((3-hydroxypropyl)(methyl)amino)-4-methoxypyrimidin-5-yl)-2-methylnicotinoyl)-1H-pyrrolo[2,3-b]pyridine-1-carboxylate (Intermediate R11)

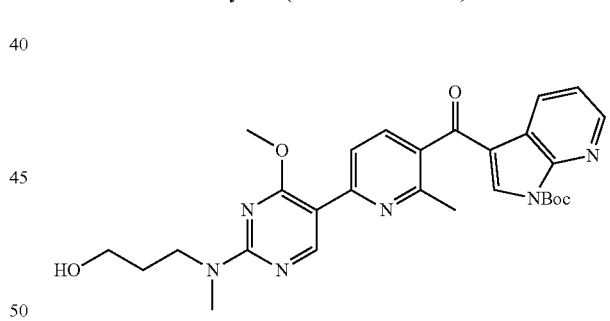

Step 1: Preparation of (6-chloro-2-methylpyridin-3-yl)(3a,7a-dihydro-1H-pyrrolo[2,3-b]pyridin-3-yl)methanone 1,1-dihydro-1,1,1-triacetoxy-1,2-benzoiodoxazol-3(1H)-one (3.7 g, 8.79 mmol) was added to the solution of (6-chloro-2-methylpyridin-3-yl)(3a,7a-dihydro-1H-pyrrolo[2,3-b]pyridin-3-yl)methanol (1.6 g, 5.86 mmol) in dichloromethane (20 mL), and the reaction solution was stirred at room temperature for 2 hrs. Dichloromethane and saturated sodium bicarbonate solution were added, and then the mixture solution was separated. The organic phase was successively washed with water and a saturated brine, then dried over anhydrous sodium sulfate, filtered, concentrated and separated by column chromatography [eluent: ethyl acetate/ petroleum ether (2:1)] to obtain (6-chloro-2-methylpyridin-3-yl)(3a,7a-dihydro-1H-pyrrolo[2,3-b]pyridin-3-yl)methanone (600 mg, yield 38%). MS m/z (ESI): 274 [M+H]⁺.

Step 2: Preparation of Tert-Butyl 3-(6-chloro-2-methylnicotinoyl)-3a,7a-dihydro-1H-pyrrolo[2,3-b]pyridin-1-carboxylate Di-tert-butyldicarbonate (724 mg, 3.3 mmol) and N,N-dimethylpyridin-4-amine (27 mg, 0.22 mmol) were added to the solution of (6-chloro-2-methylpyridin-3-yl)(3a,7a-dihydro-1H-pyrrolo[2,3-b]pyridin-3-yl)methanone (600 mg, 2.2 mmol) in dichloromethane (20 mL), and the reaction solution was stirred at room temperature for 2 hrs. Dichloromethane and water were added, and then the mixture was separated. The organic phase was successively washed with water and a saturated brine, then dried over anhydrous sodium sulfate, filtered, concentrated, and separated by column chromatography [eluent: ethyl acetate/petroleum ether (1:5)] to obtain tert-butyl 3-(6-chloro-2-methylnicotinoyl)-3a,7a-dihydro-1H-pyrrolo[2,3-b]pyridin-1-carboxylate (490 mg, yield 60%). MS m/z (ESI): 374 [M+H]⁺.

Step 3: Preparation of Tert-Butyl 3-(6-(2-((3-hydroxypropyl)(methyl)amino)-4-methoxypyrimidin-5-yl)-2-methylnicotinoyl)-3a,7a-dihydro-1H-pyrrolo[2,3-b]pyridin-1-carboxylate 3-((4-methoxy-5-(4,4,5,5-tetramethyl-1,3,2-dioxaborolan-2-yl)pyrimidin-2-yl)(methyl)amino)propan-1-ol (346 mg, 1.08 mmol), potassium carbonate (221 mg, 1.62 mmol) and [1,1'-bis(diphenylphosphino)ferrocene]palladium dichloride (II) (39 mg, 0.054 mmol) were added to the solution of tert-butyl 3-(6-chloro-2-methylnicotinoyl)-3a,7a-dihydro-1H-pyrrolo[2,3-b]pyridin-1-carboxylate (200 mg, 0.54 mmol) in 1,4-dioxane/water (15 mL/5 mL). The nitrogen was charged to replace three times by evacuation, then the reaction solution was stirred at 90° C. for 2 hrs. Dichloromethane and water were added, and then the mixture was separated. The organic phase was successively washed with water and a saturated brine, then dried over anhydrous sodium sulfate, filtered, concentrated, and separated by column chromatography [eluent: ethyl acetate/petroleum ether (2:1)] to obtain tert-butyl 3-(6-(2-((3-hydroxypropyl)(methyl)amino)-4-methoxypyrimidin-5-yl)-2-methylnicotinoyl)-3a,7a-dihydro-1H-pyrrolo[2,3-b]pyridin-1-carboxylate (120 mg, yield 42%). MS m/z (ESI): 535 [M+H]⁺.

22. Preparation of 1-isopropyl-1-dihydro-4H-imidazo[4,5-c]pyridin-4-one (Intermediate S1)

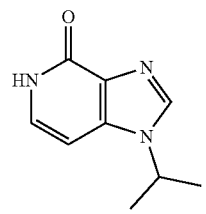

Step 1: Preparation of 4-chloro-1H-imidazo[4,5-c]pyridine (intermediate S1-1)

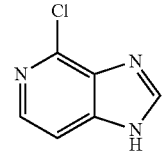

2-chloro-3,4-diaminopyridine (2.87 g, 20 mmol) and trimethyl orthoformate (40 mL) were added into a round-bottom flask, and concentrated hydrochloric acid (3 mL) was slowly added dropwise at room temperature, the mixture solution was stirred overnight at room temperature. A large number of solids were precipitated and filtered out, and the filter cake was washed with petroleum ether and dried to obtain the crude product of 4-chloro-1H-imidazo[4,5-c]pyridine (3.7 g, yield 98%). MS m/z (ESI): 154 [M+H]⁺.

Step 2: Preparation of 4-chloro-1-isopropyl-1H-imidazo[4,5-c]pyridine (Intermediate S1-2)

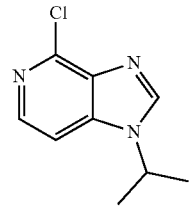

4-chloro-1H-imidazo[4,5-c]pyridine hydrochloride (3.7 g, 19.5 mmol) was dissolved in anhydrous DMF (50 mL) in a round-bottom flask, and potassium carbonate (13.8 g, 98 mmol) and isopropyl bromide (5.6 mL, 59 mmol) were added. The reaction solution was heated to 80° C. and reacted for 2 hrs at this temperature, and DMF was removed by vacuum evaporation. The result crude product was separated by column chromatography to obtain 4-chloro-1-isopropyl-1H-imidazo[4,5-c]pyridine (3.3 g, yield 87%). MS m/z (ESI): 195 [M+H]⁺.

Step 3: Preparation of 1-isopropyl-1,5-dihydro-4H-imidazo[4,5-c]pyridin-4-one (Intermediate S1)

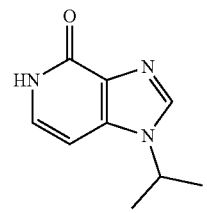

4-chloro-1-isopropyl-1H-imidazo[4,5-c]pyridine (2.2 g, 11.2 mmol) was dissolved in the mixture of ethanol (88 mL) and water (88 mL) in a round-bottom flask, and concentrated hydrochloric acid (44 mL) was added. The reaction solution was heated to 100° C. and reacted for 2 days at this temperature. Thereafter, the reaction solution was alkalified with the solution of ammonia in methanol, and the solvent was removed by vacuum evaporation. Then the reaction solution was separated by column chromatography to obtain 1-isopropyl-1,5-dihydro-4H-imidazo[4,5-c]pyridin-4-one (1.0 g, yield 47%). MS m/z (ESI): 178 [M+H]+.

23. Preparation of 6-(1-isopropyl-4-oxo-1,4-dihydro-5H-imidazo[4,5-c]pyridin-5-yl)-2-methylnicotinaldehyde (Intermediate T1)

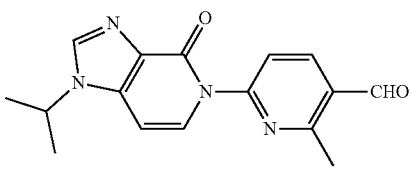 [SMILES: Cc1nc(-n2ccc3c(ncn3C(C)C)c2=O)ccc1C=O]

Step 1: Preparation of 6-iodo-2-methylnicotinaldehyde (Intermediate T1-1)

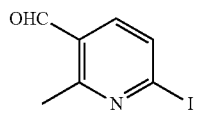

6-chloro-2-methylnicotinaldehyde (156 mg, 1.0 mmol) was dissolved in acetonitrile (3.5 mL), and sodium iodide (1.05 g, 7.0 mmol) and concentrated hydrochloric acid (0.03 mL) were added. The reaction solution was stirred at reflux for 3 hrs. The reaction solution was cooled, then alkalified with a saturated sodium bicarbonate aqueous solution, and extracted with ethyl acetate, and the organic phase was dried, concentrated and separated by column chromatography [eluent: petroleum ether~petroleum ether/ethyl acetate (4:1)] to obtain 6-iodo-2-methylnicotinaldehyde (220 mg, yield 89%). MS m/z (ESI): 248 [M+H]+.

Step 2: Preparation of 6-(1-isopropyl-4-oxo-1,4-dihydro-5H-imidazo[4,5-c]pyridin-5-yl)-2-methylnicotinaldehyde (Intermediate T1)

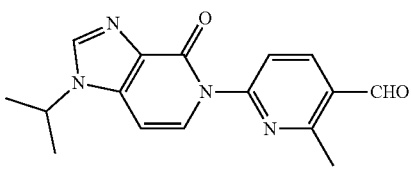

6-iodo-2-methylnicotinaldehyde (490 mg, 2.0 mmol) was dissolved in DMSO (13 mL), and 1-isopropyl-1,5-dihydro-4H-imidazo[4,5-c]pyridin-4-one (355 mg, 2.0 mmol), copper acetate (182 mg, 1.0 mmol) and potassium carbonate (553 mg, 4.0 mmol) were successively added. The reaction solution was stirred at 150° C. for 1 hr under a nitrogen atmosphere. The reaction solution was cooled, then diluted with ethyl acetate, and then filtered, and the filtrate was washed with water, dried, concentrated, and then separated by column chromatography [eluent: dichloromethane~dichloromethane/methanol (12:1)] to obtain 6-(1-isopropyl-4-oxo-1,4-dihydro-5H-imidazo[4,5-c]pyridin-5-yl)-2-methylnicotinaldehyde (70 mg, yield 12%). MS m/z (ESI): 297 [M+H]+.

PREPARATION OF EXAMPLES

Example 1: Preparation of 5-(5-((1-pyrrolo[2,3-b]pyridin-3-yl)methyl)-6-methylpyridin-2-yl)-2-(isopropylamino)pyrimidin-4(3H)-one

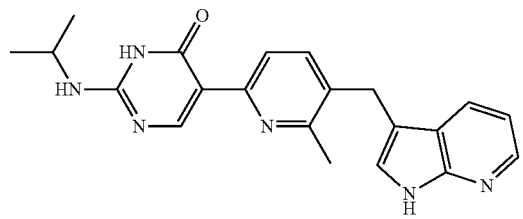

5-(5-((1H-pyrrolo[2,3-b]pyridin-3-yl)methyl)-6-methylpyridin-2-yl)-N-isopropyl-4-methoxypyrimidin-2-amine (30 mg, 0.08 mmol) was dissolved in acetic acid (3 mL), and 40% hydrobromic acid aqueous solution (0.085 mL, 0.6 mmol) was added. The reaction solution was stirred at 90° C. for 6 hrs. The reaction solution was cooled, then alkalified with saturated sodium bicarbonate aqueous solution and extracted with ethyl acetate, and the organic phase was dried, concentrated and then separated by plate chromatography [eluent: dichloromethane~dichloromethane/methanol (10:1)] to obtain 5-(5-((1H-pyrrolo[2,3-b]pyridin-3-yl)methyl)-6-methylpyridin-2-yl)-2-(isopropylamino)pyrimidin-4(3H)-one (6.9 mg, yield 24%). MS m/z (ESI): 375 [M+H]+.

1H NMR (400 MHz, DMSO-d6) δ 11.44 (s, 1H), 10.73 (s, 1H), 8.74-8.57 (m, 1H), 8.18 (d, J=4.7 Hz, 1H), 8.03 (s, 1H), 7.83 (d, J=7.9 Hz, 1H), 7.47 (s, 1H), 7.20 (s, 1H), 7.00 (dd, J=7.9, 4.7 Hz, 1H), 6.61 (s, 1H), 4.19-3.92 (m, 3H), 2.49 (s, 3H), 1.16 (d, J=6.5 Hz, 6H).

Examples 2 to 6 were Prepared According to the Synthesis Method of Example 1

| Example No. | Structural formula | Chemical name | MS m/z (ESI): [M + H]+ |
|---|---|---|---|
| 2 | 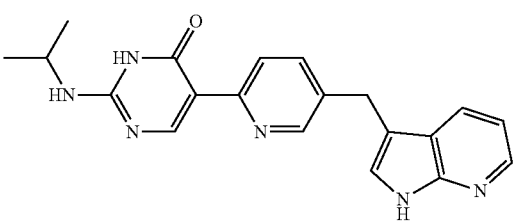 [SMILES: CC(C)Nc1ncc(-c2ccc(Cc3c[nH]c4ncccc34)cn2)c(=O)[nH]1] | 5-(5-((1H-pyrrolo[2,3-b]pyridin-3-yl)methyl)pyridin-2-yl)-2-(isopropylamino)pyrimidin-4(3H)-one | 361 |

| Example No. | Structural formula | Chemical name | MS m/z (ESI): [M + H]+ |
|---|---|---|---|
| 3 | | 2-(isopropylamino)-5-(5-((5-(2-methoxyethoxy)-1H-pyrrolo[2,3-b]pyridin-3-yl)methyl)-6-methylpyridin-2-yl)pyrimidin-4(3H)-one | 449 |
| 4 | | 5-(5-((5-(2-hydroxyethoxy)-1H-pyrrolo[2,3-b]pyridin-3-yl)methyl)-6-methylpyridin-2-yl)-2-(isopropylamino)pyrimidin-4(3H)-one | 435 |
| 5 | | 5-(5-((5-fluoro-1H-pyrrolo[2,3-b]pyridin-3-yl)methyl)-6-methylpyridin-2-yl)-2-(isopropylamino)pyrimidin-4(3H)-one | 393 |
| 6 | | 2-(isopropylamino)-5-(6-methyl-5-(1H-pyrrolo[2,3-b]pyridine-3-carbonyl)pyridin-2-yl)pyrimidin-4(3H)-one | 389 |

Herein, the nuclear magnetic resonance data of the compounds obtained from the above examples 2 to 6 were listed as follows:

| Example No. | $^1$H NMR (400 MHz) |
|---|---|
| 2 | (DMSO-$d_6$) δ 11.43 (s, 1H), 10.76 (s, 1H), 8.59 (s, 1H), 8.49 (s, 1H), 8.17 (d, J = 5.7 Hz, 2H), 7.87 (d, J = 7.7 Hz, 1H), 7.61 (s, 1H), 7.33 (s, 1H), 7.00 (dd, J = 7.8, 4.7 Hz, 1H), 6.62 (s, 1H), 4.12-3.98 (m, 3H), 1.16 (d, J = 6.5 Hz, 6H). |
| 3 | (DMSO-$d_6$) δ 11.29 (s, 1H), 10.75 (s, 1H), 8.63 (s, 1H), 8.03 (d, J = 8.1 Hz, 1H), 7.95 (d, J = 2.7 Hz, 1H), 7.47-7.42 (m, 2H), 7.14 (s, 1H), 6.63 (s, 1H), 4.13-3.96 (m, 5H), 3.68-3.60 (m, 2H), 3.30 (s, 3H), 2.48 (s, 3H), 1.16 (d, J = 6.5 Hz, 6H). |
| 4 | (DMSO-$d_6$) δ 11.28 (s, 1H), 10.78 (s, 1H), 8.64 (s, 1H), 8.02 (d, J = 8.0 Hz, 1H), 7.95 (d, J = 2.7 Hz, 1H), 7.49 (s, 1H), 7.42 (d, J = 2.7 Hz, 1H), 7.14 (d J = 2.4 Hz, 1H), 6.67 (s, 1H), 4.87 (t, J = 5.6 Hz, 1H), 4.09-3.97 (m, 5H), 3.70 (q, J = 5.1 Hz, 2H), 2.49 (s, 3H), 1.16 (d, J = 6.5 Hz, 6H). |
| 5 | (DMSO-$d_6$) δ 11.61 (s, 1H), 10.74 (s, 1H), 8.64 (s, 1H), 8.17 (dd, J = 2.7, 1.7 Hz, 1H), 8.03 (d, J = 8.2 Hz, 1H), 7.73 (dd, J = 9.6, 2.8 Hz, 1H), 7.51 (s, 1H), 7.31 (s, 1H), 6.64 (s, 1H), 4.11-3.97 (m, 3H), 2.49 (s, 3H), 1.16 (d, J = 6.5 Hz, 6H). |
| 6 | (CD$_3$OD) δ 8.70 (s, 1H), 8.64 (d, J = 8 Hz, 1H), 8.37 (s, 1H), 8.15 (d, J = 8 Hz, 1H), 7.83 (d, J = 2 Hz, 1H), 7.81 (s, 1H), 7.35 (dd, J = 4 Hz, 1H) 4.18-4.15 (m, 1H), 2.58 (s, 3H), 1.27 (d, J = 2 Hz, 6H). |

Example 7: Preparation of 5-(5-((1H-pyrrolo[2,3-b]pyridin-3-yl)methyl)-6-methylpyridin-2-yl)-2-(isopropylamino)-3-methylpyrimidin-4(3H)-one

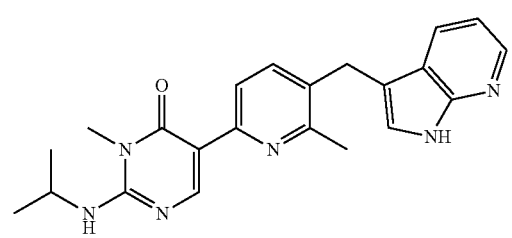 [SMILES: Cc1nc(-c2cnc(NC(C)C)n(C)c2=O)ccc1Cc1c[nH]c2ncccc12]

Step 1: Preparation of tert-butyl 3-((6-(2-(isopropylamino)-6-oxo-1,6-dihydropyrimidin-5-yl)-2-methylpyridin-3-yl)methyl)-1H-pyrrolo[2,3-b]pyridine-1-carboxylate

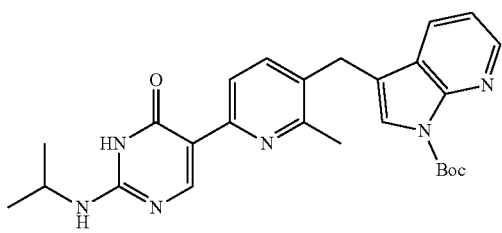 [SMILES: Cc1nc(-c2cnc(NC(C)C)[nH]c2=O)ccc1Cc1cn(C(=O)OC(C)(C)C)c2ncccc12]

5-(5-((H-pyrrolo[2,3-b]pyridin-3-yl)methyl)-6-methylpyridin-2-yl)-2-(isopropylamino)pyrimidin-4(3H)-one (45 mg, 0.12 mmol) was dissolved in tetrahydrofuran (3 mL), and di-tert-butyl dicarbonate (39 mg, 0.18 mmol) and N,N-diisopropylethylamine (46 mg, 0.36 mmol) were added. The reaction solution was stirred at room temperature for 2 hrs. The reaction solution was diluted with water and extracted with ethyl acetate, and the organic phase was dried, concentrated and then separated by column chromatography [eluent: petroleum ether~petroleum ether/ethyl acetate (1:1)] to obtain tert-butyl 3-((6-(2-(isopropylamino)-6-oxo-1,6-dihydropyrimidin-5-yl)-2-methylpyridin-3-yl)methyl)-1H-pyrrolo[2,3-b]pyridine-1-carboxylate (39 mg, yield 68%). MS m/z (ESI): 475 [M+H]+.

Step 2: Preparation of Tert-Butyl 3-((6-(2-(isopropylamino)-1-methyl-6-oxo-1,6-dihydropyrimidin-5-yl)-2-methylpyridin-3-yl)methyl)-1H-pyrrolo[2,3-b]pyridine-1-carboxylate

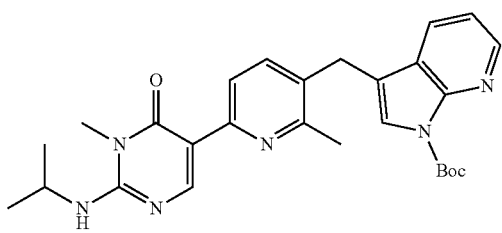 [SMILES: Cc1nc(-c2cnc(NC(C)C)n(C)c2=O)ccc1Cc1cn(C(=O)OC(C)(C)C)c2ncccc12]

Tert-butyl 3-((6-(2-(isopropylamino)-6-oxo-1,6-dihydropyrimidin-5-yl)-2-methylpyridin-3-yl)methyl)-1H-pyrrolo[2,3-b]pyridine-1-carboxylate (39 mg, 0.07 mmol) was dissolved in N,N-dimethylformamide (2 mL), and potassium carbonate (28 mg, 0.2 mmol) and iodomethane (29 mg, 0.2 mmol) were added. The reaction solution was stirred at room temperature for 2 hrs. The reaction solution was diluted with water and extracted with ethyl acetate, and the organic phase was dried, concentrated and then separated by column chromatography [eluent: petroleum ether~petroleum ether/ethyl acetate (2:1)] to obtain tert-butyl 3-((6-(2-(isopropylamino)-1-methyl-6-oxo-1,6-dihydropyrimidin-5-yl)-2-methylpyridin-3-yl)methyl)-1H-pyrrolo[2,3-b]pyridine-1-carboxylate (25 mg, yield 75%). MS m/z (ESI): 489 [M+H]+.

Step 3: Preparation of 5-(5-((1H-pyrrolo[2,3-b]pyridin-3-yl)methyl)-6-methylpyridin-2-yl)-2-(isopropylamino)-3-methylpyrimidin-4(3H)-one

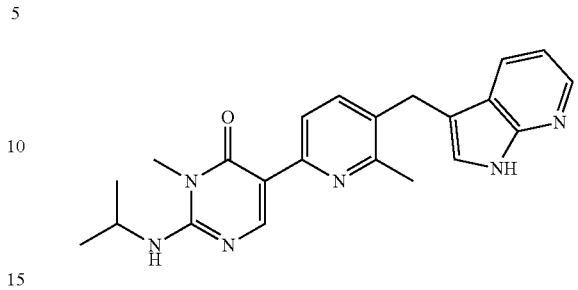

tert-butyl 3-((6-(2-(isopropylamino)-1-methyl-6-oxo-1,6-dihydropyrimidin-5-yl)-2-methylpyridin-3-yl)methyl)-1H-pyrrolo[2,3-b]pyridine-1-carboxylate (25 mg, 0.05 mmol) was dissolved in DCM (3 mL), and trifluoroacetic acid (2 mL) was added. The reaction solution was stirred at room temperature for 2 hrs. The reaction solution was concentrated, then alkalified with saturated sodium bicarbonate aqueous solution and extracted with ethyl acetate, and the organic phase was dried, concentrated and then separated by a reversed-phase column [eluent: water (0.5% ammonia liquor)/acetonitrile, acetonitrile: 0~50%], and the product was lyophilized to obtain 5-(5-((1H-pyrrolo[2,3-b]pyridin-3-yl)methyl)-6-methylpyridin-2-yl)-2-(isopropylamino)-3-methylpyrimidin-4(3H)-one (7 mg, yield 35%). MS m/z (ESI): 389 [M+H]+.

1H NMR (400 MHz; DMSO-d6) δ 11.43 (s, 1H), 8.62 (s, 1H), 8.18 (dd, J=4.8, 1.5 Hz, 1H), 8.04 (d, J=8.1 Hz, 1H), 7.86-7.80 (m, 1H), 7.46 (d, J=8.2 Hz, 1H), 7.20 (d, J=2.4 Hz, 1H), 7.03-6.95 (m, 2H), 4.40-4.25 (m, 1H), 4.03 (s, 2H), 3.35 (s, 3H), 2.49 (s, 3H), 1.24-1.20 (m, 6H).

Example 8 and 9: Preparation of 5-(5-((5-chloro-1H-pyrrolo[2,3-b]pyridin-3-yl)(methoxy)methyl)-6-methylpyridin-2-yl)-2-(isopropylamino)-3-methylpyrimidin-4(3H)-one (Example 8) and 5-(5-((5-chloro-1H-pyrrolo[2,3-b]pyridin-3-yl)(hydroxy)methyl)-6-methylpyridin-2-yl)-2-(isopropylamino)-3-methylpyrimidin-4(3H)-one (Example 9)

example 8

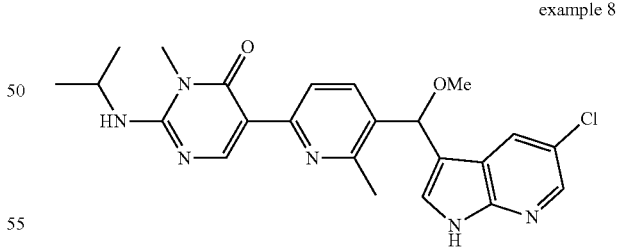

example 9

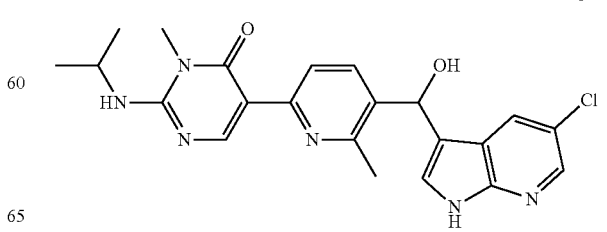

6-(2-(isopropylamino)-1-methyl-6-oxo-1,6-dihydropyrimidin-5-yl)-2-methylnicotinaldehyde (24 mg, 0.1 mmol) was dissolved in methanol (2 mL), and potassium hydroxide (20 mg, 3.4 mmol) and 5-chloro-7-azaindole (13 mg, 0.1 mmol) were added. The reaction solution was stirred overnight at room temperature. After the reaction was completed, the reaction solution was diluted with ethyl acetate (10 mL) and washed twice with water, and the organic phase was dried, concentrated and then separated by thin layer chromatography [eluent: dichloromethane~dichloromethane/methanol (12:1)] to obtain 5-(5-((5-chloro-1H-pyrrolo[2,3-b]pyridin-3-yl)(methoxy)methyl)-6-methylpyridin-2-yl)-2-(isopropylamino)-3-methylpyrimidin-4(3H)-one (18 mg, yield 50%). MS m/z (ESI): 453 [M+H]$^+$.

$^1$H NMR (400 MHz, DMSO-d$_6$) δ 11.90 (s, 1H), 8.66 (s, 1H), 8.27-8.18 (m, 2H), 7.96 (d, J=2.4 Hz, 1H), 7.82 (d, J=8.3 Hz, 1H), 7.35 (d, J=2.6 Hz, 1H), 7.02 (d, J=7.6 Hz, 1H), 5.72 (s, 1H), 4.40-4.20 (m, 1H), 3.37 (s, 3H), 3.30 (s, 3H), 2.40 (s, 3H), 1.24-1.21 (m, 6H).

Meanwhile, 5-(5-((5-chloro-1H-pyrrolo[2,3-b]pyridin-3-yl)(hydroxy)methyl)-6-methylpyridin-2-yl)-2-(isopropylamino)-3-methylpyrimidin-4(3H)-one (6 mg, yield 16%) was obtained. MS m/z (ESI): 439 [M+H]$^+$.

$^1$H NMR (400 MHz, DMSO-d$_6$) δ 11.77 (s, 1H), 8.65 (s, 1H), 8.23-8.14 (m, 2H), 7.93-7.84 (m, 2H), 7.25 (d, J=2.6 Hz, 1H), 7.01 (d, J=7.6 Hz, 1H), 6.07 (d, J=4.6 Hz, 1H), 5.77 (d, J=4.6 Hz, 1H), 4.40-4.20 (m, 1H), 3.37 (s, 3H), 2.40 (s, 3H), 1.22 (d, J=6.6 Hz, 6H).

Example 10: Preparation of 5-(5-((5-chloro-1H-pyrrolo[2,3-b]pyridin-3-yl)methyl)-6-methylpyridin-2-yl)-2-(isopropylamino)-3-methylpyrimidin-4(3H)-one

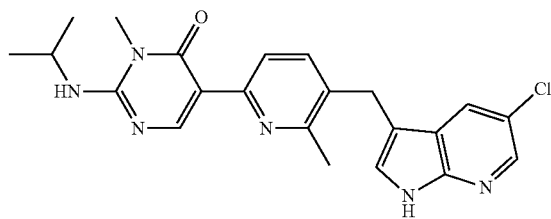

5-(5-((5-chloro-1H-pyrrolo[2,3-b]pyridin-3-yl)(methoxy)methyl)-6-methylpyridin-2-yl)-2-(isopropylamino)-3-methylpyrimidin-4(3H)-one (25 mg, 0.06 mmol) was dissolved in acetonitrile (3 mL), and triethylsilane (0.1 mL, 0.6 mmol) and trifluoroacetic acid (0.05 mL, 0.7 mmol) were added. The reaction solution was stirred at 80° C. for 2 hrs. After the reaction was completed, the reaction solution was alkalified with saturated sodium bicarbonate aqueous solution, and extracted with ethyl acetate, and the organic phase was dried, concentrated and then separated by thin layer chromatography [eluent: dichloromethane~dichloromethane/methanol (10:1)] to obtain 5-(5-((5-chloro-1H-pyrrolo[2,3-b]pyridin-3-yl)methyl)-6-methylpyridin-2-yl)-2-(isopropylamino)-3-methylpyrimidin-4(3H)-one (10 mg, yield 40%). MS m/z (ESI): 423 [M+H]$^+$.

$^1$H NMR (400 MHz, DMSO-d$_6$) δ 11.70 (s, 1H), 8.63 (s, 1H), 8.18 (d, J=2.3 Hz, 1H), 8.06 (d, J=8.0 Hz, 1H), 7.95 (d, J=2.3 Hz, 1H), 7.46 (d, J=8.1 Hz, 1H), 7.30 (d, J=2.4 Hz, 1H), 6.97 (d, J=7.6 Hz, 1H), 4.40-4.20 (m, 1H), 4.02 (s, 2H), 3.35 (s, 3H), 2.48 (s, 3H), 1.22 (d, J=6.7 Hz, 6H).

Example 11: Preparation of 5-(5-(5-chloro-1H-pyrrolo[2,3-b]pyridine-3-carbonyl)-6-methylpyridin-2-yl)-2-(isopropylamino)-3-methylpyrimidin-4(3H)-one

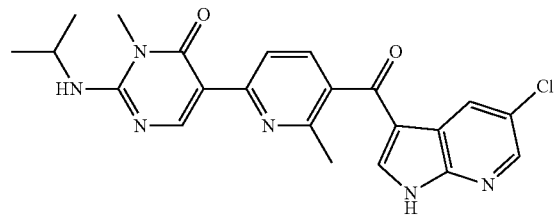 [SMILES: Cc1nc(-c2cnc(NC(C)C)n(C)c2=O)ccc1C(=O)c1c[nH]c2ncc(Cl)cc12]

5-(5-((5-chloro-1H-pyrrolo[2,3-b]pyridin-3-yl)(hydroxy)methyl)-6-methylpyridin-2-yl)-2-(isopropylamino)-3-methylpyrimidin-4(3H)-one (25 mg, 0.06 mmol) was dissolved in dichloromethane (3 mL), and Dess-Martin Periodinane (51 mg, 0.12 mmol) was added. The reaction solution was stirred at room temperature for 2 hrs. After the reaction was completed, the reaction solution was alkalified with saturated sodium bicarbonate aqueous solution, and extracted with dichloromethane, and the organic phase was dried, concentrated and then separated by thin layer chromatography [eluent: dichloromethane~dichloromethane/methanol (12:1)] to obtain 5-(5-(5-chloro-1H-pyrrolo[2,3-b]pyridine-3-carbonyl)-6-methy pyridin-2-yl)-2-(isopropylamino)-3-methylpyrimidin-4(3H)-one (10 mg, yield 40%). MS m/z (ESI): 437 [M+H]$^+$.

$^1$H NMR (400 MHz, DMSO-d$_6$) δ 12.92 (s, 1H), 8.82 (s, 1H), 8.51 (d, J=2.4 Hz, 1H), 8.41 (d, J=2.4 Hz, 1H), 8.33 (d, J=8.2 Hz, 1H), 8.06 (s, 1H), 7.86 (d, J=8.2 Hz, 1H), 7.16 (d, J=7.6 Hz, 1H), 4.40-4.30 (m, 1H), 3.39 (s, 3H), 2.51 (s, 3H), 1.25 (d, J=6.6 Hz, 6H).

Example 12: Preparation of 5-(5-(1-(5-chloro-1H-pyrrolo[2,3-b]pyridin-3-yl)ethyl)-6-methylpyridin-2-yl)-2-(isopropylamino)-3-methylpyrimidin-4(3H)-one

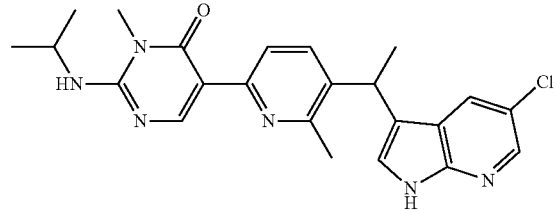 [SMILES: Cc1nc(-c2cnc(NC(C)C)n(C)c2=O)ccc1C(C)c1c[nH]c2ncc(Cl)cc12]

Step 1: Preparation of 1-(6-chloro-2-methylpyridin-3-yl)ethan-1-one

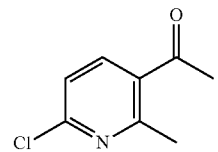

6-chloro-2-methylnicotinaldehyde (312 mg, 2.0 mmol) was dissolved in dry tetrahydrofuran (7 mL), and the methylmagnesium bromide solution (1 mL, 3.0 mmol) was added dropwise under an ice bath. The reaction solution was stirred at room temperature for 2 hrs. The reaction solution was quenched with water and extracted with ethyl acetate, and the organic phase was dried, concentrated. Then the residue was dissolved in dichloromethane (10 mL), and then Dess-Martin Periodinane (1.7 g, 4.0 mmol) was added, and the reaction solution was stirred at room temperature for 2 hrs. The reaction solution was quenched with a saturated sodium bicarbonate solution and extracted with ethyl acetate, and the organic phase was dried, concentrated and then separated by column chromatography [eluent: petroleum ether~petroleum ether/ethyl acetate (5:1)] to obtain 1-(6-chloro-2-methylpyridin-3-yl)ethan-1-one (200) mg, yield 60%). MS m/z (ESI): 170 [M+H]$^+$.

Step 2: Preparation of 5-chloro-3-iodo-1-(triisopropylsilyl)-1H-pyrrolo[2,3-b]pyridine

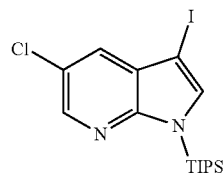

5-chloro-3-iodo-1H-pyrrolo[2,3-b]pyridine (1.25 g, 4.5 mmol) was dissolved in dry tetrahydrofuran (26 mL), and 60% sodium hydride (270 mg, 6.75 mmol) was added in batches under an ice bath and under a nitrogen atmosphere. The reaction solution was stirred for 15 min under a liquid ice bath, then chlorotriisopropylsilane (1.25 mL, 5.9 mmol) was added dropwise. The reaction solution was warmed to room temperature, then stirred for 2 hrs, quenched with a saturated ammonium chloride aqueous solution, and extracted with ethyl acetate. The organic phase was dried, concentrated and then separated by column chromatography [eluent: petroleum ether] to obtain 5-chloro-3-iodo-1-(triisopropylsilyl)-1H-pyrrolo[2,3-b]pyridine (1.75 g, yield 90%).

Step 3: Preparation of 1-(5-chloro-1-(triisopropylsilyl)-1H-pyrrolo[2,3-b]pyridin-3-yl)-1-(6-chloro-2-methylpyridin-3-yl)ethan-1-ol

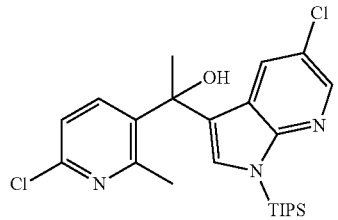

5-chloro-3-iodo-1-(triisopropylsilyl)-1H-pyrrolo[2,3-b]pyridine (1.2 g, 2.65 mmol) was dissolved in dry tetrahydrofuran (10 mL), and isopropylmagnesium chloride solution (1.33 mL, 2.65 mmol) was added dropwise at −40° C. under a nitrogen atmosphere. The reaction solution was stirred at that temperature for 1 hr, then the solution (4 mL) of 1-(6-chloro-2-methylpyridin-3-yl)ethan-1-one (150 mg, 0.88 mmol) in tetrahydrofuran was added dropwise. The reaction solution was warmed to room temperature, then stirred for 2 hrs, quenched with a saturated ammonium chloride aqueous solution, and extracted with ethyl acetate. The organic phase was dried, concentrated and then separated by column chromatography [eluent: petroleum ether~petroleum ether/ethyl acetate (9:1)] to obtain 1-(5-chloro-1-(triisopropylsilyl)-1H-pyrrolo[2,3-b]pyridin-3-yl)-1-(6-chloro-2-methylpyridin-3-yl)ethan-1-ol (340 mg, yield 80%). MS m/z (ESI): 478 [M+H]$^+$.

Step 4: Preparation of 5-chloro-3-(1-(6-chloro-2-methylpyridin-3-yl)vinyl)-1H-pyrrolo[2,3-b]pyridine

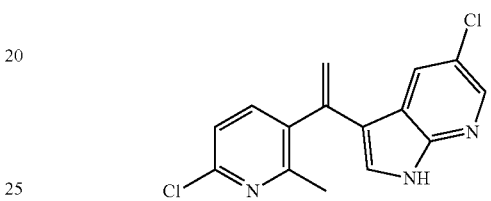

1-(5-chloro-1-(triisopropylsilyl)-1H-pyrrolo[2,3-b]pyridin-3-yl)-1-(6-chloro-2-methylpyridin-3-yl)ethan-1-ol (330 mg, 0.69 mmol) was dissolved in 1,2-dichloroethane (16 mL), then trifluoroacetic acid (0.52 mL) and triethylsilane (0.88 mL, 5.52 mmol) were added. The reaction solution was stirred at room temperature for 1 hr. The reaction solution was concentrated, then alkalified with a saturated sodium bicarbonate aqueous solution and extracted with ethyl acetate, and the organic phase was dried, concentrated and then separated by column chromatography [eluent: dichloromethane dichloromethane/ethyl acetate (6:1)] to obtain 5-chloro-3-(1-(6-chloro-2-methylpyridin-3-yl)vinyl)-1H-pyrrolo[2,3-b]pyridine (187 mg, yield 89%). MS m/z (ESI): 304 [M+H]$^+$.

Step 5: Preparation of tert-butyl 5-chloro-3-(1-(6-chloro-2-methylpyridin-3-yl)vinyl)-1H-pyrrolo[2,3-b]pyridine-1-carboxylate

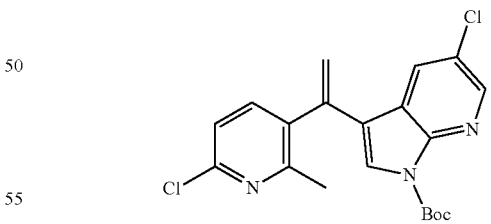

5-chloro-3-(1-(6-chloro-2-methylpyridin-3-yl)vinyl)-1H-pyrrolo[2,3-b]pyridine (100 mg, 0.33 mmol) was dissolved in dichloromethane (5 mL), and diisopropylethylamine (0.2 mL), 4-dimethylaminopyridine (4 mg, 0.03 mmol) and di-tert-butyl dicarbonate (93 mg, 0.43 mmol) were added. The reaction solution was stirred at room temperature for 20 min. The reaction solution was diluted with ethyl acetate and extracted with water, and the organic phase was dried, concentrated and then separated by column chromatography [eluent: petroleum ether~petroleum ether/ethyl acetate (10:

1)] to obtain tert-butyl 5-chloro-3-(1-(6-chloro-2-methylpyridin-3-yl)vinyl)-1H-pyrrolo[2,3-b]pyridine-1-carboxylate (130 mg, yield 990%). MS m/z (ESI): 404 [M+H]+.

Step 6: Preparation of Tert-Butyl 5-chloro-3-(6-(2-(isopropylamino)-4-methoxypyrimidin-5-yl)-2-methylpyridin-3-yl)vinyl)-1H-pyrrolo[2,3-b]pyridine-1-carboxylate

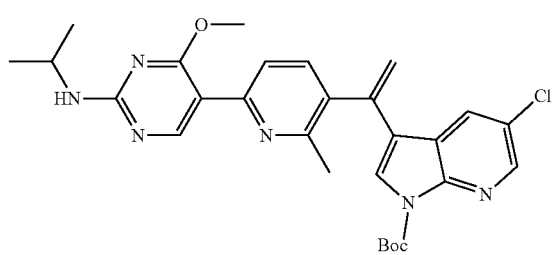 [SMILES: C=C(c1ccc(-c2cnc(NC(C)C)nc2OC)nc1C)c1cn(C(=O)OC(C)(C)C)c2ncc(Cl)cc12]

Tert-butyl 5-chloro-3-(1-(6-chloro-2-methylpyridin-3-yl)vinyl)-1H-pyrrolo[2,3-b]pyridine-1-carboxylate (130 mg, 0.33 mmol) was dissolved in a mixture solvent (1,4-dioxane:water=2:1, 15 mL), and (2-(isopropylamino)-4-methoxypyrimidin-5-yl)boronic acid (585 mg, 2.7 mmol), sodium carbonate (110 mg, 1.01 mmol) and [1,1'-bis(diphenylphosphino)ferrocene]palladium dichloride (49 mg, 0.07 mmol) were added. The nitrogen was charged to replace twice, and the reaction solution was stirred at 90° C. for 90 min. The reaction solution was diluted with ethyl acetate and washed with water, and the organic phase was dried, concentrated and then separated by column chromatography [eluent: petroleum ether~petroleum ether/ethyl acetate (4:1)] to obtain tert-butyl 5-chloro-3-(1-(6-(2-(isopropylamino)-4-methoxypyrimidin-5-yl)-2-methylpyridin-3-yl)vinyl)-1H-pyrrolo[2,3-b]pyridine-1-carboxylate (156 mg, yield 86%). MS m/z (ESI): 535 [M+H]+.

Step 7: Preparation of Tert-Butyl 5-chloro-3-(1-(6-(2-(isopropylamino)-4-methoxypyrimidin-5yl)-2-methylpyridin-3-yl)ethyl)-1H-pyrrolo[2,3-b]pyridine-1-carboxylate

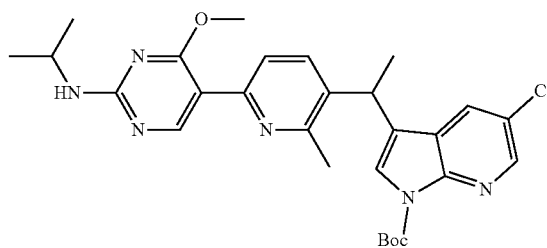

Tert-butyl 5-chloro-3-(1-(6-(2-(isopropylamino)-4-methoxypyrimidin-5-yl)-2-methylpyridin-3-yl)vinyl)-1H-pyrrolo[2,3-b]pyridine-1-carboxylate (156 mg, 0.29 mmol) was dissolved in methanol (5 mL), and 10% palladium on carbon (15 mg) was added. The reaction solution was stirred overnight at room temperature under a hydrogen atmosphere. The reaction solution was filtered, then the filtrate was concentrated and separated by column chromatography [eluent: petroleum ether~petroleum ether/ethyl acetate (4:1)] to obtain tert-butyl 5-chloro-3-(1-(6-(2-(isopropylamino)-4-methoxypyrimidin-5-yl)-2-methylpyridin-3-yl)ethyl)-1H-pyrrolo[2,3-b]pyridine-1-carboxylate (58 mg, yield 36%). MS m/z (ESI): 537 [M+H]+.

Step 8: Preparation of 5-(5-(1-(5-chloro-1H-pyrrolo[2,3-b]pyridin-3-yl)ethyl)-6-methylpyridin-2-yl)-2-(isopropylamino)pyrimidin-4(3H)-one

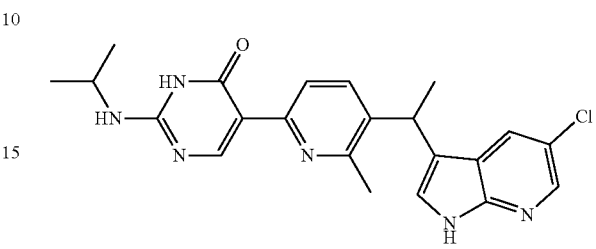

Tert-butyl 5-chloro-3-(1-(6-(2-(isopropylamino)-4-methoxypyrimidin-5-yl)-2-methylpyridin-3-yl)ethyl)-1H-pyrrolo[2,3-b]pyridine-1-carboxylate (58 mg, 0.1 mmol) was dissolved in acetic acid (3 mL), and 40% hydrogen bromide aqueous solution (0.13 mL) was added. The reaction solution was stirred at 90° C. for 6 hrs. The reaction solution was alkalified with a saturated sodium bicarbonate aqueous solution and then extracted with ethyl acetate. The organic phase was dried, concentrated and then separated by column chromatography [eluent: petroleum ether~petroleum ether/ethyl acetate (1:2)] to obtain 5-(5-(1-(5-chloro-1H-pyrrolo[2,3-b]pyridin-3-yl)ethyl)-6-methylpyridin-2-yl)-2-(isopropylamino)pyrimidin-4(3H)-one (43 mg, yield 93%). MS m/z (ESI): 423 [M+H]+.

Step 9: Preparation of Tert-Butyl 5-chloro-3-(1-(6-(2-(isopropylamino)-6-oxo-1,6-dihydropyrimidin-5-yl)-2-methylpyridin-3-yl)ethyl)-1H-pyrrolo[2,3-b]pyridine-1-carboxylate

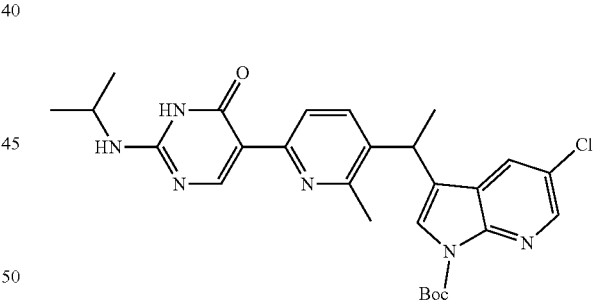

5-(5-(1-(5-chloro-1H-pyrrolo[2,3-b]pyridin-3-yl)ethyl)-6-methylpyridin-2-yl)-2-(isopropylamino)pyrimidin-4(3H)-one (43 mg, 0.1 mmol) was dissolved in dichloromethane (4 mL), and N,N-diisopropylethylamine (0.05 mL), 4-dimethylaminopyridine (1 mg, 0.01 mmol) and di-tert-butyl dicarbonate (33 mg, 0.15 mmol) were added. The reaction solution was stirred at room temperature for 2 hrs. The reaction solution was diluted with ethyl acetate and washed with water, and the organic phase was dried, concentrated and then separated by column chromatography [eluent: petroleum ether~petroleum ether/ethyl acetate (4:1)] to obtain tert-butyl 5-chloro-3-(1-(6-(2-(isopropylamino)-6-oxo-1,6-dihydropyrimidin-5-yl)-2-methylpyridin-3-yl)ethyl)-1H-pyrrolo[2,3-b]pyridine-1-carboxylate (40 mg, yield 75%). MS m/z (ESI): 523 [M+H]+.

Step 10: Preparation of Tert-Butyl 5-chloro-3-(1-(6-(2-(isopropylamino)-1-methyl-6-oxo-1,6-dihydropyrimidin-5-yl)-2-methylpyridin-3-yl)ethyl)-1H-pyrrolo[2,3-b]pyridine-1-carboxylate

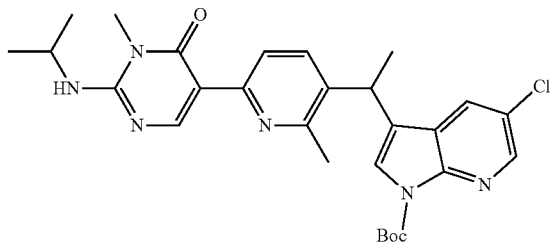 [SMILES: Cc1nc(-c2cnc(NC(C)C)n(C)c2=O)ccc1C(C)c1cn(C(=O)OC(C)(C)C)c2ncc(Cl)cc12]

tert-butyl 5-chloro-3-(1-(6-(2-(isopropylamino)-6-oxo-1,6-dihydropyrimidin-5-yl)-2-methylpyridin-3yl)ethyl)-1H-pyrrolo[2,3-b]pyridine-1-carboxylate (40 mg, 0.08 mmol) was dissolved in N,N-dimethylformamide (3 mL), and potassium carbonate (34 mg, 0.24 mmol) and iodomethane (0.1 mL, 1.5 mmol) were added. The reaction solution was stirred at room temperature for 2 hrs. The reaction solution was diluted with water and extracted with ethyl acetate, and the organic phase was dried, concentrated and then separated by column chromatography [eluent: petroleum ether~petroleum ether/ethyl acetate (4:1)] to obtain tert-butyl 5-chloro-3-(1-(6-(2-(isopropylamino)-1-methyl-6-oxo-1,6-dihydropyrimidin-5-yl)-2-methylpyridin-3-yl)ethyl)-1H-pyrrolo[2,3-b]pyridine-1-carboxylate (20 mg, yield 49%6). MS m/z (ESI): 537 [M+H]$^+$.

Step 11: Preparation of 5-(5-(1-(5-chloro-1H-pyrrolo[2,3-b]pyridin-3-yl)ethyl)-6-methylpyridin-2-yl)-2-(isopropylamino)-3-methylpyrimidin-4(3H)-one

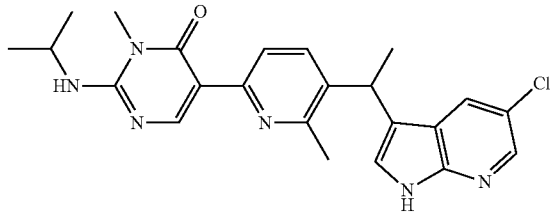 [SMILES: Cc1nc(-c2cnc(NC(C)C)n(C)c2=O)ccc1C(C)c1c[nH]c2ncc(Cl)cc12]

tert-butyl 5-chloro-3-(1-(6-(2-(isopropylamino)-1-methyl-6-oxo-1,6-dihydropyrimidin-5-yl)-2-methylpyridin-3-yl)ethyl)-1H-pyrrolo[2,3-b]pyridine-1-carboxylate (20 mg, 0.04 mmol) was dissolved in dichloromethane (1.5 mL), and trifluoroacetic acid (1.5 mL) was added. The reaction solution was stirred at room temperature for 2 hrs. The reaction solution was concentrated, then alkalified with a saturated sodium bicarbonate aqueous solution and extracted with ethyl acetate, and the organic phase was dried, concentrated and then separated by a reversed-phase column [eluent: water (0.5% ammonia liquor)/acetonitrile, acetonitrile: 0-50%], and the product was lyophilized to obtain 5-(5-(1-(5-chloro-1H-pyrrolo[2,3-b]pyridin-3-yl)ethyl)-6-methylpyridin-2-yl)-2-(isopropylamino)-3-methylpyrimidin-4(3H)-one (6.8 mg, yield 41%). MS m/z (ESI): 437 [M+H]$^+$.

$^1$H NMR (400 MHz, DMSO-d$_6$) δ 11.73 (d, J=2.3 Hz, 1H), 8.64 (s, 1H), 8.15 (d, J=2.4 Hz, 1H), 8.04 (d, J=8.2 Hz, 1H), 7.68 (d, J=2.3 Hz, 1H), 7.46-7.36 (m, 2H), 6.98 (d, J=7.7 Hz, 1H), 4.49 (q. J=7.0 Hz, 1H), 4.31 (h, J=6.7 Hz, 1H), 3.35 (s, 3H), 2.57 (s, 3H), 1.59 (d, J=7.0 Hz, 3H), 1.22 (d, J=6.6 Hz, 6H).

Example 13: Preparation of 3-(5-((5-chloro-1H-pyrrolo[2,3-b]pyridin-3-yl)methyl)-6-methylpyridin-2-yl)-9-methyl-6,7,8,9-tetrahydro-4H-pyrimido[1,2-a]pyrimidin-4-one

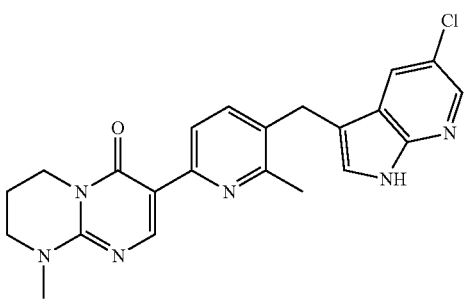 [SMILES: Cc1nc(-c2cnc3n(c2=O)CCCN3C)ccc1Cc1c[nH]c2ncc(Cl)cc12]

3-((5-(5-((5-chloro-1H-pyrrolo[2,3-b]pyridin-3-yl)methyl)-6-methylpyridin-2-yl)-4-methoxypyrimidin-2-yl)(methyl)amino)propan-1-ol (400 mg, 0.88 mmol) was dissolved in 40% hydrobromic acid aqueous solution (10 mL), and the reaction solution was heated to 90° C. and stirred for 16 hrs. After the reaction was completed, the pH of the reaction solution was adjusted to about 8 with a saturated sodium bicarbonate aqueous solution, then the reaction solution was extracted with ethyl acetate (20 mL*3). The organic phase was washed with a saturated brine (50 mL), dried over anhydrous sodium sulfate, concentrated and then separated by thin-layer plate chromatography [developing solvent: CH$_2$Cl$_2$/MeOH (20:1)] to obtain 3-(5-((5-chloro-1H-pyrrolo[2,3-b]pyridin-3-yl)methyl)-6-methylpyridin-2-yl)-9-methyl-6,7,8,9-tetrahydro-4H-pyrimido[1,2-a]pyrimidin-4-one (90 mg, yield 24%). MS m/z (ESI): 421 [M+H]$^+$.

$^1$H NMR (400 MHz, DMSO-d$_6$) δ 11.71 (s, 1H), 8.64 (s, 1H), 8.18 (d, J=2.3 Hz, 1H), 8.08 (d, J=8.1 Hz, 1H), 7.96 (d, J=2.4 Hz, 1H), 7.46 (d, J=8.1 Hz, 1H), 7.30 (d, J=2.4 Hz, 1H), 4.02 (s, 2H), 3.94 (t, J=5.9 Hz, 2H), 3.45 (t, J=5.9 Hz, 2H), 3.15 (s, 3H), 2.48 (s, 3H), 2.05-1.94 (m, 2H).

Examples 14 to 24 were Prepared According to the Synthesis Method of Example 13

| Example No. | Structural formula | Chemical name | MS m/z (ESI): [M + H]$^+$ |
|---|---|---|---|
| 14 |  | 3-(5-((1H-pyrrolo[2,3-b]pyridin-3-yl)methyl)-6-methylpyridin-2-yl)-9-methyl-6,7,8,9-tetrahydro-4H-pyrimido[1,2-a]pyrimidin-4-one | 387 |

| Example No. | Structural formula | Chemical name | MS m/z (ESI): [M + H]+ |
|---|---|---|---|
| 15 | 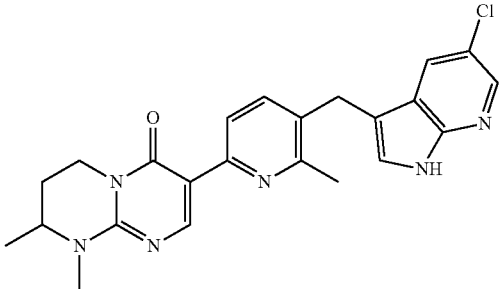 [SMILES: Cc1nc(-c2cnc3n(c2=O)CCC(C)N3C)ccc1Cc1c[nH]c2ncc(Cl)cc12] | 3-(5-((5-chloro-1H-pyrrolo[2,3-b]pyridin-3-yl)methyl)-6-methylpyridin-2-yl)-8,9-dimethyl-6,7,8,9-tetrahydro-4H-pyrimido[1,2-a]pyrimidin-4-one | 435 |
| 16 | 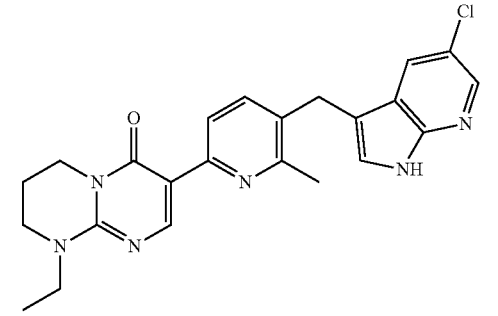 [SMILES: CCN1CCCn2c1ncc(-c1ccc(Cc3c[nH]c4ncc(Cl)cc34)c(C)n1)c2=O] | 3-(5-((5-chloro-1H-pyrrolo[2,3-b]pyridin-3-yl)methyl)-6-methylpyridin-2-yl)-9-ethyl-6,7,8,9-tetrahydro-4H-pyrimido[1,2-a]pyrimidin-4-one | 435 |
| 17 | 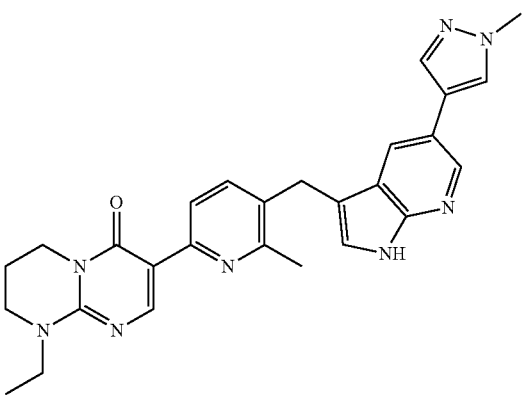 [SMILES: CCN1CCCn2c1ncc(-c1ccc(Cc3c[nH]c4ncc(-c5cnn(C)c5)cc34)c(C)n1)c2=O] | 9-methyl-3-(6-methyl-5-((5-(1-methyl-1H-pyrazol-4-yl)-1H-pyrrolo[2,3-b]pyridin-3-yl)methyl)pyridin-2-yl)-6,7,8,9-tetrahydro-4H-pyrimido[1,2-a]pyrimidin-4-one | 481 |
| 18 | 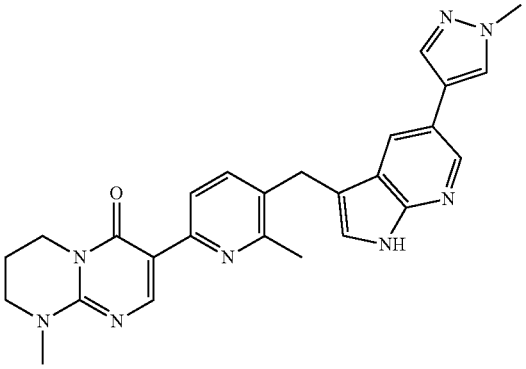 [SMILES: Cc1nc(-c2cnc3n(c2=O)CCCN3C)ccc1Cc1c[nH]c2ncc(-c3cnn(C)c3)cc12] | 9-methyl-3-(6-methyl-5-((5-(1-methyl-1H-pyrazol-4-yl)-1H-pyrrolo[2,3-b]pyridin-3-yl)methyl)pyridin-2-yl)-6,7,8,9-tetrahydro-4H-pyrimido[1,2-a]pyrimidin-4-one | 467 |

| Example No. | Structural formula | Chemical name | MS m/z (ESI): [M + H]+ |
|---|---|---|---|
| 19 | | 3-(5-((1H-pyrrolo[2,3-b]pyridin-3-yl)methyl)-6-methylpyridin-2-yl)-9-ethyl-6,7,8,9-tetrahydro-4H-pyrimido[1,2-a]pyrimidin-4-one | 401 |
| 20 | | 3-(5-((5-fluoro-1H-pyrrolo[2,3-b]pyridin-3-yl)methyl)-6-methylpyridin-2-yl)-9-methyl-6,7,8,9-tetrahydro-4H-pyrimido[1,2-a]pyrimidin-4-one | 405 |
| 21 | | 9-methyl-3-(6-methyl-5-((5-methyl-1H-pyrrolo[2,3-b]pyridin-3-yl)methyl)pyridin-2-yl)-6,7,8,9-tetrahydro-4H-pyrimido[1,2-a]pyrimidin-4-one | 401 |
| 22 | | 3-(5-((5-methoxy-1H-pyrrolo[2,3-b]pyridin-3-yl)methyl)-6-methylpyridin-2-yl)-9-methyl-6,7,8,9-tetrahydro-4H-pyrimido[1,2-a]pyrimidin-4-one | 417 |
| 23 | | 3-(5-((5-hydroxy-1H-pyrrolo[2,3-b]pyridin-3-yl)methyl)-6-methylpyridin-2-yl)-9-methyl-6,7,8,9-tetrahydro-4H-pyrimido[1,2-a]pyrimidin-4-one | 403 |

| Example No. | Structural formula | Chemical name | MS m/z (ESI): [M + H]+ |
|---|---|---|---|
| 24 | | 9-methyl-3-(6-methyl-5-(1H-pyrrolo[2,3-b]pyridine-3-carbonyl)pyridin-2-yl)-6,7,8,9-tetrahydro-4H-pyrimido[1,2-a]pyrimidin-4-one | 401 |

Herein, the nuclear magnetic resonance data of the compounds obtained from the above examples 14 to 24 were listed as follows:

| Example No. | ¹H NMR (400 MHz) |
|---|---|
| 14 | (DMSO-d₆) δ 11.42 (s, 1H), 8.64 (s, 1H), 8.18 (dd, J = 4.6, 1.6 Hz, 1H), 8.06 (d, J = 8.0 Hz, 1H), 7.83 (dd, J = 7.8, 1.6 Hz, 1H), 7.46 (d, J = 8.1 Hz, 1H), 7.20 (d, J = 2.4 Hz, 1H), 6.99 (dd, J = 7.9, 4.7 Hz, 1H), 4.02 (s, 2H), 3.94 (t, J = 6.0 Hz, 2H), 3.45 (t, J = 5.9 Hz, 2H), 3.15 (s, 3H), 2.49 (s, 3H), 2.05-1.94 (m, 2H). |
| 15 | (DMSO-d₆) δ 11.71 (s, 1H), 8.65 (s, 1H), 8.18 (d, J = 2.3 Hz, 1H), 8.08 (d, J = 8.1 Hz, 1H), 7.95 (d, J = 2.3 Hz, 1H), 7.46 (d, J = 8.1 Hz, 1H), 7.30 (d, J = 2.4 Hz, 1H), 4.42-4.27 (m, 1H), 4.02 (s, 2H), 3.74-3.54 (m, 2H), 3.14 (s, 3H), 2.48 (s, 3H), 2.05-1.87 (m, 2H), 1.26 (d, J = 6.5 Hz, 3H). |
| 16 | (DMSO-d₆) δ 11.71 (s, 1H), 8.64 (s, 1H), 8.18 (d, J = 2.3 Hz, 1H), 8.06 (d, J = 8.1 Hz, 1H), 7.95 (d, J = 2.3 Hz, 1H), 7.45 (d, J = 8.1 Hz, 1H), 7.30 (d, J = 2.4 Hz, 1H), 4.02 (s, 2H), 3.93 (t, J = 6.0 Hz, 2H), 3.66 (q ,J = 7.0 Hz, 2H), 3.45 (t, J = 5.9 Hz, 2H), 2.48 (s, 3H), 2.05-1.94 (m, 2H), 1.14 (t, J = 7.0 Hz, 3H). |
| 17 | (DMSO-d₆) δ 11.40 (s, 1H), 8.63 (s, 1H), 8.44 (d, J = 2.1 Hz, 1H), 8.11 (s, 1H), 8.06 (d, J = 8.1 Hz, 1H), 7.98 (d, J = 2.1 Hz, 1H), 7.84 (d, J = 0.8 Hz, 1H), 7.48 (d, J = 8.1 Hz, 1H), 7.16 (d, J = 2.4 Hz, 1H), 4.04 (s, 2H), 3.92 (t, J = 6.0 Hz, 2H), 3.86 (s, 3H), 3.66 (d, J = 7.0 Hz, 2H), 3.45 (t, J = 5.8 Hz, 2H), 2.50 (s, 3H), 2.05-1.94 (m, 2H), 1.14 (t, J = 7.0Hz, 3H). |
| 18 | (DMSO-d₆) δ 11.40 (s, 1H), 8.64 (s, 1H), 8.44 (d, J = 2.0 Hz, 1H), 8.14-8.04 (m, 2H), 7.98 (d, J = 2.1 Hz, 1H), 7.84 (d, J = 0.9 Hz, 1H), 7.48 (d, J = 8.1 Hz, 1H), 7.16 (d, J = 2.4 Hz, 1H), 4.04 (s, 2H), 3.94 (t, J = 6.0 Hz, 2H), 3.86 (s, 3H), 3.45 (t, J = 5.9Hz, 2H), 3.15 (s, 3H), 2.49 (d, J = 1.9 Hz, 3H), 2.05-1.94 (m, 2H), |
| 19 | (DMSO-d₆) δ 11.43 (s, 1H), 8.63 (s, 1H), 8.18 (dd, J = 4.7, 1.6 Hz, 1H), 8.05 (d, J = 8.1 Hz, 1H), 7.83 (dd, J = 7.9, 1.6 Hz, 1H), 7.46 (d,), J = 8.1 Hz, 1H), 7.20 (d, J = 2.4 Hz, 1H), 7.00 (dd, J = 7.9, 4.7 Hz, 1H), 4,02 (s, 2H), 3.92 (t, J = 5.9 Hz, 2H), 3.66 (q, J = 7.0 Hz, 2H), 3.45 (t, J = 5.9Hz, 2H), 2.49 (s, 3H), 2.05-1.94 (m, 2H), 1.14 (t, J = 7.0 1Hz, 3H). |
| 20 | (DMSO-d₆) δ 11.61 (s, 1H), 8.64 (s, 1H), 8.17 (dd, J = 2.8, 1.7 Hz, 1H), 8.07 (d, J = 8.1 Hz, 1H), 7.73 (dd, J = 9.6, 2.8 Hz, 1H), 7.47 (d, J = 8.1 Hz, 1H), 7.31 (s, 1H), 4.00 (s, 2H), 3.94 (t, J = 5.9 Hz, 2H), 3.45 (t, J = 5.9 Hz, 2H), 3.15 (s, 3H), 2.48 (s, 3H), 2.05-1.94 (m, 2H). |
| 21 | (DMSO-d₆) δ 11.27 (s, 1H), 8.64 (s, 1H), 8.15-7.90 (m, 2H), 7.74-7.57 (m, 1H), 7.42 (d, J = 8.1 Hz, 1H), 7.13 (d, J = 2.4 Hz, 1H), 4.02-3.89 (m, 3H), 3.45 (t, J = 5.9 Hz, 2H), 3.15 (s, 2H), 2.49 (s, 3H), 2.33 (s, 2H), 2.05-1.94 (m, 2H). |
| 22 | (DMSO-d₆) δ 11.27 (s, 1H), 8.64 (s, 1H), 8,07 (d, J = 8.0 Hz, 1H), 7.94 (d, J = 2.7 Hz, 1H), 7.46 (d, J = 8.2 Hz, 1H), 7.41 (d, J = 2.8 Hz, 1H), 7.12 (d, J = 2.5 Hz, 1H), 4.00 (s, 2H), 3.94 (t, J = 6.0 Hz, 2H), 3.77 (s, 3H), 3.45 (t, J = 5.9 Hz, 2H), 3.15 (s, 3H), 2.49 (d, J = 2.0 Hz, 3H), 2.05-1.94 (m, 2H). |
| 23 | (DMSO-d₆) δ 11.09 (s, 1H), 8.99 (s, 1H), 8.64 (s, 1H, 8.06 (d, J = 8.1Hz, 1H), 7.80 (d, J = 2.6 Hz, 1H), 7.42 (d, J = 8.1 Hz, 1H), 7.11 (dd, J = 5.7, 2.5 Hz, 2H), 4.00-3.88 (m, 4H), 3.45 (t, J = 5.9 Hz, 2H), 3.15 (s, 3H), 2.49 (s, 3H), 2.05-1.94 (m, 2H). |
| 24 | (DMSO-d₆) δ 12.62 (s, 1H), 8.82 (s, 1H), 8.51 (dd, J = 7.9, 1.7 Hz, 1H), 8.38 (dd, J = 4.8, 1.7 Hz, 1H), 8.33 (d, J = 8.2 Hz, 1H), 7.93 (s, 1H), 7.83 (d, J = 8.2 Hz, 1H), 7.31 (dd, J = 7.9, 4.7 Hz, 1H), 3.99 (t, J = 5.9 Hz, 2H), 3.49 (t, J = 5.9 Hz, 2H), 3.20 (s, 3H), 2.51 (s, 3H), 2.05-1.94 (m, 2H). |

Example 25: Preparation of 5-(5-((5-chloro-1H-pyrrolo[2,3-b]pyridin-3-yl)methyl)-6-methylpyridin-2-yl)-1-isopropyl-1,5-dihydro-4H-imidazo[4,5-c]pyridin-4-one

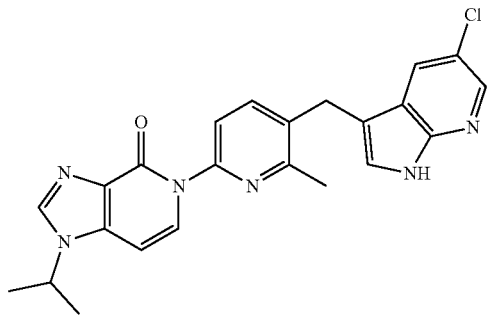 [SMILES: Cc1nc(-n2ccc3c(ncn3C(C)C)c2=O)ccc1Cc1c[nH]c2ncc(Cl)cc12]

Step 1: Preparation of 5-(5-((5-chloro-1H-indol-3-yl)(hydroxy)methyl)-6-methylpyridin-2-yl)-1-isopropyl-1,5-dihydro-4H-imidazo[4,5-c]pyridin-4-one 6-(1-isopropyl-4-oxo-1,4-dihydro-5H-imidazo[4,5-c]pyridin-5-yl)-2-methylnicotinaldehyde (70 mg, 0.24 mmol), 5-chloro-1H-indole (36 mg, 0.24 mmol) and potassium hydroxide (46 mg, 0.83 mmol) were dissolved in methanol (3 mL), and the reaction solution reacted overnight at room temperature. After the reaction was completed, the reaction solution was diluted with water, and extracted with ethyl acetate, and the organic phase was washed with water and brine, dried over sodium sulfate, concentrated and then separated by column chromatography [developing solvent: PE/EA (1:1)] to obtain 5-(5-((5-chloro-1H-indol-3-yl)(hydroxy)methyl)-6-methylpyridin-2-yl)-1-isopropyl-1,5-dihydro-4H-imidazo[4,5-c]pyridin-4-one (41 mg, yield 39%). MS m/z (ESI): 448 [M+H]+.

Step 2: Preparation of 5-(5-((5-chloro-1H-pyrrolo[2,3-b]pyridin-3-yl)methyl)-6-methylpyridin-2-yl)-1-isopropyl-1,5-dihydro-4H-imidazo[4,5-c]pyridin-4-one 5-(5-((5-chloro-1H-indol-3-yl)(hydroxy)methyl)-6-methylpyridin-2-yl)-1-isopropyl-1,5-dihydro-4H-imidazo[4,5-c]pyridin-4-one (45 mg, 0.1 mmol) was dissolved in acetonitrile (4 mL), and triethylsilane (0.15 mL, 0.9 mmol) and trifluoroacetic acid (0.075 mL, 1.05 mmol) were added. The reaction solution was stirred at 80° C. for 2 hrs. After the reaction w as completed, the reaction solution was alkalified with a saturated sodium bicarbonate aqueous solution, and extracted with ethyl acetate, and the organic phase was dried, concentrated and then separated by thin layer-plate chromatography [eluent: dichloromethane dichloromethane/methanol (10:1)] to obtain 5-(5-((5-chloro-1H-pyrrolo[2,3-b]pyridin-3-yl)methyl)-6-methylpyridin-2-yl)-1-isopropyl-1,5-dihydro-4H-imidazo[4,5-c]pyridin-4-one (15 mg, yield 40%). MS m/z (ESI): 433 [M+H]$^+$.

$^1$H NMR (400 MHz, DMSO-d$_6$) δ 11.80 (s, 1H), 8.25-8.17 (m, 2H), 8.06 (d, J=2.4 Hz, 1H), 7.66 (dd, J=7.8, 2.5 Hz, 2H), 7.46 (d, J=8.0 Hz, 1H), 7.39 (d, J=2.5 Hz, 1H), 6.83 (d, J=7.5 Hz, 1H), 4.75-4.60 (m, 1H), 4.13 (s, 2H), 2.55 (s, 3H), 1.51 (d, J=6.8 Hz, 6H).

Biological Test Evaluation

A. CSF-1R In Vitro Biochemical Kinase Study

In the present invention, the inhibitory activity of compounds against the CSF-1R activity was determined by using CSF-1R ADP-Glo assay. The compound-mediated inhibition effect was achieved by inhibiting the production of ADP from consumption of ATP, and the activities of compounds were evaluated by using the ADP-Glo kit (Promega, cat. No. V9101). The specific experimental process was as follows:

1. The kinase reaction performed in the present invention was carried out in a 384-well plate (Perkinelmer, cat. No. 6007290), and 3.95 nM of CSF-1R, 500 μM of ATP and 0.2 mg/mL of polypeptide (Poly (Glu4, Try1), Sigma, cat. No. P0275) were respectively weighed and added to each well:
2. following reagents were then added to each well to reach the final reaction system: 40 mM Tris, pH 7.5, 20 mM MgCl$_2$, 0.01% Triton X-100, 0.1 mg/mL BSA, 2.5 mM DTT and 0.1% DMSO;
3. the reaction was conducted at 30° C. for 60 min;
4. then an equal volume of stop solution (ADP-Glo) was added to the kinase reaction system;
5. the mixed solution was incubated at 25° C. for 60 min, and the kinase reaction was then terminated;
6. a two-fold volume of detection reagent was then added to each well;
7. the mixed solution was incubated at 25° C. for 30 min;
8. the compound IC$_{50}$ value was measured by using a plate reader (Tecan, M1000) and a four-parameter curve was generated in Graphpad Prism. The enzymatic activities of compounds in the specific examples are shown in Table 1.

B. KIT/PDGFRA In Vitro Biochemical Kinase Study
1. Preparation of 1-fold kinase buffer and stop solution
1.1 1-fold kinase buffer: 50 mM HEPES, pH 7.5, 0.0015% Brij-35.
1.2 stop solution: 100 mM HEPES, pH 7.5, 0.015% Brij-35, 0.2% Coating Reagent #3 50 mM EDTA 2. Preparation of compound solution
2.1 Dilution of compound solution
  1) The final concentration of the compound solution was 40 μM. and the concentration of the prepared stock solution was 50 times of the final concentration, i.e., 2 mM.
  2) 80 μL of 100% DMSO was added to the second well of the 96-well plate, then 20 μL of 10 mM compound solution was added, and thereby 2 mM compound solution was prepared, 60 μL of 100% DMSO was added to other wells, 20 μL of compound was taken from the second well, added to the third well and diluted by 4 times. This serial 4-time dilution was conducted in sequence for the total of 10 concentrations.
2.2 5-fold compound solution transferred to a reaction plate
  1) 10 μL of solution was taken from each well of the above 96-well plate and added to another 96-well plate, and 90 μL of kinase buffer was added.
  2) 5 μL of solution was taken from the above 96-well plate and added to a 384-well reaction plate.
2.3 Kinase reaction
  1) KIT/PDGFRA kinase was added to the 1-fold kinase buffer solution to obtain a 2.5-fold kinase solution.
  2) FAM-labeled polypeptide and ATP were added to the 1-fold kinase buffer solution to obtain a 2.5-fold substrate solution.
  3) 10 μL of 2.5-fold kinase solution was added to the 384-well reaction plate, which already contained 5 μL of 5-fold compound in 10% DMSO. And the mixed solution was incubated at room temperature for 10 min.
  4) 10 μL of 2.5-fold substrate solution was added to the 384-well reaction plate.
  5) Kinase reaction and termination: the mixed solution was incubated at 28° C. for a certain period of time, and 25 μL of stop solution was added to stop the reaction.
2.4 Data reading of Caliper EZ Reader II
2.5 Calculation of percent inhibition and IC$_{50}$
  1) Percent conversion data were copied from the Caliper EZ Reader.
  2) Percent conversion was converted into percent inhibition data, wherein, max referred to percent conversion of the DMSO control, and min referred to percent conversion of the negative control without kinase activity.

Percent inhibition=(max−conversion)/(max−min)*100.

3) The IC$_{50}$ value was fitted with XLFit excel add-in version 5.4.0.8: Fitting formula:

Y=Bottom+(Top−Bottom)/(1+(IC$_{50}$/X)^HillSlope).

The enzymatic activities of compounds in the specific examples are shown in Table 1.

C. CSF-1R-Related Cell Proliferation Experiment

Functional effects of compounds on cell proliferation were evaluated by using Cell Titer Glo (CTG) study in the present invention. M-NFS-60 mouse myeloid leukemia lymphocytes (cat. No. CCBJ078) from National Institutes For Food and Drug Control were cultured in the incubator under conditions of RPMI 1640 (Gibco, cat. No. 11875-119), 10% fetal bovine serum (Gibco, 10099-141), human 10 ng/mL M-CSF macrophage colony-stimulating factor (R&D, cat. No. MVN0915101), 37° C. and 5% CO$_2$. Since ATP is an index for viable cell metabolism, CTG (Promega, #G7573) reagent is a homogeneous detection method for detecting the number of viable cells in the culture by quantifying ATP. Therefore, compound-mediated inhibition for cell proliferation/survival was evaluated by quantifying ATP in cells, and the specific experimental process was as follows:

1. The cells were plated into a tissue-culture-medium-treated 96-well plate (Costar #3904) with 5,000 cells/well/80 μL fresh culture medium:
2. 24 hours later, 10 μL culture medium containing testing compound with 10-fold of final concentration was added to each well;
3. 10 μL of culture medium containing M-CSF with 10-fold of the final concentration was then added to each well:
4. dosage effect was evaluated by testing the 3-fold serial dilutions of the compound;
5. after the cells were incubated for 3 days at 37° C. and 5% $CO_2$, the inhibition on cell survival was quantified after 50 μL of CTG was added and the luminescence assay was performed;
6. the compound concentration leading to half maximal inhibitory ($IC_{50}$) and the compound concentration leading to absolute half maximal inhibitory (Absolute $IC_{50}$) were measured by a plate reader (M1000, Tecan) and a four-parameter curve fit in Graphpad Prism 7. The cell viabilities for compounds in the specific examples are shown in Table 1.

D. CSF-1R-Related Cell Proliferation Experiment

Functional effects of compounds on the proliferation of several cell lines were evaluated by Cell Titer Glo (CTG) studies in the present invention, and effects of the compounds on the proliferation of different cells were evaluated to determine the selectivity degree of the compounds. In the study, M-07e human cytomegalic leukemia cells (cat. No. CBP60791) from Nanjing Kebai Biotechnology Co., Ltd. were cultured in an incubator under conditions of RPMI1640 (Gibco, cat. No. 11875-119), 20% fetal bovine serum (Gibco, 10099-141), human 10 ng/mL GM-CSF granulocyte macrophage colony-stimulating factors (R&D, cat. No. 215-GM-010), 37° C. and 5% $CO_2$; and Kasumi-1 human acute myeloblastic leukemia cells (cat. No. CBP60524) were cultured in an incubator under conditions of RPMI1640 (Gibco, cat. No. 11875-119), 20% fetal bovine serum (Gibco, 10099-141), 37° C. and 5% $CO_2$; NCI-H1703 human non-small cell lung squamous carcinoma cells (cat. No. CBP60115) were cultured in an incubator under conditions of RPMI1640 (Gibco, cat. No. 11875-119), 10% fetal bovine serum (Gibco, 10099-141), 37° C. and 5% $CO_2$; and MV-4-11 human acute monocytic leukemia cells (cat. No. CBP60522) were cultured in an incubator under conditions of IMDM (Invitrogen, cat. No. 12440053), 20% fetal bovine serum (Gibco, 10099-141), 37° C. and 5% $CO_2$. Since ATP is an index for viable cell metabolism, CTG (Promega, #G7573) reagent is a homogeneous detection method for detecting the number of viable cells in the culture by quantifying ATP. Therefore, compound-mediated inhibition for cell proliferation/survival was evaluated by quantifying ATP content in cells, and the specific experimental process was as follows. The cell viabilities for compounds in the specific examples are shown in Table 1.

I) M-07e Human Cytomegalic Leukemia Cell:
1. The cells were plated into a tissue-culture-medium-treated 96-well plate (Costar #3904) with 3500 cells/well/80 μL fresh culture medium, and cultured for 24 hrs;
2. the next day, 10 μL of culture medium containing testing compound with 10-fold of final concentration was added to each well;
3. 10 μL of culture medium containing SCF recombinant human stem cell factor (R&D, cat. No. 7466-SC-010) with 10-fold of the final concentration was then added to each well;
4. the dosage effect was evaluated by testing 4-fold serial dilutions of the compound, which started from 18 μM;
5. after the cells were incubated for 3 days at 37° C. and 5% $CO_2$, the inhibition on cell survival was quantified after 50 μL of CTG was added and the luminescence assay was performed;
6. the compound concentration leading to half maximal inhibitory ($IC_{50}$) and the compound concentration leading to absolute half maximal inhibitory (Absolute $IC_{50}$) were measured by a plate reader (M1000, Tecan) and a four-parameter curve fit in Graphpad Prism 7.

II) NCI-H1703 Human Non-Small Cell Lung Squamous Carcinoma Cell
1. The cells were inoculated into a tissue-culture-medium-treated 96-well plate (Costar #3904) with 5000 cells/well/90 μL fresh culture medium, and cultured for 24 hrs;
2. the next day, 10 μL of culture medium containing testing compound with 10-fold of final concentration was added to each well;
3. the dosage effect was evaluated by testing 3-fold serial dilutions of the compound, which started from 18 μM;
4. after the cells were incubated for 3 days at 37° C. and 5% $CO_2$, the inhibition on cell survival was quantified after 50 μL of CTG was added and the luminescence assay was performed;
5. the compound concentration leading to half maximal inhibitory ($IC_{50}$) and the compound concentration leading to absolute half maximal inhibitory (Absolute $IC_{50}$) were measured by a plate reader (M1000, Tecan) and a four-parameter curve fit in Graphpad Prism 7.

III) MV-4-11 Human Acute Monocytic Leukemia Cell
1. The cells were inoculated into a tissue-culture-medium-treated 96-well plate (Costar #3904) with 5000 cells/well/90 μL fresh culture medium, and cultured for 24 hrs;
2. the next day, 10 μL of culture medium containing testing compound with 10-fold of final concentration was added to each well.
3. the dosage effect was evaluated by testing 3-fold serial dilutions of the compound, which started from 18 μM;
4. after the cells were incubated for 3 days at 37° C. and 5% $CO_2$, the inhibition on cell survival was quantified after 50 μL of CTG was added and the luminescence assay was performed;
5. the compound concentration leading to half maximal inhibitory ($IC_{50}$) and the compound concentration leading to absolute half maximal inhibitory (Absolute $IC_{50}$) were measured by a plate reader (M1000, Tecan) and a four-parameter curve fit in Graphpad Prism 7.

TABLE 1

Detection results for enzymatic and cell activities

| | Enzymatic experiment | | | Cytological experiment | | | | |
|---|---|---|---|---|---|---|---|---|
| Example No. | CSF-1R $IC_{50}$ (nM) | KIT $IC_{50}$ (nM) | PDGFRA $IC_{50}$ (nM) | CSF1R $IC_{50}$ (nM) | CSF-1R Absolute $IC_{50}$ (nM) | KIT $IC_{50}$ (nM) | FLT3 $IC_{50}$ (nM) | PDGFRA $IC_{50}$ (nM) |
| 1 | 27.43* | 247.77 | 6911.28 | 46.5 | 18.8 | NT | NT | NT |
| 2 | 19.28 | NT | NT | 214.8 | 39.9 | NT | NT | NT |

TABLE 1-continued

Detection results for enzymatic and cell activities

| | Enzymatic experiment | | | Cytological experiment | | | | |
|---|---|---|---|---|---|---|---|---|
| Example No. | CSF-1R IC$_{50}$ (nM) | KIT IC$_{50}$ (nM) | PDGFRA IC$_{50}$ (nM) | CSF1R IC$_{50}$ (nM) | CSF-1R Absolute IC$_{50}$ (nM) | KIT IC$_{50}$ (nM) | FLT3 IC$_{50}$ (nM) | PDGFRA IC$_{50}$ (nM) |
| 3 | 39.14 | NT | NT | 50.8 | 47.4 | NT | NT | NT |
| 4 | 36.38 | NT | NT | 234.8 | 210.4 | NT | NT | NT |
| 5 | 45.89 | 221.54 | 9269.41 | 77.9 | 47.9 | 1125.0 | >2000.0 | 1824.0 |
| 6 | 88.10 | NT | NT | NT | NT | NT | NT | NT |
| 7 | 36.74 | 50.80 | 998.23 | 39.7 | 33.7 | 834.0 | 1288.0 | >6000.0 |
| 8 | 331.20 | NT | NT | NT | NT | NT | NT | NT |
| 9 | 315.40 | NT | NT | NT | NT | NT | NT | NT |
| 10 | 32.11 | 13.74 | 681.19 | 40.2* | 31.5* | NT | NT | NT |
| 11 | 73.42 | NT | NT | NT | NT | NT | NT | NT |
| 12 | 289.40 | NT | NT | 315.3 | 296.4 | NT | NT | NT |
| 13 | 65.59* | NT | NT | 46.8* | 38.6* | 1195.3* | >6000.0 | >6000.0 |
| 14 | 55.20 | NT | NT | 96.7* | 105.1* | 10571.5* | >18000.0 | >18000.0 |
| 15 | 49.53 | NT | NT | 91.3 | 83.3 | 788.2 | >2000.0 | >2000.0 |
| 16 | 45.65 | NT | NT | 68.6 | 71.8 | 270.6 | 876.3 | 1033.0 |
| 17 | 5.35 | NT | NT | 6.3* | 5.0* | 38.5 | 27.4 | 57.2 |
| 18 | 4.34 | NT | NT | 5.0* | 4.9* | 231.8* | 505.2* | 447.2* |
| 19 | NT | NT | NT | 67.4 | 56.4 | 977.5 | 3043.0 | 3539.0 |
| 20 | 46.12 | NT | NT | 92.2* | 105.8* | 3193.0 | >18000 | >18000 |
| 21 | 96.26 | NT | NT | 54.0* | 45.6* | 1513.0 | >18000 | >18000 |
| 22 | 43.49 | NT | NT | 48.0 | 39.1 | 1517.0 | >6000.0 | >2000.0 |
| 23 | 38.92 | NT | NT | 140.4 | 130.8 | 1844.0 | >2000.0 | >6000.0 |
| 24 | 168.10 | NT | NT | 534.0 | 702.7 | NT | NT | NT |
| 25 | 48.13 | NT | NT | 553.0 | 622.0 | NT | NT | NT |

Notes
1. "NT" is an abbreviation of "Not Tested", and means that an object has not been detected yet.
2. The data marked with "*" at its upper right corner is the average value of results from multiple tests for the compounds of the examples of the present invention.

It can be concluded from the enzymatic activity data of the compounds in the specific examples that the compounds of the present invention have strong inhibitory effects on the CSF-1R kinase activity. It can be concluded from the cell activity data of the compounds in the specific examples that the compounds of the present invention have strong inhibitory effects on the proliferation activity of M-NFS-60 mouse myeloid leukemia lymphocytes that depends on CSF-1R signaling for proliferation. In addition, given the above experimental results, the compounds of the present invention have strong selectivity for KIT, FLT3, and PDGFRA, and are expected to be developed as the new generation of CSF-1R inhibitors with high selectivities, so as to meet clinical use requirements.

All documents mentioned in the present invention are incorporated by reference, just as each document is cited separately as a reference. In addition, it should be understood that various modifications or changes may be made by those skilled in the art after reading the above teachings of the present invention, and these equivalent forms also fall within the scope defined by the claims appended hereto.

The invention claimed is:

1. A compound of formula (IIIa), a stereoisomer or pharmaceutically acceptable salt thereof:

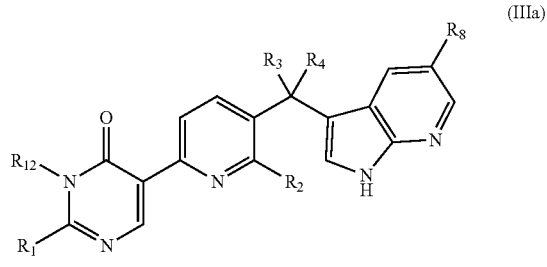

(IIIa)

wherein, $R_1$ is selected from 3-8 membered heterocyclyl, 5-8 membered heteroaryl or —$NR_{17}R_{18}$, or, $R_1$ and $R_{12}$, together with the group directly attached thereto, form 3-10 membered heterocyclyl or 5-10 membered heteroaryl, and above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—$S(O)_rR_{14}$, —$C_{0-4}$—O—$R_{15}$, —$C_{0-4}$—$C(O)OR_{15}$, —$C_{0-4}$—$C(O)R_{16}$, —$C_{0-4}$—O—$C(O)R_{16}$, —$C_{0-4}$—$NR_{17}R_{18}$, —$C_{0-4}$—$C(O)NR_{17}R_{18}$ and —$C_{0-4}$—$N(R_{17})$—$C(O)R_{16}$;

$R_2$ is selected from the group consisting of hydrogen, deuterium, fluorine, chlorine, cyano, methyl, ethyl, cyclopropyl, cyclopropylmethyl, methoxy, ethoxy, trifluoromethyl, trideuteriomethyl, difluoromethyl, dideuteriomethyl, amino and dimethylamino;

$R_3$ and $R_4$ are each independently selected from the group consisting of hydrogen, deuterium, fluorine, chlorine, methyl, trifluoromethyl, trideuteriomethyl, ethyl, isopropyl, cyclopropyl, cyclopropylmethyl, methoxy and methoxyethyl, or, $R_3$ and $R_4$, together with the carbon atom directly attached thereto, form carbonyl, cyclopropyl, cyclobutyl or oxa-cyclobutyl;

$R_8$ is selected from the group consisting of hydrogen, deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, —$C_{0-4}$—$S(O)(=NR_{13})R_{14}$, —$C_{0-4}$—$B(OR_{15})_2$, —$C_{0-4}$—$P(O)(R_{16})_2$, —$C_{0-4}$—$S(O)_rR_{14}$, —$C_{0-4}$—O—$R_{15}$, —$C_{0-4}$—$C(O)OR_{15}$, —$C_{0-4}$—$C(O)R_{16}$, —$C_{0-4}$—O—$C(O)R_{16}$, —$C_{0-4}$—$NR_{17}R_{18}$, —$C_{0-4}$—$C(O)NR_{17}R_{18}$ and —$C_{0-4}$—$N(R_{17})$—$C(O)R_{16}$, and above groups are optionally more further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, —$C_{0-4}$—S(O)$_r$R$_{14}$, —$C_{0-4}$—O—R$_{15}$, —$C_{0-4}$—C(O)OR$_{15}$, —$C_{0-4}$—C(O)R$_{16}$, —$C_{0-4}$—O—C(O)R$_{16}$, —$C_{0-4}$—NR$_{17}$R$_{18}$, —$C_{0-4}$—C(O)NR$_{17}$R$_{18}$ and —$C_{0-4}$—N(R$_{17}$)—C(O)R$_{16}$;

$R_{12}$ is selected from the group consisting of hydrogen, deuterium, methyl, ethyl, cyclopropyl, cyclopropylmethyl, trifluoromethyl, trideuteriomethyl, difluoromethyl, dideuteriomethyl, allyl, cyclobutyl, oxa-cyclobutyl and aza-cyclobutyl;

each $R_{13}$ is independently selected from the group consisting of hydrogen, deuterium, $C_{1-8}$ alkyl, $C_{3-10}$ cycloalkylC$_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)$_r$R$_{14}$, —$C_{0-8}$—O—R$_{15}$, —$C_{0-8}$—C(O)OR$_{15}$, —$C_{0-8}$—C(O)R$_{16}$, —$C_{0-8}$—O—C(O)R$_{16}$, —$C_{0-8}$—NR$_{17}$R$_{18}$, —$C_{0-8}$—C(O)NR$_{17}$R$_{18}$ and —$C_{0-8}$—N(R$_{17}$)—C(O)R$_{16}$;

each $R_{14}$ is independently selected from the group consisting of hydrogen, deuterium, hydroxy, $C_{1-8}$ alkyl, $C_{1-8}$ alkoxy, $C_{2-8}$ alkenyl, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —NR$_{17}$R$_{18}$, and above groups are optionally further substituted by one or more substituents selected from the group consisting of deuterium, halogen, hydroxy, carbonyl, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —NR$_{17}$R$_{18}$;

each $R_{15}$ is independently selected from the group consisting of hydrogen, deuterium, $C_{1-8}$ alkyl, $C_{2-8}$ alkenyl, $C_{3-10}$ cycloalkyl, 3-10 membered heterocyclyl, $C_{5-10}$ aryl and 5-10 membered heteroaryl, and above groups are optionally further substituted by one or more substituents selected from the group consisting of deuterium, halogen, hydroxy, carbonyl, cyano, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —NR$_{17}$R$_{18}$;

each $R_{16}$ is independently selected from the group consisting of hydrogen, deuterium, hydroxy, $C_{1-8}$ alkyl, $C_{1-8}$ alkoxy, $C_{2-8}$ alkenyl, $C_{2-8}$ alkynyl, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —NR$_{17}$R$_{18}$, and above groups are optionally further substituted by one or more substituents selected from the group consisting of deuterium, halogen, hydroxy, cyano, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —NR$_{17}$R$_{18}$;

$R_{17}$ and $R_{18}$ are each independently selected from the group consisting of hydrogen, deuterium, hydroxy, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, sulfonyl, methanesulfonyl, isopropylsulfonyl, cyclopropylsulfonyl, p-toluenesulfonyl, amino, monoalkylamino, dialkylamino and $C_{1-8}$ alkanoyl, and above groups are optionally further substituted by one or more substituents selected from the group consisting of deuterium, halogen, hydroxy, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, amino, monoalkylamino, dialkylamino and $C_{1-8}$ alkanoyl;

or, $R_{17}$ and $R_{18}$, together with the nitrogen atom directly attached thereto, form 4-10 membered heterocyclyl, and above groups are optionally further substituted by one or more substituents selected from the group consisting of deuterium, halogen, hydroxy, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, amino, monoalkylamino, dialkylamino and $C_{1-8}$ alkanoyl;

and r is 0, 1 or 2.

2. The compound of formula (IIIa), the stereoisomer or pharmaceutically acceptable salt thereof of claim 1, wherein, $R_1$ is selected from the group consisting of isopropylamino, N,N-isopropylmethylamino, cyclopropylamino, cyclobutylamino, oxa-cyclobutylamino, 1-methoxypropyl-2-amino, 1,1,1-trifluoropropyl-2-amino, aza-cyclobutyl and aza-cyclopentyl, or, $R_1$ and $R_{12}$, together with the group directly attached thereto, form 5-8 membered heterocyclyl, and the 5-8 membered heterocyclyl is optionally further substituted by one or more substituents selected from the group consisting of deuterium, fluorine, chlorine, $C_{1-4}$ alkyl, $C_{2-4}$ alkenyl, $C_{2-4}$ alkynyl, $C_{1-4}$ haloalkyl, $C_{3-6}$ cycloalkyl, 3-6 membered heterocyclyl, $C_{5-6}$ aryl, 5-6 membered heteroaryl and —$C_{0-4}$—O—R$_{15}$;

$R_{12}$ is selected from the group consisting of hydrogen, deuterium, methyl, ethyl, cyclopropyl, cyclopropylmethyl, trifluoromethyl, trideuteriomethyl, difluoromethyl, dideuteriomethyl, allyl, cyclobutyl, oxa-cyclobutyl and aza-cyclobutyl;

and $R_8$ is selected from the group consisting of hydrogen, deuterium, fluorine, chlorine, hydroxy, cyano, nitro, azido, $C_{1-4}$ alkyl, allyl, ethynyl, $C_{3-6}$ cycloalkyl, 3-6 membered heterocyclyl, 5-6 membered heteroaryl, phenyl, methanesulfonyl, isopropylsulfonyl, aminosulfonyl, methoxy, ethoxy, isopropoxy, methoxycarbonyl, ethoxycarbonyl, acetyl, acetoxy, acetoxymethyl, amino, dimethylamino, aminomethyl, aminocarbonyl, dimethylaminocarbonyl and acetylamino, and above groups are optionally more further substituted by one or more substituents selected from the group consisting of deuterium, fluorine, chlorine, hydroxy, cyano, $C_{1-4}$ alkyl, allyl, ethynyl, cyclopropyl, methoxy and ethoxy.

3. The compound of formula (IIIa), the stereoisomer or pharmaceutically acceptable salt thereof of claim 1, wherein it is selected from the following compounds:

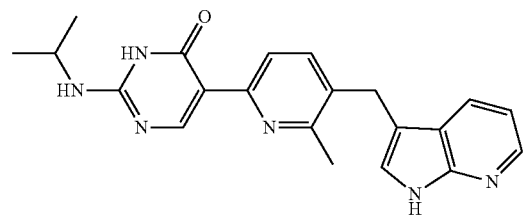

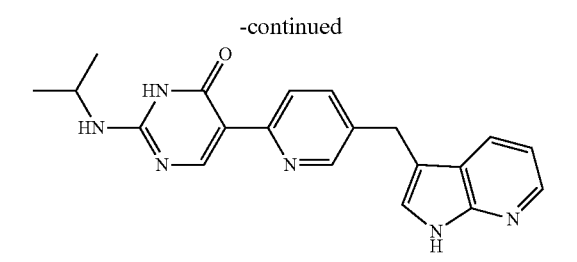
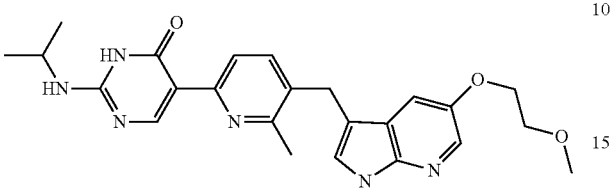
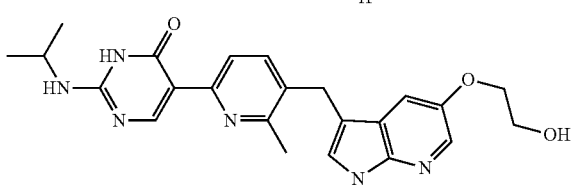
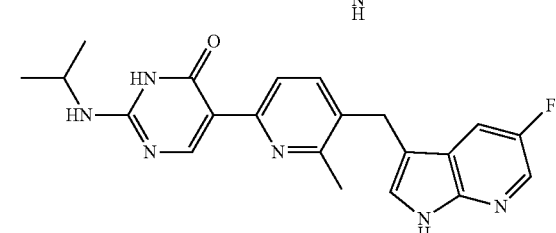
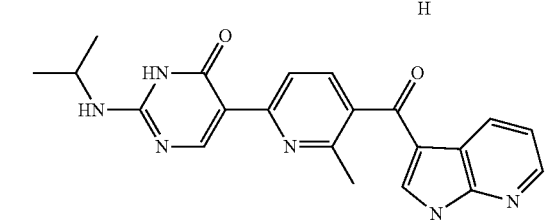
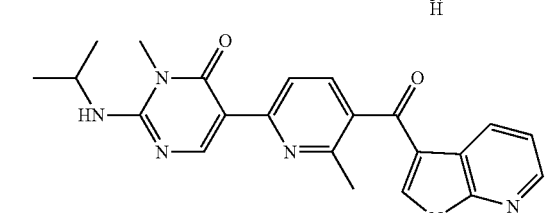
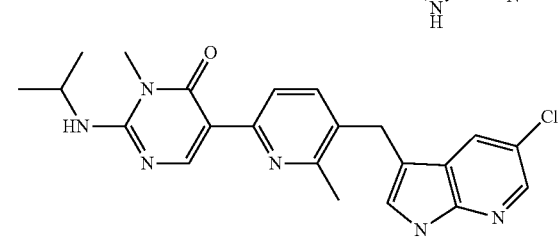
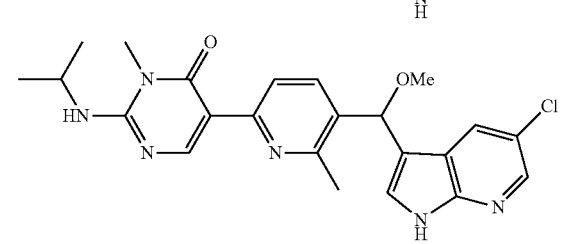
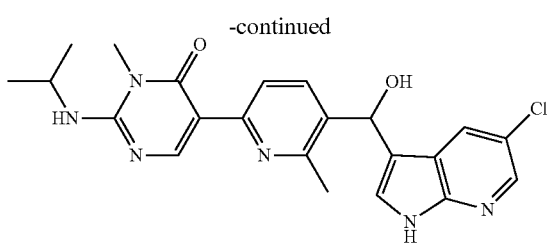
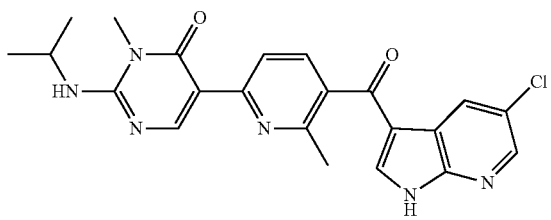
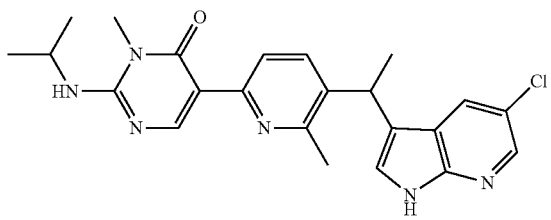
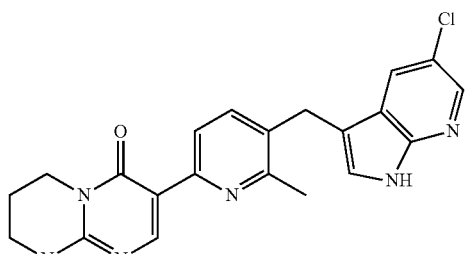
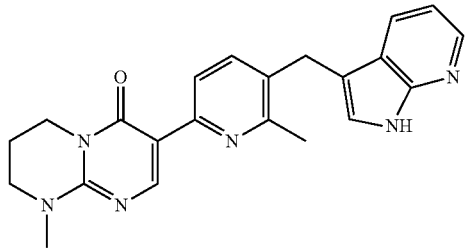
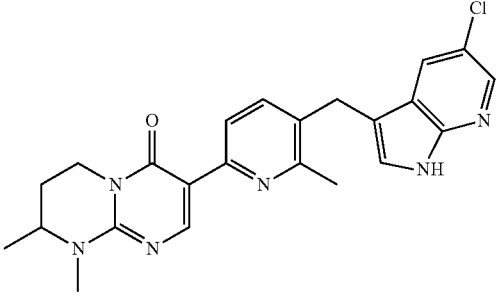

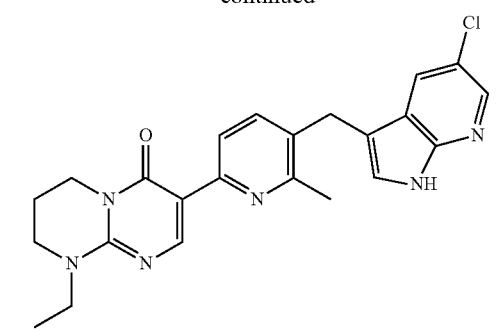
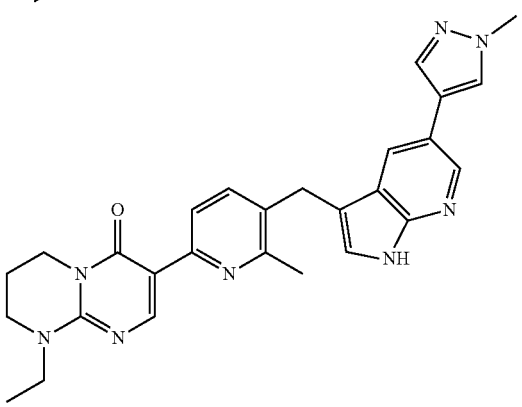
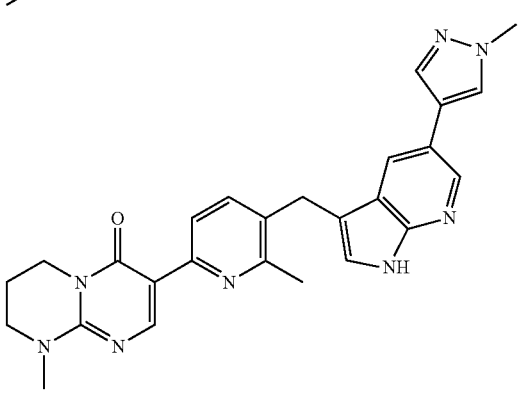
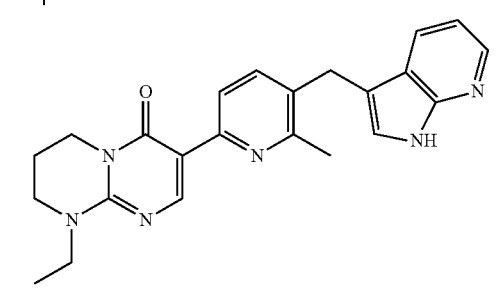
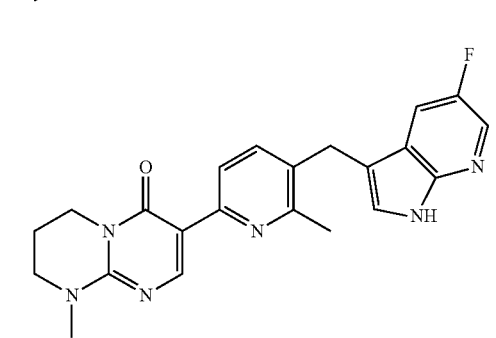
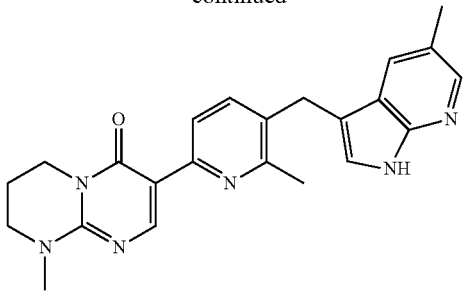
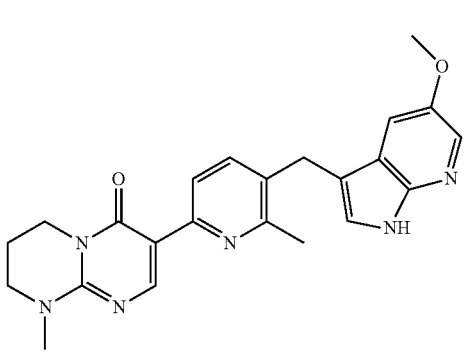
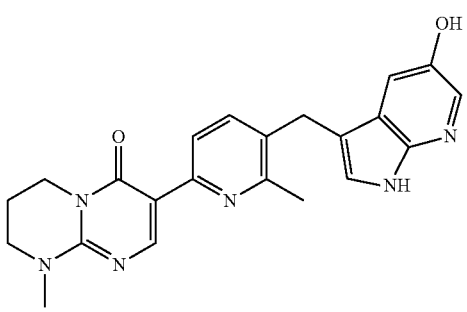
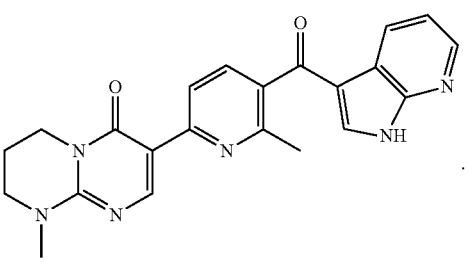
4. A process for preparing the compound of formula (IIIa), the stereoisomer or pharmaceutically acceptable salt thereof of claim 1, comprising the following step:
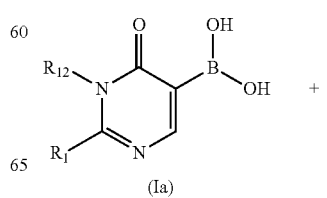

-continued

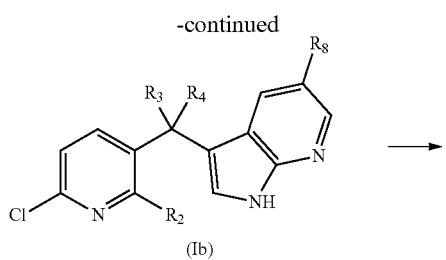
(Ib)

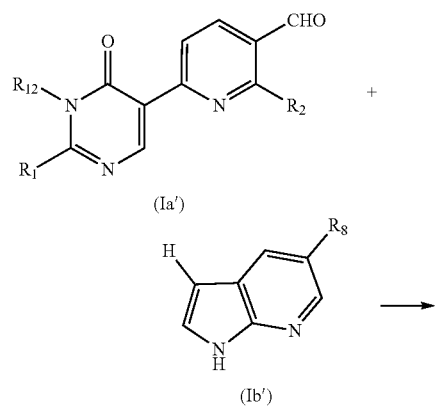
(IIIa)

optionally, the compound of formula (IIIa) is obtained through further reactions according to different substituents;

and R₁, R₂, R₃, R₄, R₈, and R₁₂ are defined as in claim 1.

5. A process for preparing the compound of formula (IIIa), the stereoisomer or pharmaceutically acceptable salt thereof of claim 1, comprising the following synthesis step

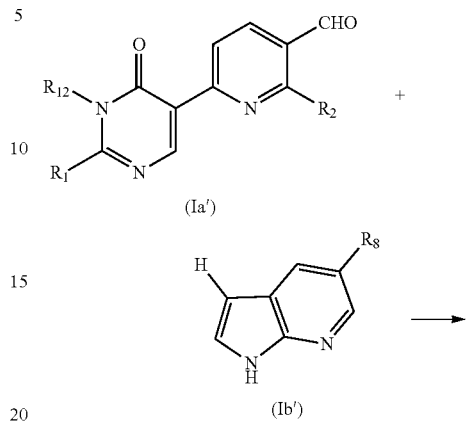

wherein, R' is hydrogen or $C_{1-8}$ alkyl;

optionally, the compound of formula (IIIa) is obtained through further reactions according to different substituents;

and R₁, R₂, R₈, and R₁₂ are defined as in claim 1.

6. The process for preparing the compound of formula (IIIa), the stereoisomer or pharmaceutically acceptable salt thereof of claim 1, comprising the following synthesis steps when R₃ and R₄ are each independently hydrogen:

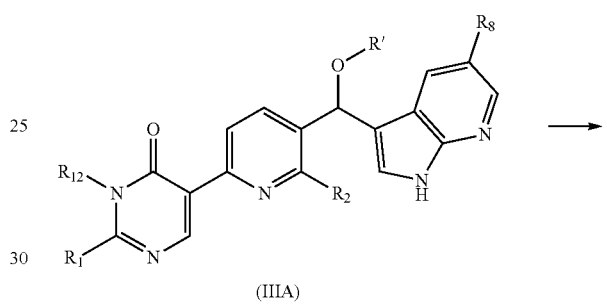

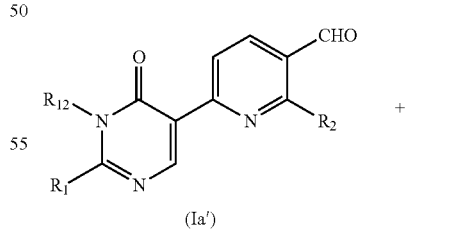
(IIIB)

comprising the following synthesis steps when R₃ is hydrogen, and R₄ is a non-hydrogen substituent:

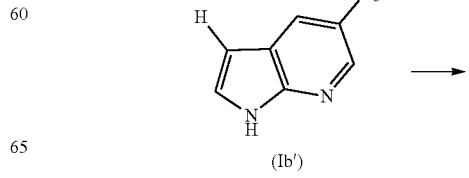

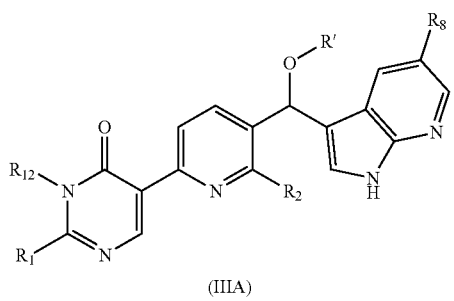
(IIIA)
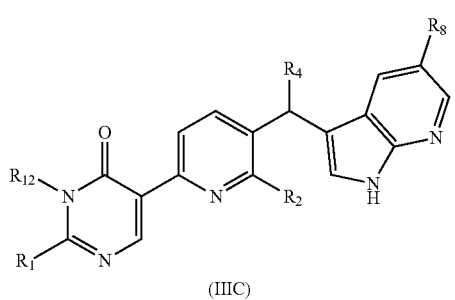
(IIIC)
or comprising the following synthesis steps when R₃ and R₄, together with the carbon atom directly attached thereto, form carbonyl:
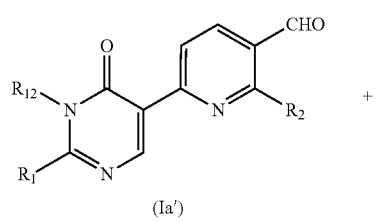
(Ia')
+
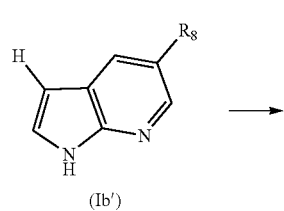
(Ib')
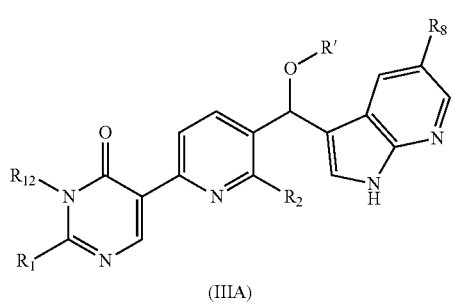
(IIIA)
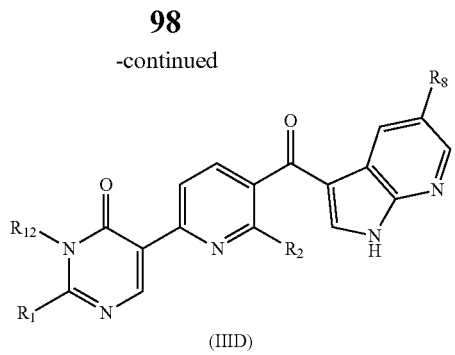
(IIID)
or comprising the following synthesis steps when R₃ and R₄ are each independently a non-hydrogen substituent:
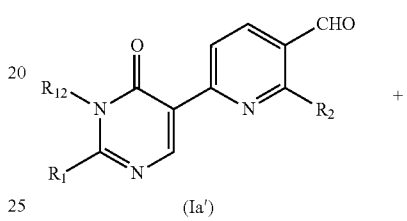
(Ia')
+
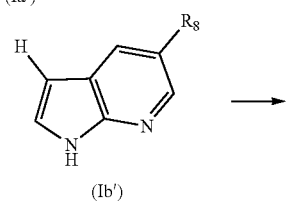
(Ib')
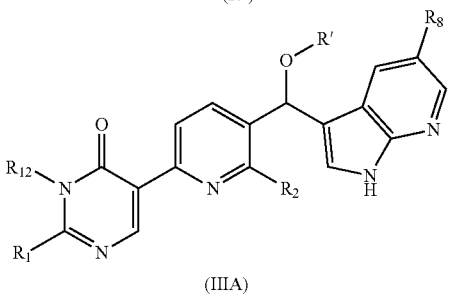
(IIIA)
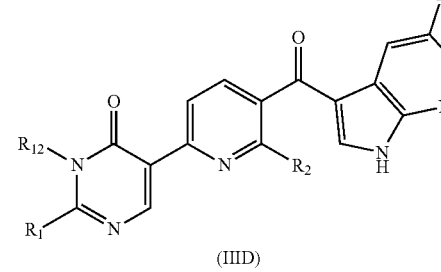
(IIID)
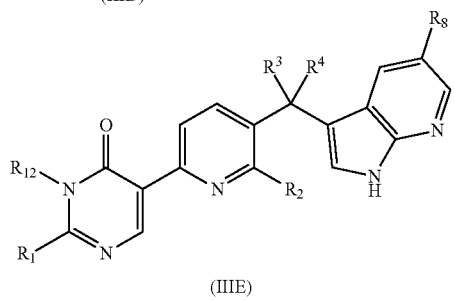
(IIIE)

wherein, R' is hydrogen or $C_{1-8}$ alkyl;

optionally, then the compound of formula (IIIa) is obtained through a further reaction in each of above preparing processes according to different substituents; and $R_1$, $R_2$, $R_3$, $R_4$, $R_8$, and $R_{12}$ are defined as in claim 1.

7. A process for preparing the compound of formula (IIIa), the stereoisomer or pharmaceutically acceptable salt thereof of claim 1, wherein the compound of formula (IIIa) is prepared by the following step:

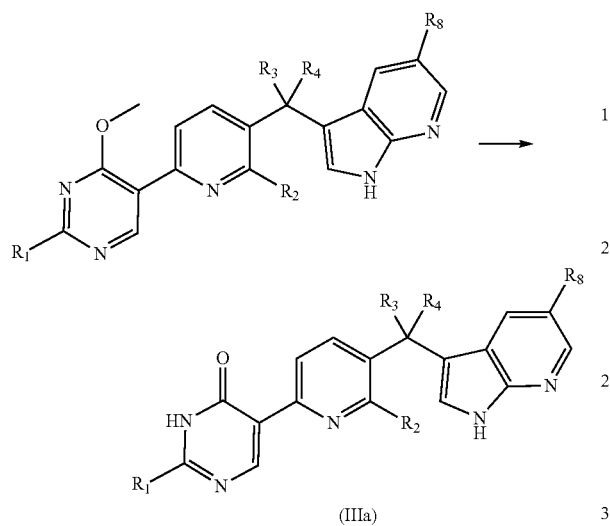

wherein, $R_1$ is selected from the group consisting of 3-8 membered heterocyclyl, 5-8 membered heteroaryl, and —$NR_{17}R_{18}$, and above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—$S(O)_rR_{14}$, —$C_{0-4}$—O—$R_{15}$, —$C_{0-4}$C(O)OR$_{15}$, —$C_{0-4}$—C(O)R$_{16}$, —$C_{0-4}$—O—C(O)R$_{16}$, —$C_{0-4}$—NR$_{17}$R$_{18}$, —$C_{0-4}$—C(O)NR$_{17}$R$_{18}$ and —$C_{0-4}$—N(R$_{17}$)—C(O)R$_{16}$;

or,

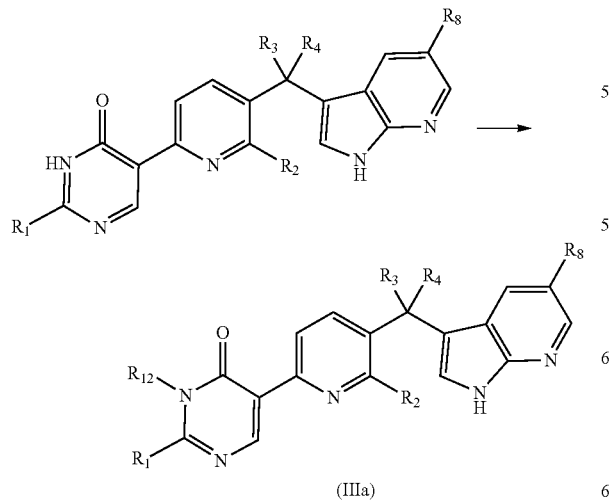

(IIIa)

wherein, $R_1$ is selected from the group consisting of membered heterocyclyl, 5-8 membered heteroaryl, and NR$_{17}$R$_{18}$, and above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—$S(O)_rR_{14}$, —$C_{0-4}$—O—$R_{15}$, $C_{0-4}$C(O)OR$_{15}$, —$C_{0-4}$—C(O)R$_{16}$, —$C_{0-4}$—O—C(O)R$_{16}$, —$C_{0-4}$—NR$_{17}$R$_{18}$, —$C_{0-4}$—C(O)NR$_{17}$R$_{18}$ and —$C_{0-4}$—N(R$_{17}$)—C(O)R$_{16}$;

and $R_{12}$ is selected from the group consisting of deuterium, methyl, ethyl, cyclopropyl, cyclopropylmethyl, trifluoromethyl, trideuteriomethyl, difluoromethyl, dideuteriomethyl, allyl, cyclobutyl, oxa-cyclobutyl and aza-cyclobutyl;

or,

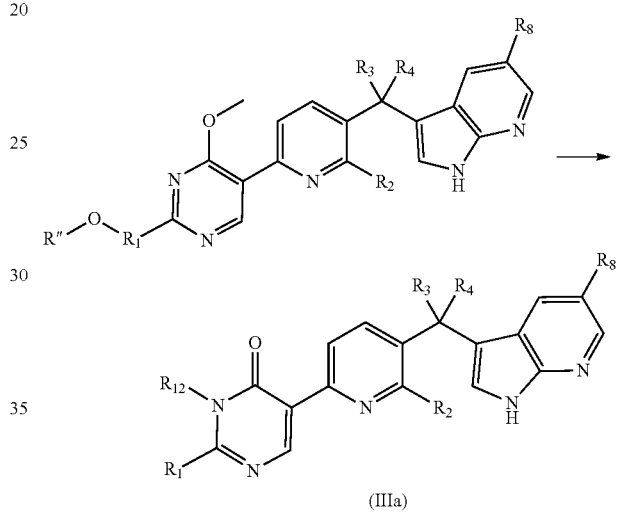

(IIIa)

wherein, in the

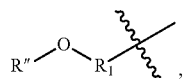, $R_1$ is —$N(R_{17})R_{18}$—, R" is selected from hydrogen or a hydroxy protecting group, and the protecting group is selected from the group consisting of tert-butyldimethylsilyl, trimethylsilyl, isopropyldimethylsilyl, triethylsilyl, triisopropylsilyl, phenyldimethylsilyl, tert-butyldiphenylsilyl, methoxymethyl, p-methoxybenzyl, pivaloyl, tetrahydropyranyl and $C_{1-4}$ alkyl;

in the formula (IIIa), $R_1$ and $R_{12}$, together with the group directly attached thereto, form 3-10 membered heterocyclyl or 5-10 membered heteroaryl, and above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—$S(O)_rR_{14}$, —$C_{0-4}$—O—$R_{15}$, —$C_{0-4}$—C(O)OR$_{15}$, —$C_{0-4}$—C(O)R$_{16}$, —$C_{0-4}$—O—C(O)R$_{16}$, —$C_{0-4}$—NR$_{17}$R$_{18}$, —$C_{0-4}$—C(O)NR$_{17}$R$_{18}$ and —$C_{0-4}$—N(R$_{17}$)—C(O)R$_{16}$;

and $R_2$, $R_3$, $R_4$, $R_8$, $R_{14}$, $R_{15}$, $R_{16}$, $R_{17}$, $R_{18}$ and r are defined as in claim 1.

8. A pharmaceutical composition, comprising the compound of formula (IIIa), the stereoisomer or pharmaceutically acceptable salt thereof of claim 1 and a pharmaceutically acceptable carrier.

9. A method for treating ovarian cancer, pancreatic cancer, prostate cancer, lung cancer, breast cancer, renal carcinoma, liver cancer, cervical cancer, osseous metastasis cancer, papillary thyroid cancer, non-small cell lung cancer, colon cancer, gastrointestinal stromal tumor, melanoma, mesothelioma, glioblastoma, osteosarcoma, multiple myeloma, metabolic disease, leukemia, mastocytosis or mast cell leukemia by inhibiting CSF-1R comprising administering the pharmaceutical composition of claim 8 to a patient.

* * * * *